US009895414B2

(12) United States Patent
Cowin et al.

(10) Patent No.: US 9,895,414 B2
(45) Date of Patent: Feb. 20, 2018

(54) INHIBITION OF CANCER GROWTH AND METASTASIS

(71) Applicants: ROYAL MELBOURNE INSTITUTE OF TECHNOLOGY, Melbourne, Victoria (AU); ABREGEN PTY LTD, Adelaide, South Australia (AU)

(72) Inventors: Allison June Cowin, St. Georges (AU); Zlatko Kopecki, Lockleys (AU); Ian Andrew Darby, Fitzroy North (AU); Dodie Stephanie Pouniotis, Rosanna (AU)

(73) Assignees: ROYAL MELBOURNE INSTITUTE OF TECHNOLOGY, Melbourne, Victoria (AU); ABREGEN PTY LTD, Adelaide, South (AU)

( * ) Notice: Subject to any disclaimer, the term of this patent is extended or adjusted under 35 U.S.C. 154(b) by 0 days.

(21) Appl. No.: 14/655,119

(22) PCT Filed: Dec. 20, 2013

(86) PCT No.: PCT/AU2013/001498
§ 371 (c)(1),
(2) Date: Jun. 24, 2015

(87) PCT Pub. No.: WO2014/100852
PCT Pub. Date: Jul. 3, 2014

(65) Prior Publication Data
US 2015/0320832 A1  Nov. 12, 2015

(30) Foreign Application Priority Data

Dec. 24, 2012 (AU) ................ 2012905692
Apr. 5, 2013 (AU) ................ 2013202668

(51) Int. Cl.
*A61K 39/00* (2006.01)
*A61K 38/17* (2006.01)
*G01N 33/574* (2006.01)
*A61K 31/713* (2006.01)
*G01N 33/68* (2006.01)
*A61K 38/22* (2006.01)
*A61K 38/43* (2006.01)
*C07K 16/18* (2006.01)
*A61K 31/7105* (2006.01)
*C07K 16/16* (2006.01)

(52) U.S. Cl.
CPC ........ *A61K 38/1709* (2013.01); *A61K 31/713* (2013.01); *A61K 31/7105* (2013.01); *A61K 38/22* (2013.01); *A61K 38/43* (2013.01); *C07K 16/18* (2013.01); *G01N 33/5743* (2013.01); *G01N 33/57496* (2013.01); *G01N 33/6875* (2013.01); *A61K 39/00* (2013.01); *A61K 2039/505* (2013.01); *C07K 2317/34* (2013.01); *C07K 2317/76* (2013.01); *G01N 2333/4703* (2013.01); *G01N 2500/00* (2013.01); *G01N 2500/04* (2013.01); *G01N 2500/10* (2013.01)

(58) Field of Classification Search
None
See application file for complete search history.

(56) References Cited

U.S. PATENT DOCUMENTS

2005/0260639 A1  11/2005  Nakamura et al.
2007/0248628 A1  10/2007  Keller et al.

FOREIGN PATENT DOCUMENTS

| JP | 2009-512718 | 3/2009 |
| WO | WO03060146 A2 | 7/2003 |
| WO | 2007/048202 A1 | 5/2007 |

OTHER PUBLICATIONS

Cancer information from National Institute of Cancer, Apr. 29, 2010, pp. 1-2.*
Lu et al., The AAPS Journal 2006, 8(3): E466-E478.*
Nguyen et al., Current Treatment Options in Oncology, 2002, 3:193-203.*
Song, J. et al., "Identifying novel protein complexes in cancer cells using epitope-tagging of endogenous human genes and affinity-purification mass spectrometry", J. Proteone Research, Dec. 2012 (EPub Nov. 7, 2012), vol. 11, No. 12, pp. 5630-561.
Cowin, A.J. et al., "Lycosomal secretion of Flightless I upon injury has the potential to alter inflammation", Communicative & Integrative Biology, Nov./Dec. 2012, vol. 5, No. 6, pp. 546-549.

(Continued)

Primary Examiner — Hong Sang
(74) Attorney, Agent, or Firm — Hovey Williams LLP

(57) ABSTRACT

The present invention relates to methods for treating or preventing cancer and metastasis. More particularly, the present invention relates to methods for treating or preventing cancer by decreasing the expression and/or activity of Flightless I. Also provided are methods for inhibiting the growth of a cancerous cell and methods for inhibiting formation and/or growth of a tumor which also rely on decreasing the expression and/or activity of Flightless I. The present invention also extends to methods for diagnosing cancer, methods for determining if a subject is susceptible to developing cancer, and methods for assessing progression of cancer based on the finding that increased expression and/or activity of Flightless I is associated with cancer development, growth and metastasis. The present invention also provides methods for screening for a candidate therapeutic agent useful for treating or preventing cancer, and related pharmaceutical compositions and kits.

2 Claims, 11 Drawing Sheets

(56) References Cited

OTHER PUBLICATIONS

International Search Report from corresponding PCT/AU2013/001498 dated Jul. 3, 2014 (5 pages).
Supplementary European Search Report and Written Opinion from Application No. EP13867066 (dated Jun. 24, 2016).
Chauhan, et al., "Angiotensin inhibition enhances drug delivery and potentiates chemotherapy by decompressing tumour blood vessels", Nature Communications, 4:2516, 2013, 11 pages.
Provenzano, et al., "Enzymatic Targeting of the Stroma Ablates Physical Barriers to Treatment of Pancreatic Ductal Adenocarcinoma", Cancel Cell 21, Mar. 20, 2012, pp. 418-429.
Wu, et al., "Flightless I homolog negatively regulates ChREBP activity incancer cells", The International Journal of Biochemistry & Cell Biology, vol. 45, 2013, pp. 2688-2697.
Yang, et al., "Identification of differentially expressed genes in metastitic and non-metastatic nasopharyngeal carcinoma cells by suppression substractive hybridization", 2005, Cellular Oncology, vol. 27, pp. 215-223.
Song, et al., "Identifying Novel Protein Complexes in Cancer Cells Using Epitope-Tagging of Endogenous Human Genes and Affinity-Purification Mass Spectrometry", J. Proteome Res., Dec. 7, 2012, vol. 11, issue 12, pp. 5630-5641.
Office Action in corresponding Japanese Patent Application No. 2015-549900, dated Sep. 25, 2017 (English translation attached).

\* cited by examiner

A. Primary Tumours

B. Metastatic tumours

A  FIII+/-

B  FIII9-/-

INHIBITION OF CANCER GROWTH AND METASTASIS

PRIORITY CLAIM

This application is the National Stage of International Patent Application No. PCT/AU2013/001498, filed 20 Dec. 2013, which is hereby incorporated by reference herein in its entirety, and which claims priority from Australian provisional patent application number 2012905692 filed on 24 Dec. 2012, and Australian patent application number 2013202668 filed on 5 Apr. 2013, the contents of which are to be taken as incorporated herein by this reference.

SEQUENCE LISTING

The sequences listed in the accompanying Sequence Listing are presented in accordance with 37C.F.R. 1.822. The Sequence Listing is submitted as an ASCII computer readable text file, which is incorporated by reference herein.

FIELD OF THE INVENTION

The present invention relates generally to methods for treating or preventing cancer. More particularly, the present invention relates to methods for treating or preventing cancer which rely on decreasing the expression and/or activity of Flightless I. Such methods may also be used for inhibiting formation and/or growth of a tumour, inhibiting tumour invasion and metastasis, as well as diagnosing cancer, determining the susceptibility to developing cancer, and assessing the progression of cancer, in a subject.

BACKGROUND OF THE INVENTION

Cancer accounts for more than a tenth of all mortality worldwide, and according to the World Health Organisation cancer was responsible for 7,600,000 deaths in 2008. In Australia, in 2012 it is estimated that more than 120,700 new cases of cancer will be diagnosed (excluding basal and squamous cell carcinoma of the skin), with the most commonly reported cancers expected to be prostate cancer, followed by bowel cancer, breast cancer, melanoma of the skin and lung cancer. In the United States, more than one million new cancer cases arise each year. Of these, approximately half are classified as early-stage diseases.

As detection technologies improve and strategies for routine screening become widely adopted, the number of early stage cancers with no clear evidence of metastatic spread will increase dramatically. Therefore, the development of new and improved methods for the treatment of cancer is of vital importance. At present, common cancer therapies include the use of chemotherapeutic agents which are delivered systemically and have little or no tumour specificity, which results in the potential for harm to healthy organs in the body and causes symptoms such as myelosuppression, mucositis and alopecia. Various forms of radiation are toxic to mammalian cells and have been harnessed successfully for the treatment of cancer. Radioactive isotopes have been used to treat certain cancers, for example cancers of the thyroid and prostate. However, for logistical reasons including the considerable expense of suitable radiation delivery systems, radiation therapy is used less frequently than would otherwise be desirable. As a result, current cancer treatments are far from ideal.

Malignancies of the skin are the most commonly diagnosed cancer type worldwide. Skin cancers are divided into two types, namely melanoma and non-melanoma, with melanoma being the most serious form. Melanoma originates in melanocytes, and whilst it is not the most common type of skin cancer, it underlies the majority of skin cancer-related deaths. Indeed, each year about 48,000 deaths are registered worldwide as being due to malignant melanoma, with about 160,000 new cases of melanoma diagnosed worldwide annualy.

Melanomas fall into four major categories—Superficial spreading melanoma which travels along the top layer of the skin before penetrating more deeply; Lentigo maligna which typically appears as a flat or mildly elevated mottled tan, brown, or dark brown discoloration, and which is found most often in the elderly; Nodular melanoma which occurs anywhere on the body as a dark, protuberant papule or a plaque that varies from pearl to gray to black; and Acral-lentiginous melanoma which is the most uncommon form of melanoma that arises on palmar, plantar, or subungual skin.

Metastasis of melanoma is common and occurs via lymphatics and blood vessels. Local metastasis results in the formation of nearby satellite papules or nodules that may or may not be pigmented, whilst direct metastasis to skin or internal organs can also occur. Despite many years of intensive laboratory and clinical research, there are still limited treatments for melanoma, and those that are available exhibit resistance and multiple unwanted side effects.

Non-melanoma skin cancer has two major sub-types, namely basal cell carcinoma (BCC) and squamous cell carcinoma (SCC). BCCs and SCCs of the skin represent the most common malignancies in the Caucasian population (for example a total of 1,300,000 new cases diagnosed in 2000 in the United States alone). Given that SCCs are highly invasive, metastatic, and are associated with a comparatively high risk of recurrence, they result in significant mortality. SCCs can be diagnosed by biopsy; however, SCCs are typically not as distinct as BCCs or melanomas, making detection and diagnosis difficult. Current methods of treatment, including surgery, radiotherapy, and chemotherapy, require continued monitoring due to the metastatic nature of SCCs. The development of alternative methods of detection and treatment are therefore desirable.

The incidence of non-melanoma skin cancers, including metastatic SCC, is increasing due to the aging populations in western society, and because of its enormously increased incidence among organ transplant recipients. For example, the incidence of SCC in transplant recipients is 40 to 250 times that of the general population, whereas the incidence of BCC is 10 times greater in transplant patients. SCCs in transplant patients are much more aggressive and deadly and out of the 5.1% of transplant patients who die from skin cancer, 60% had SCC and 33% had melanoma, which represents a 10-fold increase in mortality from SCC in comparison with the general population.

Colorectal cancer (CRC) originates in either the large intestine (colon) or the rectum. CRC is the third most common cancer in men and the second most common in women worldwide. In 2008, it was estimated that about 608,000 deaths worldwide could be attributed to CRC annually, accounting for 8% of all cancer deaths, and making CRC the fourth most common cause of death from cancer worldwide. CRC arises from the mucosa forming the inner lining of colon and rectum. Like any other mucosa, it needs to be regenerated and proliferates at a high rate (about one third of all fecal matter are mucosa cells), and is thus susceptible to abnormal growth. In fact, abnormal colonic mucosal growth can be detected in about 40% of all persons over the age of 55 years.

Current technologies to detect mucosal neoplasia (polyps/adenoma) and CRC can be categorized into three classes: In vitro diagnostics—a specimen/sample (blood, stool, or urine) is taken from the test person and analyzed for one or more biomarkers as surrogate markers for colorectal neoplasia/cancer. Exemplary tests include the guaic fecal occult blood test (gFOBT) or the immunological fecal occult blood test (iFOBT); Imaging methods without interventional capabilities, such as X-ray, double contrast barium enema (DCBE), video capsule endoscopy, or computed tomographic coionography; and Imaging methods with interventional capabilities, such as flexible sigmoidoscopy, colonoscopy, laparoscopy, or open surgery.

Unfortunately, the clinical utility of a stool-based screen for CRC is limited because individuals are often unwilling to take the test repeatedly due to the nature of the test. Furthermore, the US National Institutes of Health reported that compliance with endoscopy (flexible sigmoidoscopy or colonoscopy) is dependent on the education and income of the population. Colonoscopy is also an invasive procedure, which is not only inconvenient but may be associated with health risks. Therefore, the overall clinical utility of all endoscopy-based CRC screening is also limited. Accordingly, the current clinical utility of a test for detection of CRC depends not only on its performance characteristics, i.e., sensitivity and specificity, but also on acceptance by the patients and the medical community. Alternative therapies would be welcome.

Lung cancer has been one of the most common cancers for several decades and causes the largest number of cancer deaths in the world. In 2008, there were an estimated 1,610,000 newly diagnosed cases in the world (12.7% of the total) with 1,380,000 deaths (18.2% of the total) caused by cancer of the lung. This exceeded the death rates of breast, prostate and colorectal cancer combined. Lung cancer is categorized into two types, namely small cell lung cancer (SCLC) and non-small cell lung cancer (NSCLC). About 85% of lung cancer cases are categorized as NSCLC, which includes adenocarcinoma, squamous cell carcinoma, and adenosquamous cell carcinoma.

The basis for tumor progression and the aggressive biological behavior of lung cancer remains poorly understood. As with other cancers, the survival rate for lung cancer is much higher if it is detected early. However, lung cancer is difficult to diagnose in the early stages because it may manifest no outward symptoms. When symptoms do occur, they can vary depending on the type, location and spreading pattern of the cancer, and therefore, are not readily associated with cancer. Often, lung cancer is only correctly diagnosed when it has already metastasized. When the disease is detected in an early, localized stage and can be removed surgically, the five-year survival rate can reach 85%. But once the cancer has spread to other organs, especially to distant sites, as few as 2% of patients survive five years.

Potential screening tools to detect early stage lung cancer are chest X-ray and computed tomography (CT) scanning. However, the high cost and high rate of false positives render these radiographic tools impractical for routine widespread use. PET scans are another diagnostic option, but PET scans are costly and generally not amenable for use in screening programs. Currently, age and smoking history are the only two risk factors that have been used as selection criteria by the large screening studies. Accordingly, novel lunger cancer detection methods and therapeutic applications are required.

Cancer metastasis involves multiple biological processes driven by an ensemble of genetic alterations. It is understood that either metastasis-conferring genetic events are acquired stochastically as a tumor grows and expands, or that tumors are "hard-wired" with pro-metastatic genetic alterations early in the evolution of tumors and that these alterations also drive the genesis of cancer. Despite a wealth of knowledge at the molecular and genetic level about major cancer forms in humans, including skin, colorectal, lung, breast, liver, pancreas, and other cancers, there is still a very poor understanding of the molecular events underpinning tumor progression and metastasis. Accordingly, there remains a need to understand which patients will have recurrence of their tumors and ultimately a lethal outcome, and how early diagnosis and treatment may impact these outcomes.

In light of the above, there is a need for the identification of new molecular targets responsible for the aetiology, growth and spread of cancer. Such targets may serve as a basis for the therapeutic intervention and diagnosis of cancer.

Reference to any prior art in this specification is not, and should not be taken as, an acknowledgment or any form of suggestion that this prior art forms part of the common general knowledge in any country.

SUMMARY OF THE INVENTION

The present invention arises out of studies into the role of the Flightless I gene and its encoded protein in cancer development and metastasis. These studies have shown that an increased level of Flightless I is associated with tumour development and progression in vivo.

Accordingly, in a first aspect, the present invention provides a method of treating or preventing cancer in a subject, the method including the step of decreasing the expression and/or activity of Flightless I in the subject.

In one embodiment, decreasing the expression and/or activity of Flightless I in the subject includes administration to the subject of an effective amount of an agent that decreases the expression and/or activity of Flightless I.

In a second aspect, the present invention provides a method of inhibiting the growth of a cancerous cell, the method including the step of decreasing the expression and/or activity of Flightless I in the cell.

In one embodiment, decreasing the expression and/or activity of Flightless I in the cell includes administration to the cell of an effective amount of an agent that decreases the expression and/or activity of Flightless I.

In a third aspect, the present invention provides a method of inhibiting formation and/or growth of a tumour in a subject, or of inhibiting tumour invasion and metastasis in a subject, the method including the step of decreasing the expression and/or activity of Flightless I in the subject.

In one embodiment, decreasing the expression and/or activity of Flightless I in the subject includes administration to the subject of an effective amount of an agent that decreases the expression and/or activity of Flightless I.

In some embodiments of the first to third aspects of the invention, the agent is selected from one or more of the group consisting of a drug, a small molecule, a nucleic acid, an oligonucleotide, an oligopeptide, a polypeptide, a protein, an enzyme, a polysaccharide, a glycoprotein, a hormone, a receptor, a ligand for a receptor, a co-factor, an antisense oligonucleotide, a ribozyme, a small interfering RNA, a microRNA, a short hairpin RNA, a lipid, an aptamer, a virus, and an antibody or an antigen binding part thereof. In some embodiments, the agent is a neutralising antibody to Flightless I, or an antigen binding part thereof. In some embodiments, the agent is a Flightless I binding protein. In one embodiment, the Flightless I binding protein is FLAP-1.

In some embodiments, the cancer is selected from the group consisting of skin cancer, colorectal cancer, and lung cancer. In one embodiment, the skin cancer is squamous cell carcinoma.

In a fourth aspect, the present invention provides a method of diagnosing cancer in a subject, the method including the steps of:

measuring the level of expression and/or activity of Flightless I in the subject;

comparing the level of expression and/or activity of Flightless I in the subject to a reference level of expression and/or activity of Flightless I; and diagnosing cancer in the subject on the basis of the comparison.

In one embodiment, a level of expression and/or activity of Flightless I in the subject that is higher than the reference level of expression and/or activity for Flightless I is indicative of cancer in the subject.

In a fifth aspect, the present invention provides a method of determining if a subject is susceptible to developing cancer, the method including the steps of:

measuring the level of expression and/or activity of Flightless I in the subject;

comparing the level of expression and/or activity of Flightless I in the subject to a reference level of expression and/or activity of Flightless I; and determining if the subject is susceptible to developing cancer on the basis of the comparison.

In one embodiment, a level of expression and/or activity of Flightless I in the subject that is higher than the reference level of expression and/or activity for Flightless I indicates that the subject is susceptible to cancer.

In a sixth aspect, the present invention provides a method of assessing progression of cancer in a subject, the method including the steps of:

measuring the level of expression and/or activity of Flightless I in the subject;

comparing the level of expression and/or activity of Flightless I in the subject to a reference level of expression and/or activity of Flightless I; and assessing the progression of cancer in the subject on the basis of the comparison.

In one embodiment, the subject is undergoing treatment for the cancer. In some embodiments of the sixth aspect of the invention, a level of expression and/or activity of Flightless I in the subject that is higher than the reference level of expression and/or activity for Flightless I is indicative of the progression of cancer in the subject.

In some embodiments of the fourth to sixth aspects of the invention, the level of expression and/or activity of Flightless I is measured in a sample obtained from the subject.

In some embodiments, measuring the level of expression of Flightless I includes measuring the level of Flightless I RNA or protein. In one embodiment, the Flightless I RNA is Flightless I mRNA.

In some embodiments, the cancer is selected from the group consisting of skin cancer, colorectal cancer, and lung cancer. In one embodiment, the skin cancer is squamous cell carcinoma.

In a seventh embodiment, the present invention provides a method of screening for a candidate therapeutic agent useful for treating or preventing cancer in a subject, the method including the step of assaying the candidate therapeutic agent for activity in decreasing the level of expression and/or activity of Flightless I, wherein an agent that decreases the level of expression and/or activity of Flightless I is a candidate therapeutic agent useful for treating or preventing cancer in the subject.

In one embodiment, measuring the level of expression of Flightless I includes measuring the level of Flightless I RNA or protein. In one embodiment, the Flightless I RNA is Flightless I mRNA.

In some embodiments, the cancer is selected from the group consisting of skin cancer, colorectal cancer, and lung cancer. In one embodiment, the skin cancer is squamous cell carcinoma.

In an eighth aspect, the present invention provides a pharmaceutical composition when used for treating or preventing cancer in a subject, the composition including an effective amount of an agent that decreases expression and/or activity of Flightless I.

In one embodiment, the agent is selected from one or more of the group consisting of a drug, a small molecule, a nucleic acid, an oligonucleotide, an oligopeptide, a polypeptide, a protein, an enzyme, a polysaccharide, a glycoprotein, a hormone, a receptor, a ligand for a receptor, a co-factor, an antisense oligonucleotide, a ribozyme, a small interfering RNA, a microRNA, short hairpin RNA, a lipid, an aptamer, a virus, and an antibody or an antigen binding part thereof.

In some embodiments, the agent is a neutralising antibody to Flightless I, or an antigen binding part thereof. In some embodiments, the agent is a Flightless I binding protein. In one embodiment, the Flightless I binding protein is FLAP-1.

In some embodiments, the cancer is selected from the group consisting of skin cancer, colorectal cancer, and lung cancer. In one embodiment, the skin cancer is squamous cell carcinoma.

In a ninth aspect, the present invention provides a kit for diagnosing cancer in a subject, determining if a subject is susceptible to developing cancer, or assessing progression of cancer in a subject, the kit including means for measuring the level of expression and/or activity of Flightless I in the subject.

In one embodiment, a level of expression and/or activity of Flightless I in the subject that is higher than a reference level of expression and/or activity for Flightless I diagnoses cancer in the subject, is indicative that the subject is susceptible to developing cancer, or is indicative of progression of cancer in the subject.

In some embodiments, the level of expression and/or activity of Flightless I is measured in a sample obtained from the subject.

In some embodiments, measuring the level of expression of Flightless I includes measuring the level of Flightless I RNA or protein. In one embodiment, the Flightless I RNA is Flightless I mRNA.

In some embodiments, the cancer is selected from the group consisting of skin cancer, colorectal cancer, and lung cancer. In one embodiment, the skin cancer is squamous cell carcinoma.

BRIEF DESCRIPTION OF THE FIGURES

For a further understanding of the aspects and advantages of the present invention, reference should be made to the following detailed description and Examples, taken in conjunction with the accompanying Figures.

DESCRIPTION OF THE INVENTION

Figure 1:
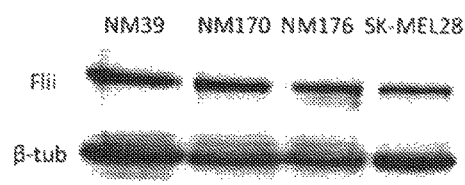
FIG. 1—an autoradiograph showing expression of the Flightless I protein in various melanoma cell lines. The results are representative of two independent experiments.

Nucleotide sequences are referred to herein by a sequence identifier number (SEQ ID NO:). A summary of the sequence identifiers is provided in Table 1. A sequence listing is also provided.

TABLE 1

Summary of Sequence Identifiers

| Sequence Identifier | Sequence |
|---|---|
| SEQ ID NO: 1 | Human Flightless I mRNA sequence - variant 1 (NM_002018.3) |
| SEQ ID NO: 2 | Human Flightless I amino acid sequence - variant 1 (NP_002009.1) |
| SEQ ID NO: 3 | Human Flightless I mRNA sequence - variant 2 (NM_001256264.1) |
| SEQ ID NO: 4 | Human Flightless I amino acid sequence - variant 2 (NP_001243193.1) |
| SEQ ID NO: 5 | Human Flightless I mRNA sequence - variant 3 (NM_001256265.1) |
| SEQ ID NO: 6 | Human Flightless I amino acid sequence - variant 3 (NP_001243194.1) |
| SEQ ID NO: 7 | Human FLAP-1 mRNA sequence - variant 1 (NM_001137550.1) |
| SEQ ID NO: 8 | Human FLAP-1 amino acid sequence - variant 1 (NP_001131022.1) |
| SEQ ID NO: 9 | Human FLAP-1 mRNA sequence - variant 2 (NM_001137551.1) |
| SEQ ID NO: 10 | Human FLAP-1 amino acid sequence - variant 2 (NP_001131023.1) |
| SEQ ID NO: 11 | Human FLAP-1 mRNA sequence - variant 3 (NM_001137552.1) |
| SEQ ID NO: 12 | Human FLAP-1 amino acid sequence - variant 3 (NP_001131024.1) |
| SEQ ID NO: 13 | Human FLAP-1 mRNA sequence - variant 4 (NM_004735.3) |
| SEQ ID NO: 14 | Human FLAP-1 amino acid sequence - variant 4 (NP_004726.2) |
| SEQ ID NO: 15 | Human FLAP-1 mRNA sequence - variant 5 (NM_001137553.1) |
| SEQ ID NO: 16 | Human FLAP-1 amino acid sequence - variant 5 (NP_001131025.1) |

As set out above, the present invention is predicated, in part, on the identification of an association between the Flightless I gene and cancer development, progression and metastasis. For example, the inventors have determined that the level of Flightless I protein is increased in cancer cells, and that overexpression of Flightless I in vivo leads to tumour development and progression. Furthermore, decreasing expression and/or activity of Flightless I leads to a decrease in tumour invasion and metastatis.

Accordingly, in a first aspect, the present invention provides a method of treating or preventing cancer in a subject, the method including the step of decreasing the expression and/or activity of Flightless I in the subject.

As used herein, "Flightless I" is to be understood to refer to a gene that encodes a protein with a gelsolin-like actin binding domain and an N-terminal leucine-rich repeat-protein protein interaction domain. Flightless I was originally identified in *Drosophila* where mutations in the gene caused defects in the flight muscles which, consequently, were unable to support flight. The Flightless I gene has since been found to be present in a number of species, including human, chimpanzee, baboon, monkey, mouse, zebrafish, frog, dog and yeast. Indeed, between the higher order species, the Flightless I protein is highly conserved suggesting that it carries out important, conserved functions.

The human Flightless I gene encodes a 140 kD protein which is a member of the gelsolin family of proteins. The human gene encodes three isoforms variants, the mRNA and amino acid sequences of which are set out in SEQ ID NOs: 1 to 6, and represented by GenBank Accession Numbers NM_002018.3 and NP_002009.1 (variant 1), NM_001256264.1 and NP_001243193.1 (variant 2), and NM_001256265.1 and NP_001243194.1 (variant 3). Further details of the Flightless I gene in human and other species may be accessed from the GenBank database at the National Centre for Biotechnology Information (NCBI) (ncbi.nlm.nih.gov). For example, the Gene ID number for human Flightless I is 2314, for chimpanzee is 454486, for baboon is 101019011, for monkey is 700471, for mouse is 14248, for zebrafish is 560281, for frog is 444748, for dog is 479521, and for yeast is 176215.

Further details regarding the Flightless I gene in other species can be found at the UniGene portal of the NCBI (i.e. UniGene Hs. 513984. Alternatively, details of the nucleotide and amino acid sequence for Flightless I can be accessed from the UniProt database (uniprot.org) wherein the UniProt ID for human Flightless I is Q13045 (variant 1 and 2), and F5H407 (variant 3). The contents of the GenBank and UniProt records are incorporated herein by reference. Human Flightless I will also be referred to herein as "Flii" and "FliI".

It is to be made clear that reference herein to Flightless I, includes a reference to its naturally-occurring variants. In this regard, a "variant" of Flightless I may exhibit a nucleic acid or an amino acid sequence that is at least 80% identical, at least 90% identical, at least 95% identical, at least 98% identical, at least 99% identical, or at least 99.9% identical to native Flightless I. In some embodiments, a variant of Flightless I is expected to retain native biological activity or a substantial equivalent thereof.

As would be understood by a person skilled in the art, the term "gene" refers to a region of genomic nucleotide sequence (nuclear or mitochondrial) associated with a coding region which is transcribed and translated into a functional biomolecule (protein) composed primarily of amino acids. Accordingly, the term "gene" with respect to Flightless I may include regulatory regions (e.g. promoter regions), transcribed regions, protein coding exons, introns, untranslated regions and other functional and/or non-functional sequence regions associated with Flightless I.

The method of the first aspect of the invention requires the step of decreasing the expression and/or activity of Flightless I. As would be understood by a person skilled in the art, the term "expression" includes: (1) transcription of the Flightless I gene into a messenger RNA (mRNA) molecule; and/or (2) translation of the mRNA into the Flightless I protein. In effect, the expression of the Flightless I gene can be decreased at the RNA and/or protein stages of expression. With respect to the term "activity", this should be taken to mean the normal function of the translated Flightless I protein. For example, Flightless I belongs to the Gelsolin family of actin severing proteins which function in the cytoplasm of cells where they control actin organisation. This is achieved by severing pre-existing actin filaments, capping the fast growing filament ends and nucleating or bundling actin filaments to enable filament reassembly into new cytoskeletal structures. Several members of this Gelsolin family, including Flightless I, also have roles in regulating gene transcription and act as nuclear receptor co-activators. Flightless I is a multifunctional protein with a unique structure containing both a gelsolin domain and a Leucine Rich Repeat domain allowing Flightless I to act as a multifunctional protein with major roles in wound healing. Flightless I negatively regulates wound healing through regulating cellular migration and proliferation, cellular adhesion and spreading. Recent findings have confirmed its role in actin polymerisation and capping of actin monomers.

Reference herein to "decrease" with respect to the expression of Flightless I, whether at the transcriptional (mRNA) or translational (protein) stage is intended to mean, for example, at least a 1%, 5%, 10%, 20%, 30%, 40%, 50%, 60%, 70%, 80%, 90%, 100%, 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 5-fold, 10-fold, 20 fold, 50-fold, or 100-fold or greater reduction in the level of Flightless I mRNA or protein in the affected subject. In one embodiment, the expression of Flightless I will be decreased to a level to that observed in a healthy non-affected subject or to that observed in a non-cancerous tissue of the subject.

Reference herein to "decrease" with respect to the activity of Flightless I is intended to mean a reduction in the function of Flightless I in the affected subject. In effect, the activity of Flightless I in the affected subject is to be reduced to a level commensurate with that observed in a healthy non-affected subject and/or in normal healthy tissues of the subject. In some embodiments, the activity of Flightless I may be reduced by at least 1%, 5%, 10%, 20%, 30%, 40%, 50%, 60%, 70%, 80%, 90%, 100%, 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 5-fold, 10-fold, 20 fold, 50-fold, or 100-fold or greater in the affected subject.

Methods which can be used to measure the level of expression (and decrease thereof) of Flightless I in the subject would be known in the art. With respect to measuring a decrease in the transcription of the Flightless I gene into mRNA, levels of mRNA may be measured by techniques which include, but are not limited to, Northern blotting, RNA in situ hybridisation, reverse-transcriptase PCR (RT-PCR), real-time (quantitative) RT-PCR, microarrays, or "tag based" technologies such as SAGE (serial analysis of gene expression). Microarrays and SAGE may be used to simultaneously quantitate the expression of more than one gene. Primers or probes may be designed based on nucleotide sequence of the Flightless I gene or transcripts thereof. Methodology similar to that disclosed in Paik et al., 2004 (*NEJM*, 351(27): 2817-2826), or Anderson et al., 2010 (*Journal of Molecular Diagnostics*, 12(5): 566-575) may be used to measure the expression of the Flightless I gene. Many methods are also disclosed in standard molecular biology text books such as Sambrook et al. (*Molecular Cloning—A Laboratory Manual*, 3$^{rd}$ Ed., Cold Spring Harbor Laboratory Press, 2000).

With respect to RT-PCR, the first step is typically the isolation of total RNA from a sample obtained from the subject under investigation. A typical sample in this instance would be a tumour biopsy sample (and corresponding normal tissue if possible), although other sample sources are contemplated as described below. If the source of RNA is from a tumour, RNA can also be extracted, for example, from frozen or archived paraffin-embedded and fixed (e.g. formalin-fixed) tissue samples previously obtained from the subject. Messenger RNA (mRNA) may be subsequently purified from the total RNA sample. The total RNA sample (or purified mRNA) is then reverse transcribed into cDNA using a suitable reverse transcriptase. The reverse transcription step is typically primed using oligo-dT primers, random hexamers, or primers specific for the Flightless I gene, depending on the RNA template. The cDNA derived from the reverse transcription reaction then serves as a template for a typical PCR reaction. In this regard, two oligonucleotide PCR primers specific for the Flightless I gene are used to generate a PCR product. A third oligonucleotide, or probe, designed to detect a nucleotide sequence located between the other two PCR primers is also used in the PCR reaction. The probe is non-extendible by the Taq DNA polymerase enzyme used in the PCR reaction, and is labelled with a reporter fluorescent dye and a quencher fluorescent dye. Any laser-induced emission from the reporter dye is quenched by the quenching dye when the two dyes are located close together, as they are on the probe. During the PCR amplification reaction, the Taq DNA polymerase enzyme cleaves the probe in a template-dependent manner. The resultant probe fragments disassociate in solution, and signal from the released reporter dye is freed from the quenching effect of the second fluorophore. One molecule of reporter dye is liberated for each new molecule synthesized, and detection of the unquenched reporter dye provides the basis for quantitative interpretation of the data.

In real-time RT-PCR the amount of product formed, and the timing at which the product is formed, in the PCR reaction correlates with the amount of starting template. RT-PCR product will accumulate quicker in a sample having an increased level of mRNA compared to a standard or "normal" sample. Real-time RT-PCR measures either the fluorescence of DNA intercalating dyes such as Sybr Green into the synthesized PCR product, or can measure PCR product accumulation through a dual-labelled fluorigenic probe (i.e., TaqMan probe). The progression of the RT-PCR reaction can be monitored using PCR machines such as the Applied Biosystems' Prism 7000 or the Roche LightCycler which measure product accumulation in real-time. Real-time RT-PCR is compatible both with quantitative competitive PCR and with quantitative comparative PCR. The former uses an internal competitor for the target sequence for normalization, while the latter uses a normalization gene contained within the sample, or a housekeeping gene for RT-PCR.

The production and application of microarrays for measuring the level of expression of the Flightless I gene at the transcriptional level are well known in the art. In general, in a microarray, a nucleotide sequence (for example an oligonucleotide, a cDNA, or genomic DNA) representing a portion or all of the Flightless I gene occupies a known location on a substrate. A nucleic acid target sample (for example total RNA or mRNA) obtained from a subject of interest is then hybridized to the microarray and the amount of target nucleic acid hybridized to each probe on the array is quantified and compared to the hybridisation which occurs to a standard or "normal" sample. One exemplary quantifying method is to use confocal microscope and fluorescent labels. The Affymetrix GeneChip™ Array system (Affymetrix, Santa Clara, Calif.) and the Atlas™ Human cDNA Expression Array system are particularly suitable for quantifying the hybridization; however, it will be apparent to those of skill in the art that any similar systems or other effectively equivalent detection methods can also be used. Fluorescently labelled cDNA probes may also represent the Flightless I nucleic acid target sample. Such probes can be generated through incorporation of fluorescent nucleotides during reverse transcription of total RNA or mRNA extracted from a sample of the subject to be tested. Labelled cDNA probes applied to the microarray will hybridize with specificity to the equivalent spot of DNA on the array. Quantitation of hybridization of each arrayed element allows for assessment of corresponding mRNA abundance in the sample compared to the abundance observed in a standard or "normal" sample. With dual colour fluorescence, separately labelled cDNA probes generated from two sources of RNA are hybridized pairwise to the array. The relative abundance of the transcripts from the two sources corresponding to each specified gene is thus determined simultaneously. The miniaturized scale of the hybridization using microarray analysis affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels.

Methods which can be used to measure a decrease in the level of expression of Flightless I at the translational level (protein level) would be known in the art. For example, the level of Flightless I protein may be measured by techniques which include, but are not limited to, antibody-based testing (including Western blotting, immunoblotting, enzyme-linked immunosorbent assay (ELISA), radioimmunoassay (RIA), immunoprecipitation and dissociation-enhanced lanthanide fluoro immuno assay (DELFIA)), proteomics techniques, surface plasmon resonance (SPR), versatile fibre-based SPR, chemiluminescence, fluorescent polarization, phosphorescence, immunohistochemistry, immunofluorescence, matrix-assisted laser desorption/ionization mass spectrometry (MALDI-MS), as described in WO 2009/004576 (including surface enhanced laser desorption/ionization mass spectrometry (SELDI-MS), especially surface-enhanced affinity capture (SEAC), protein microarrays, surface-enhanced need desorption (SEND) or surface-enhanced photo label attachment and release (SEPAR)), matrix-assisted laser desorption/ionization time-of-flight (MALDI-TOF) mass spectrometry, microcytometry, microarray, microscopy, fluorescence activated cell sorting (FACS), and flow cytometry.

With respect to antibody-based testing methods such as immunohistochemistry and immunoblotting, antibodies or antisera, preferably polyclonal antisera, and most preferably monoclonal antibodies specific for the Flightless I protein are used to detect protein abundance in the subject. The antibodies can be detected by direct labelling of the antibodies themselves, for example with radioactive labels, fluorescent labels, hapten labels such as, biotin, or an enzyme such as horseradish peroxidase or alkaline phosphatase. Alternatively, unlabelled primary antibody may be used in conjunction with a labelled secondary antibody, comprising antisera, polyclonal antisera or a monoclonal antibody specific for the primary antibody. Immunohistochemistry protocols and kits are well known in the art and are commercially available. Antibodies can be produced by methods well known in the art, for example, by immunizing animals with the protein under investigation. Further detailed description is provided below.

Also contemplated are traditional immunoassays including, for example, sandwich immunoassays including ELISA or fluorescence-based immunoassays, as well as other enzyme immunoassays. Nephelometry is an assay performed in liquid phase, in which antibodies are in solution. Binding of the Flightless I protein to the antibody results in changes in absorbance, which are measured. In the SELDI-based immunoassay, a biospecific capture reagent for the Flightless I protein is attached to the surface of an MS probe, such as a pre-activated ProteinChip array (see below). The protein is then specifically captured on the biochip through this reagent, and the captured protein is detected by mass spectrometry (see below).

A further technique for assessing protein levels using an antibody-based platform involves the versatile fibre-based surface plasmon resonance (VeSPR) biosensor, as described in PCT International Publication No. WO 2011/113085. Traditional SPR is a well-established method for label-free bio-sensing that relies on the excitation of free electrons at the interface between a dielectric substrate and a thin metal coating. The condition under which the incoming light couples into the plasmonic wave depends on the incidence angle and the wavelength of the incoming light as well as the physical properties (dielectric constant/refractive index) of the sensor itself and the surrounding environment. For this reason, SPR is sensitive to even small variations in the density (refractive index) in the close vicinity of the sensor, and does not require the use of fluorescent labels. The small variation of refractive index induced by the binding biomolecules such as proteins onto the sensor surface, can be measured by monitoring the coupling conditions via either the incidence angle or the wavelength of the incoming light. Existing SPR systems use the bulky and expensive Krestchmann prism configuration where one side of the prism is coated with a metal such as gold or silver that can support a plasmonic wave. Alternative SPR architectures have been developed based on optical fibres with the metallic coating deposited around a short section of the fibre. This approach reduces the complexity and cost of such sensors, opening a pathway to distinctive applications such as dip sensing. The material at the sensor surface is probed by monitoring the wavelength within a broad spectrum that is absorbed due to coupling to the surface plasmon. These techniques suffer from practical limitations associated with the need for careful temperature calibration, causing difficulty in analysing large numbers of samples consistently. A novel and powerful variant of an optical-fibre based SPR sensor, known as VeSPR, has been developed recently. VeSPR has a number of demonstrated advantages over existing SPR techniques including: (i) higher signal-to-noise ratio thus higher sensitivity; (ii) self-referencing of the transducing signal thus avoiding expensive/bulky temperature control; and (iii) the ability to perform multiplexed detection of different analytes using a single fibre.

Proteomics can also be used to analyse the expression level of Flightless I protein present in a sample at a certain point of time. In particular, proteomic techniques can be used to assess the global changes of protein expression in a sample (also referred to as expression proteomics). Proteomic analysis typically includes: (i) separation of individual proteins in a sample by 2-D gel electrophoresis (2-D PAGE); (ii) identification of the individual polypeptides recovered from the gel, for example by mass spectrometry or N-terminal sequencing; and (iii) analysis of the data using bioinformatics.

Protein microarrays (also termed biochips) may also be used to determine the level of Flightless I protein in a sample. Many protein biochips are described in the art, including for example protein biochips produced by Ciphergen Biosystems, Inc. (Fremont, Calif.), Zyomyx (Hayward, Calif.), Invitrogen (Carlsbad, Calif.), Biacore (Uppsala, Sweden) and Procognia (Berkshire, UK). Examples of such protein biochips are described in the following patents or published patent applications: U.S. Pat. Nos. 6,225,047, 6,537,749, 6,329,209, and 5,242,828, and PCT International Publication Nos. WO 00/56934 and WO 03/048768.

The level of Flightless I protein can also be measured by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these. The mass spectrometer may be a laser desorption/ionization mass spectrometer. In laser desorption/ionization mass spectrometry, the Flightless I protein to be detected is placed on the surface of a mass spectrometry probe, a device adapted to engage a probe interface of the mass spectrometer and to present the protein to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer. The analysis of Flightless I protein by LDI can take the form of MALDI or of SELDI, as described below.

The SELDI method is described, for example, in U.S. Pat. Nos. 5,719,060 and 6,225,047, and relates to a method of desorption/ionization gas phase ion spectrometry (e.g. mass spectrometry) in which an analyte (in this instance the Flightless I protein to be detected) is captured on the surface of a SELDI mass spectrometry probe. SELDI also encompasses affinity capture mass spectrometry, surface-enhanced affinity capture (SEAC) and immuno-capture mass spectrometry (icMS) as described by Penno M A et al. (2012) *Res. Vet. Sci.* 93: 611-617. These platforms involve the use of probes that have a material on the probe surface that captures proteins through a non-covalent affinity interaction (adsorption) between the material and the protein. The material is variously called an "adsorbent," a "capture reagent," an "affinity reagent" or a "binding moiety." Such probes can be referred to as "affinity capture probes" and as having an "adsorbent surface." The capture reagent can be any material capable of binding a protein. The capture reagent is attached to the probe surface by physisorption or chemisorption. The probes, which may take the form of a functionalised biochip or magnetic bead, may have the capture reagent already attached to the surface, or the probes are pre-activated and include a reactive moiety that is capable of binding the capture reagent, e.g. through a reaction forming a covalent or coordinate covalent bond. Epoxide and acyl-imidizole are useful reactive moieties to covalently bind protein capture reagents such as antibodies or cellular receptors. Nitrilotriacetic acid and iminodiacetic acid are useful reactive moieties that function as chelating agents to bind metal ions that interact non-covalently with histidine containing proteins. Adsorbents are generally classified as chromatographic adsorbents and biospecific adsorbents.

A chromatographic adsorbent refers to an adsorbent material typically used in chromatography. Chromatographic adsorbents include, for example, ion exchange materials, metal chelators (e.g. nitrilotriacetic acid or iminodiacetic acid), immobilized metal chelates, hydrophobic interaction adsorbents, hydrophilic interaction adsorbents, dyes, simple biomolecules (e.g. nucleotides, amino acids, simple sugars and fatty acids) and mixed mode adsorbents (e.g. hydrophobic attraction/electrostatic repulsion adsorbents).

A biospecific adsorbent refers to an adsorbent comprising a biomolecule, e.g. a nucleic acid molecule (e.g. an aptamer), a polypeptide, a polysaccharide, a lipid, a steroid or a conjugate of these (e.g. a glycoprotein, a lipoprotein, a glycolipid, a nucleic acid (e.g. DNA-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target protein than chromatographic adsorbents.

In general, a probe with an adsorbent surface is contacted with a sample being tested for a period of time sufficient to allow the protein under investigation (i.e. Flightless I) to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound protein.

In a further approach, the Flightless I protein can be captured with a solid-phase bound immuno-adsorbent that has antibodies that specifically bind to the protein. After washing the adsorbent to remove unbound material, the protein is eluted from the solid phase and is detected by applying it to a biochip that binds the protein.

Flightless I protein which is bound to the substrates are detected in a gas phase ion spectrometer such as a time-of-flight mass spectrometer. The protein is ionized by an ionization source such as a laser, the generated ions are collected by an ion optic assembly, and then a mass analyzer disperses and analyzes the passing ions. The detector then translates information of the detected ions into mass-to-charge ratios. Detection of protein typically will involve detection of signal intensity. Thus, both the quantity and mass of the protein can be determined.

Another method of laser desorption mass spectrometry is called surface-enhanced neat desorption (SEND). SEND involves the use of probes comprising energy absorbing molecules that are chemically bound to the probe surface ("SEND probe"). The phrase "energy absorbing molecules" (EAM) denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyaceto-phenone derivatives. The energy absorbing molecule may be incorporated into a linear or cross-linked polymer, e.g. a polymethacrylate. For example, the composition can be a co-polymer of α-cyano-4-methacryloyloxy-cinnamic acid and acrylate. Alternatively, the composition may be a co-polymer of α-cyano-4-methacryloyloxycinnamic acid, acrylate and 3-(tri-ethoxy)silyl propyl methacrylate, or may be a co-polymer of α-cyano-4-methacryloyloxycinnamic acid and octadecylmethacrylate ("CI 8 SEND"). SEND is further described in U.S. Pat. No. 6,124,137 and PCT International Publication No. WO 03/64594.

SEAC/SEND is a version of laser desorption mass spectrometry in which both a capture reagent and an energy absorbing molecule are attached to the sample presenting surface. SEAC/SEND probes will therefore allow the capture of Flightless I protein through affinity capture and ionization/desorption without the need to apply external matrix. The CI 8 SEND biochip is a version of SEAC/

SEND, comprising a CI 8 moiety which functions as a capture reagent, and a CHCA moiety which functions as an energy absorbing moiety.

Another version of LDI is called surface-enhanced photolabile attachment and Release (SEPAR). SEPAR involves the use of probes having moieties attached to the surface that can covalently bind Flightless I protein, and then release the protein through breaking a photolabile bond in the moiety after exposure to light, e.g. to laser light. SEPAR and other forms of SELDI are readily adapted to detecting Flightless I protein.

MALDI is a traditional method of laser desorption/ionization. In one MALDI method, the sample to be tested is mixed with matrix and deposited directly on a MALDI chip. Depending on the sample being tested, the Flightless I protein being tested is preferably first captured with biospecific (e.g. an antibody) or chromatographic materials coupled to a solid support such as a resin (e.g. in a spin column). Specific affinity materials that may bind the Flightless I protein being detected are described above. After purification on the affinity material, the Flightless I protein is eluted and then detected by MALDI.

Analysis of proteins by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing using specialized software. Data processing typically includes TOF-to-M/Z transformation to generate a mass spectrum, baseline subtraction to eliminate instrument offsets and high frequency noise filtering to reduce high frequency noise.

Data generated by desorption and detection of Flightless I protein can be analyzed with the use of a programmable digital computer. Data analysis can include steps of determining signal strength of the protein and removing data deviating from a predetermined statistical distribution. For example, the observed peak can be normalized, by calculating the height of the peak relative to a reference. The computer can transform the resulting data into various formats for display. The standard spectrum can be displayed, but in one useful format only the peak height and mass information are retained from the spectrum view, yielding a cleaner image and enabling proteins with nearly identical molecular weights to be more easily seen. In another useful format, two or more spectra are compared, conveniently highlighting Flightless I protein that has varying expression levels between samples. Using any of these formats, one can readily determine whether the Flightless I protein is present in a sample and to what level.

Other methods which may be employed to determine if the level of Flightless I protein has decreased in a subject include assays which rely on know protein/protein interactions. These assays may also be used as an indicator of a decrease in activity of Flightless I in a subject. For example, Flightless I protein has an actin-binding domain, and so assays which measure the amount or level of binding between the Flightless I protein and actin will be a reflection of the level and/or activity of Flightless I protein in a particular sample. This level can be compared to the level of binding in a normal control sample. Furthermore, the Flightless I protein has a leucine-rich repeat which is known to bind proteins such as FLAP-1 (Wilson S A et al., 1998, *Nucleic Acids Res.*, 26: 3460-3467), and Flightless I has been shown to bind directly to the diaphanous-related formins Daam1 and mDia1 (Higashi T et al., 2010, *J. Biol. Chem.*, 285: 16231-16238). Therefore, assays which measure the amount or level of binding between the Flightless I protein and one or more of these other proteins will be a reflection of the level and/or activity of Flightless I protein in a particular sample.

Further assays which may be used to measure the level of decrease in activity of the Flightless I protein will be dictated by the function of the protein. As indicated above, Flightless I regulates gene transcription and acts as a nuclear receptor co-activator. Therefore, a decrease in the activity of Flightless I may be assayed according to a concomitant change in gene transcription as mediated by the Flightless I protein. Flightless I also has a major role in wound healing. Accordingly, an assay based on an assessment of wound healing may be used to measure changes in Flightless I activity. Given that Flightless I negatively regulates wound healing through regulating cellular migration and proliferation, cellular adhesion and spreading, assays which measure for changes in cell migration or proliferation, for example, may also be used to measure the activity of the Flightless I protein.

The terms "treat", "treating" or "treatment," as used herein are to be understood to include within their scope one or more of the following outcomes: (i) inhibiting to some extent the growth of a primary tumour in a subject, including, slowing down and complete growth arrest, and including reducing the growth of the primary tumour after resection; (ii) inhibiting to some extent the growth and formation of one or more secondary tumours in a subject; (iii) reducing the number of tumour cells in a subject; (iv) reducing the size of a tumour in the subject; (v) inhibiting (i.e. reduction, slowing down or complete stopping) of tumor cell infiltration into peripheral organs; (vi) inhibiting (i.e. reduction, slowing down or complete stopping) of metastasis; (vii) improving the life expectancy of a subject as compared to the untreated state; (viii) improving the quality of life of a subject as compared to the untreated state; (ix) alleviating, abating or ameliorating at least one symptom of cancer in a subject; (x) causing regression or remission of cancer in a subject; (xi) relieving a condition in a subject that is caused by cancer; and (xii) stopping symptoms in a subject that are associated with cancer.

The terms "prevent" or "preventing" as used herein are to be understood to include within their scope inhibiting the formation of a primary tumour in a subject and/or inhibiting the formation of one or more secondary tumours in a subject.

In one embodiment of the first aspect of the invention, decreasing the expression and/or activity of Flightless I in the subject includes administration to the subject of an effective amount of an agent that decreases the expression and/or activity of Flightless I. The term "effective amount" as used herein is the quantity which, when administered to a subject, improves the prognosis and/or health state of the subject. The amount to be administered to a subject will depend on the particular characteristics of one or more of the level or amount of resistance to the agent in the subject, the tumour type or cancer being inhibited, prevented or treated, the mode of administration of the agent, and the characteristics of the subject, such as general health, other diseases, age, sex, genotype, and body weight. A person skilled in the art will be able to determine appropriate dosages depending on these and other factors. The effective amount of the agent to be used in the various embodiments of the invention is not particularly limited.

The agent may be any agent that is capable of decreasing the expression and/or activity of Flightless I. For example, the agent may be selected from one or more of the group consisting of a neutralizing antibody (or an antigen binding part thereof), an antisense nucleic acid that binds to Flightless I mRNA and which interferes with translation, a molecule that can specifically repress transcription of endogenous Flightless I mRNA such as a specific DNA or RNA binding protein, a nucleic acid capable of forming a triple helix structure, a small interfering RNA, a microRNA, a short hairpin RNA, a ribozyme that can cleave Flightless I mRNA, an aptamer, and an agent that interacts with or binds to the Flightless I protein (or a regulator of Flightless I) and inhibits its activity, such as a drug, small molecule, protein, polypeptide or oligopeptide.

In one embodiment, the agent which decreases the expression and/or activity of Flightless I is a Flightless I binding protein. For example, the inventors have established that the Flightless I binding protein, FLAP-1, is capable of decreasing the level of Flightless I protein. However, it is to be understood that any Flightless I binding protein that can decrease the level and/or activity of the Flightless I protein is contemplated by the present invention.

FLAP-1 is also known as the Leucine Rich Repeat (in FLII) Interacting Protein 1 (LRRFIP1), LRR FLII-interacting protein, leucine-rich repeat flightless-interacting protein 1, FLAP1, FLIIAP1, GCF-2, GC-binding factor 2, HUFI-1, NEDD8-conjugating enzyme, and TAR RNA-interacting protein (TRIP), and is highly conserved across a number of species. The human FLAP-1 gene encodes five isoforms variants, the mRNA and amino acid sequences of which are set out in SEQ ID NOs: 7 to 16, and represented by GenBank Accession Numbers NM_001137550.1 and NP_001131022.1 (variant 1), NM_001137551.1 and NP_001131023.1 (variant 2), NM_001137552.1 and NP_001131024.1 (variant 3), NM_004735.3 and NP_004726.2 (variant 4), and NM_001137553.1 and NP_001131025.1 (variant 5). Further details of the FLAP-1 gene in human and other species may be accessed from the GenBank database at the National Centre for Biotechnology Information (NCBI) (ncbi.nlm.nih.gov). For example, the Gene ID number for human FLAP-1 is 9208.

Further details regarding the FLAP-1 gene in other species can be found at the UniGene portal of the NCBI (i.e. UniGene Hs. 471779. Alternatively, details of the nucleotide and amino acid sequence for FLAP-1 can be accessed from the UniProt database (uniprot.org) wherein the UniProt ID for human FLAP-I is Q9Y607 (variant 1), B4DPC0 (variant 2), and Q32MZ4 (variants 3 to 5). The contents of the GenBank and UniProt records are incorporated herein by reference.

In one embodiment, the agent which decreases the expression and/or activity of Flightless I is an antibody, or an antigen binding part thereof, to the Flightless I protein. As would be understood by a person skilled in the art, an "antibody" refers to a polypeptide comprising a framework region from an immunoglobulin gene or fragments thereof that specifically binds and recognizes an antigen, in this case the Flightless I protein. The recognised immunoglobulin genes include the kappa, lambda, alpha, gamma, delta, epsilon, and mu constant region genes, as well as the multitude of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

Naturally occurring immunoglobulins have a common core structure in which two identical light chains (about 24 kD) and two identical heavy chains (about 55 or 70 kD) form a tetramer. The amino-terminal portion of each chain is known as the variable (V) region and can be distinguished from the more conserved constant (C) regions of the remainder of each chain. Within the variable region of the light chain is a C-terminal portion known as the J region. Within the variable region of the heavy chain, there is a D region in addition to the J region. Most of the amino acid sequence variation in immunoglobulins is confined to three separate locations in the V regions known as hypervariable regions or complementarity determining regions (CDRs) which are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3, and FR4, respectively. The locations of CDR and FR regions and a numbering system have been defined for example by Kabat et al., 1991 (Sequences of Proteins of Immunological Interest, Fifth Edition, U.S. Department of Health and Human Services, U.S. Government Printing Office).

The term "antigen binding part" is to be understood to mean the antigen-binding portion of an antibody molecule, including a Fab, Fab', F(ab')$_2$, Fv, a single-chain antibody (scFv), a chimeric antibody, a diabody or any polypeptide that contains at least a portion of an immunoglobulin that is sufficient to confer specific antigen binding, such as a molecule including one or more CDRs (see further detail below).

Antibodies exist as intact immunoglobulins or as a number of well-characterized fragments produced by digestion with various peptidases. Therefore, for example, pepsin digests an antibody below the disulfide linkages in the hinge region to produce F(ab)'$_2$, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, a person skilled in the art would appreciate that such fragments may be synthesized de novo either chemically or by using recombinant DNA methodology. Therefore, the term antibody, as used herein, also includes antibody fragments either produced by the modification of whole antibodies, or those synthesized de novo using recombinant DNA methodologies (e.g. single chain Fv) or those identified using phage display libraries (see for example McCafferty et al., 1990, Nature 348:552-554).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g. an enzyme, toxin, hormone, growth factor, drug, etc.; or (b) the variable region, or a portion thereof, is altered, replaced or exchanged with a variable region having a different or altered antigen specificity. The chimeric antibodies may be monovalent, divalent, or polyvalent immunoglobulins. For example, a monovalent chimeric antibody is a dimer (HL) formed by a chimeric H chain associated through disulfide bridges with a chimeric L chain, as noted above. A divalent chimeric antibody is a tetramer (H$_2$ L$_2$) formed by two HL dimers associated through at least one disulfide bridge. A polyvalent chimeric antibody is based on an aggregation of chains.

In one embodiment, the antibody may be a humanised antibody. A "humanised" antibody is an antibody that retains the reactivity of a non-human antibody while being less immunogenic in humans. This can be achieved, for example, by retaining the non-human CDR regions and replacing the remaining parts of the antibody with their human counterparts. See for example Morrison et al., 1984, *Proc. Natl. Acad. Sci. USA*, 81: 6851-6855; Morrison and Oi, 1988, *Adv. Immunol.*, 44: 65-92; Verhoeyen et al., 1988, *Science*, 239: 1534-1536; Padlan, 1991, *Molec. Immun.*, 28: 489-498; and Padlan, 1994, *Molec. Immun.*, 31: 169-217.

In one embodiment, the antibody to Flightless I is a neutralising antibody. In one embodiment, the neutralising antibody binds specifically to the leucine rich repeat domain of the Flightless I protein. As would be understood by a person skilled in the art, a neutralising antibody is and antibody that can reduce or neutralise the expression and/or activity of Flightless I. Methods for producing antibodies, including neutralising antibodies, are as described below.

For the production of antibodies, various hosts including rabbits, rats, goats, mice, humans, and others may be immunised by injection with a Flightless I polypeptide or with any fragment, peptide or oligopeptide thereof which has immunogenic properties. Various adjuvants may be used to increase immunological response and include, but are not limited to, Freund's, mineral gels such as aluminum hydroxide, and surface-active substances such as lysolecithin. Adjuvants used in humans include BCG (bacilli Calmette-Guerin) and *Corynebacterium parvum*.

It is preferred that the Flightless I oligopeptides, peptides, or fragments used to induce antibodies have an amino acid sequence consisting of at least 5 amino acids, and, more preferably, of at least 10 amino acids of Flightless I. It is also preferable that these oligopeptides, peptides, or fragments are identical to a portion of the amino acid sequence of the natural protein and contain the entire amino acid sequence of a small, naturally occurring molecule. Short stretches of amino acids from Flightless I may be fused with those of another protein, such as KLH, and antibodies to the chimeric molecule may be produced.

Monoclonal antibodies to Flightless I may be prepared using any technique which provides for the production of antibody molecules by continuous cell lines in culture. These include, but are not limited to, the hybridoma technique, the human B-cell hybridoma technique, and the EBV-hybridoma technique (for example, see Kohler et al., 1975, *Nature* 256: 495-497; Kozbor et al., 1985, *J. Immunol. Methods* 81:31-42; Cote et al., 1983, *Proc. Natl. Acad. Sci. USA* 80: 2026-2030; and Cole et al., 1984, *Mol. Cell Biochem.* 62: 109-120).

Antibodies may also be produced by inducing in vivo production in the lymphocyte population or by screening immunoglobulin libraries or panels of highly specific binding reagents as disclosed in the literature (for example, see Orlandi et al., 1989, *Proc. Natl. Acad. Sci. USA* 86: 3833-3837; and Winter and Milstein, 1991, *Nature* 349: 293-299). Antibodies may also be generated using phage display. For example, functional antibody domains are displayed on the surface of phage particles that carry the polynucleotide sequences encoding them. Such phage can be utilized to display antigen-binding domains expressed from a repertoire or combinatorial antibody library (e.g. human or murine). Phage expressing an antigen binding domain that binds Flightless I can be selected or identified with Flightless I, e.g. using labeled Flightless I or a portion thereof. Phage used in these methods are typically filamentous phage including fd and MI 3 binding domains expressed from phage with Fab, Fv or disulfide stabilised Fv antibody domains recombinantly fused to either the phage gene III or gene VIII protein. Examples of phage display methods that can be used to make the antibodies may include those disclosed in Brinkman at al., 1995, *J. Immunol. Methods* 182: 41-50; Ames at al., 1995, *J. Immunol. Methods* 184: 177-186; Kettleborough et al., 1994, *Eur. J. Immunol.* 24: 952-958; Persic et al., 1997, *Gene* 187: 9-18; Burton et al., 1994, *Advances in Immunology* 57: 191-280; PCT application number PCT/GB91/01134; PCT publications numbers WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

Techniques which can be used to produce single-chain Fvs and antibodies include those described in U.S. Pat. Nos. 4,946,778 and 5,258,498; Huston et al., 1991, *Methods in Enzymology* 203: 46-88; Shu et al., 1993, *Proc. Natl. Acad. Sci. USA* 90: 7995-7999; and Skerra et al., 1988, *Science* 240: 1038-1040.

Antibody fragments which contain specific binding sites for Flightless I may be generated using standard techniques known in the art. For example, F(ab')2 fragments may be produced by pepsin digestion of a Flightless I antibody molecule and Fab fragments generated by reducing the disulfide bridges of the F(ab')2 fragments. Alternatively, Fab expression libraries may be constructed to allow rapid and easy identification of monoclonal Fab fragments with the desired specificity (for example, see Huse et al., 1989, *Science* 246: 1275-1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between a protein and its specific antibody. A two-site, monoclonal-based immunoassay utilising antibodies reactive to two non-interfering epitopes is preferred, but a competitive binding assay may also be employed.

In one embodiment, decreasing the expression and/or activity of Flightless I may be achieved by antisense or gene-targeted silencing strategies. Accordingly, such strategies utilise agents including antisense oligonucleotides, antisense RNA, antisense RNA expression vectors, small interfering RNAs (siRNA), microRNAs (miRNAs) and short hairpin RNAs (shRNAs). Still further, catalytic nucleic acid molecules such as aptamers, DNAzymes and ribozymes may be used for gene silencing. These molecules function by cleaving their target mRNA molecule rather than merely binding to it as in traditional antisense approaches.

An "antisense oligonucleotide" encompassed by the present invention corresponds to an RNA sequence as well as a DNA sequence coding therefor, which is sufficiently complementary to the Flightless I mRNA molecule, for which the antisense RNA is specific, to cause molecular hybridisation between the antisense RNA and the Flightless I mRNA such that translation of the mRNA is inhibited. Such hybridisation can occur under in vitro and in vivo conditions. The antisense molecule must have sufficient complementarity to Flightless I gene so that the antisense RNA can hybridize to the Flightless I gene (or mRNA) and inhibit its expression regardless of whether the action is at the level of splicing, transcription, or translation. In some embodiments, the complementary antisense sequence is about 15 to 30 nucleotides in length, for example, 15, 16, 17, 18, 19, 20, 21, 22, 23, 24, 25, 26, 27, 28, 29 or 30 nucleotides, or longer or shorter, as desired. Antisense oligonucleotides can include sequences hybridisable to any of several portions of the Flightless I gene, including the coding sequence, 3' or 5' untranslated regions, or intronic sequences.

The terms "small interfering RNA" and "siRNA" interchangeably refer to short double-stranded RNA oligonucleotides that mediate RNA interference (also referred to as "RNA-mediated interference," or RNAi). RNAi is a highly conserved gene silencing event functioning through targeted destruction of individual mRNA by a homologous double-stranded small interfering RNA (siRNA) (Fire, A et al., 1998, *Nature* 391: 806-811). Mechanisms for RNAi are reviewed, for example, in Bayne and Allshire, 2005, *Trends in Genetics*, 21: 370-73; Morris, 2005, *Cell Mol. Life Sci.*, 62: 3057-3066; and Filipowicz, et al., 2005, *Current Opinion in Structural Biology*, 15: 331-3341.

For the purposes of the present invention, RNAi can be effected by introduction or expression in the subject of siRNAs specific for Flightless I. The double stranded oligonucleotides used to effect inhibition of expression, at either the transcriptional or translational level, can be of any convenient length. siRNA molecules are typically from about 15 to about 30 nucleic acids in length, for example, about 19-25 nucleic acids in length, for example, about 15, 16, 17, 18, 19, 20, 21, 22, 23, 24, 25, 26, 27, 28, 29, 30 nucleic acids in length. Optionally the dsRNA oligonucleotides can include 3' overhang ends. Exemplary 2-nucleotide 3' overhangs can be composed of ribonucleotide residues of any type and can be composed of 2'-deoxythymidine resides, which lowers the cost of RNA synthesis and can enhance nuclease resistance of siRNAs in the cell culture medium and within transfected cells (see Elbashir et al., 2001, *Nature* 411: 494-498).

Longer dsRNAs of 50, 75, 100 or even 500 base pairs or more can also be utilised. Exemplary concentrations of dsRNAs for effecting Flightless I inhibition are about 0.05 nM, 0.1 nM, 0.5 nM, 1.0 nM, 1.5 nM, 25 nM or 100 nM, although other concentrations can be utilised depending upon the nature of the cells treated and other factors readily discernable to the skilled artisan.

Exemplary dsRNAs can be synthesized chemically or produced in vitro or in vivo using appropriate expression vectors. Exemplary synthetic RNAs include 21 nucleotide RNAs chemically synthesised using methods known in the art. Synthetic oligonucleotides are preferably deprotected and gel-purified using methods known in the art (see for example Elbashir et al., 2001, *Genes Dev.* 15: 188-200). Alternatively the dsRNAs can be transcribed from a mammalian expression vector. A single RNA target, placed in both possible orientations downstream of an appropriate promoter for use in mammalian cells, will transcribe both strands of the target to create a dsRNA oligonucleotide of the desired target sequence. Any of the above RNA species should be designed to include a portion of nucleic acid sequence represented in a target nucleic acid.

The specific sequence utilised in design of the siRNA oligonucleotides can be any contiguous sequence of nucleotides contained within the expressed gene message of the Flightless I target. Programs and algorithms, known in the art, may be used to select appropriate target sequences within the Flightless I gene (for example see the Ambion website at ambion.com). In addition, optimal sequences can be selected utilising programs designed to predict the secondary structure of a specified single stranded nucleic acid sequence and allow selection of those sequences likely to occur in exposed single stranded regions of a folded mRNA. Methods and compositions for designing appropriate siRNA oligonucleotides may be found, for example, in U.S. Pat. No. 6,251,588, the contents of which are incorporated herein by reference.

As would be understood by a person skilled in the art, ribozymes are enzymatic RNA molecules capable of catalyzing specific cleavage of RNA. The composition of a ribozyme molecule of the present invention should include one or more sequences complementary to Flightless I mRNA, and the well known catalytic sequence responsible for mRNA cleavage or a functionally equivalent sequence (see for example U.S. Pat. No. 5,093,246, which is incorporated herein by reference in its entirety). Ribozyme molecules designed to catalytically cleave Flightless I mRNA transcripts can also be used to prevent translation of Flightless I mRNA. While ribozymes that cleave mRNA at site-specific recognition sequences can be used to destroy target mRNAs, the use of hammerhead ribozymes is preferred. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art.

Flightless I targeting ribozymes of the present invention necessarily contain a hybridising region complementary to two regions, each of at least 5 and preferably each 6, 7, 8, 9, 10, 11, 12, 13, 14, 15, 16, 17, 18, 19 or 20 contiguous nucleotides in length, of the target Flightless I mRNA. In addition, the ribozymes should possess highly specific endoribonuclease activity, which autocatalytically cleaves the Flightless I sense mRNA.

With regard to antisense, siRNA or ribozyme oligonucleotides, phosphorothioate oligonucleotides can be used. Modifications of the phosphodiester linkage as well as of the heterocycle or the sugar may provide an increase in efficiency. Phophorothioate is used to modify the phosphodiester linkage. An N3'-P5' phosphoramidate linkage has been described as stabilising oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimisation as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and T-methoxyethoxy ribose modifications stabilize oligonucleotides to nucleases in cell culture and in vivo.

Inhibitory oligonucleotides can be delivered to a subject or the cell of a subject by direct transfection or transfection and expression via an expression vector. Appropriate expression vectors include mammalian expression vectors and viral vectors, into which has been cloned an inhibitory oligonucleotide with the appropriate regulatory sequences including a promoter to result in expression of the antisense RNA in a host cell. Suitable promoters can be constitutive or development-specific promoters. Transfection delivery can be achieved by liposomal transfection reagents, known in the art (e.g. Xtreme transfection reagent, Roche, Alameda, Calif.; Lipofectamine formulations, Invitrogen, Carlsbad, Calif.). Delivery mediated by cationic liposomes, by retroviral vectors and direct delivery are efficient. Another possible delivery mode is targeting using antibody to cell surface markers for the target cells.

The agent in the various embodiments of the present invention may also cause an alteration in the intracellular and/or extracellular localisation of Flightless I. For example, the agent may cause re-localisation of Flightless I from the cytoplasm of the cell to the nucleus of the cell, or re-localisation of Flightless I from the nucleus to the cytoplasm.

As indicated above, the Flightless I gene is evolutionary conserved across a number of species. Accordingly, the term "subject" as used in the present invention should be taken to encompass any subject which expresses the Flightless I gene. In some embodiments, the subject is a human or animal subject. The animal subject may be a mammal, a primate, a livestock animal (e.g. a horse, a cow, a sheep, a pig, or a goat), a companion animal (e.g. a dog, a cat), a laboratory test animal (e.g. a mouse, a rat, a guinea pig, a bird), an animal of veterinary significance, or an animal of economic significance.

As indicated above, the present invention provides a method of treating or preventing cancer in a subject. It is to be understood that the type of cancer that can be treated is not to be limited. In other words, any cancer that results from abnormal Flightless I expression and/or activity can be treated or prevented by the method of the first aspect of the invention. Examples of cancers include, but are not limited to, the group consisting of carcinoma, bladder cancer, bone cancer, brain cancer, breast cancer, cervical cancer, colorectal cancer including cancer of the colon, rectum, anus, and appendix, cancer of the oesophagus, Hodgkin's disease, kidney cancer, cancer of the larynx, leukaemia, liver cancer, lung cancer, lymphoma, multiple myeloma, muscular cancer, non-Hodgkin's lymphoma, oral cancer, ovarian cancer, cancer of the pancreas, prostate cancer, sarcoma, skin cancer, stomach cancer, testicular cancer, teratoma, thyroid cancer, and cancer of the uterus.

In one embodiment, the cancer is selected from the group consisting of skin cancer, colorectal cancer, and lung cancer. In one embodiment, the skin cancer is squamous cell carcinoma.

The present invention also provides use of an agent that decreases the expression and/or activity of Flightless I in the manufacture of a medicament for treating or preventing cancer in a subject.

In a second aspect, the present invention provides a method of inhibiting the growth of a cancerous cell, the method including the step of decreasing the expression and/or activity of Flightless I in the cell. In one embodiment, decreasing the expression and/or activity of Flightless I in the cell includes administration to the cell of an effective amount of an agent that decreases the expression and/or activity of Flightless I. Examples of suitable agents have been described in detail above. The meaning of "decreasing the expression and/or activity of Flightless I" has also been described in detail above with respect to the first aspect of the invention.

The method according to the second aspect of the invention can be practiced in an in vitro or in vivo setting. That is, the cancerous cell may be derived from a cancer cell line, may be derived from a tumour tissue biopsy sample taken from a subject with cancer, or may be a cell present in situ in a subject with cancer. In one embodiment, the cell is selected from the group consisting of a skin cell, a colon cell, and a lung cell. In one embodiment, the skin cell is a squamous cell.

The present invention also provides use of an agent that decreases the expression and/or activity of Flightless I in the manufacture of a medicament for inhibiting the growth of a cancerous cell.

In a third aspect, the present invention provides a method of inhibiting formation and/or growth of a tumour in a subject, or of inhibiting tumour invasion and metastasis in a subject, the method including the step of decreasing the expression and/or activity of Flightless I in the subject. In one embodiment, decreasing the expression and/or activity of Flightless I in the subject includes administration to the subject of an effective amount of an agent that decreases the expression and/or activity of Flightless I. Examples of suitable agents have been described in detail above. The meaning of "decreasing the expression and/or activity of Flightless I" has also been described in detail above with respect to the first aspect of the invention.

As would be understood by a person skilled in the art, "metastasis" is the process whereby tumour cells migrate throughout the body. In order for a tumour to produce metastases it must contain cells of the correct genotype and must be capable of completing a complex series of steps. The steps of tumour cell metastasis include the detachment of tumour cells from the primary neoplasm, invasion into the surrounding stroma, intravasation into the vasculature or lymphatic system, survival in the circulation, extravasation into the new host organ or tissue, and then survival and growth in this new microenvironment.

With respect to the third aspect of the invention, examples of tumours include, but are not limited to, the group consisting of bladder tumours, bone tumours, brain tumours, breast tumours, cervical tumours, colorectal tumours including tumours of the colon, rectum, anus, and appendix, tumours of the oesophagus, kidney tumours, tumours of the larynx, liver tumours, lung tumours, muscular tumours, oral tumours, ovarian tumours, tumours of the pancreas, prostate tumours, skin tumours, stomach tumours, testicular tumours, thyroid tumours, and tumours of the uterus.

In one embodiment, the tumour is selected from the group consisting of a skin tumour, a colorectal tumour, and a lung tumour. In one embodiment, the skin tumour is a squamous cell tumour.

The term "inhibiting" as used in the second and third aspects of the invention is taken to mean a decrease or reduction in the growth of a cancerous cell or tumour when compared to the growth in a control, such as an untreated cell or subject. In one embodiment, growth may be decreased or reduced by at least 10%, 20%, 30%, 40%, 50%, 60%, 70%, 80%, 90%, or 100%, relative to an untreated control.

Inhibition of the growth of a tumour or cancerous cell may be assessed by a range of methods known in the art. For example, for a cancerous cell in vitro, the growth of the cell may be determined by a suitable proliferation assay, or by a method which assess the extent of incorporation of tritiated thymidine into cellular DNA over a given period of time. For a tumour or cancerous cell present in vivo, the growth of the tumour or cell may be determined for example by a suitable imaging method known in the art.

The present invention also provides use of an agent that decreases the expression and/or activity of Flightless I in the manufacture of a medicament for inhibiting formation and/or growth of a tumour in a subject, or for inhibiting tumour invasion and metastasis in a subject.

As indicated above, the inventors have determined that the level of Flightless I protein is increased in cancer cells, and that overexpression of Flightless I in vivo leads to tumour development and progression. The differential expression of Flightless I indicates that it is a suitable biomarker which can form the basis of diagnostic and prognostic testing for cancer.

A biomarker is effectively an organic biomolecule which is differentially present in a sample taken from a subject of one phenotypic status (e.g. having a disease) as compared with another phenotypic status (e.g. not having the disease). A biomarker is differentially present between different phenotypic status groups if the mean or median expression level of the biomarker is calculated to be different (i.e. higher or lower) between the groups. Therefore, biomarkers, alone or in combination, provide an indication that a subject belongs to one phenotypic status or another.

Accordingly, in a fourth aspect, the present invention provides a method of diagnosing cancer in a subject, the method including the steps of:

measuring the level of expression and/or activity of Flightless I in the subject;

comparing the level of expression and/or activity of Flightless I in the subject to a reference level of expression and/or activity of Flightless I; and diagnosing cancer in the subject on the basis of the comparison.

Through the use of a genetically engineered mouse overexpressing Flightless I ($Flii^{Tg/Tg}$), the present inventors have determined that Flightless I plays a role in the development of squamous cell tumours.

Accordingly, in a fifth aspect, the present invention provides a method of determining if a subject is susceptible to developing cancer, the method including the steps of:

measuring the level of expression and/or activity of Flightless I in the subject;

comparing the level of expression and/or activity of Flightless I in the subject to a reference level of expression and/or activity of Flightless I; and determining if the subject is susceptible to developing cancer on the basis of the comparison.

The inventors have also established that decreasing expression of Flightless I leads to a decrese in tumour invasion and metastatis. Furthermore, the identification of differential expression of Flightless I in cancer also enables methods for assessing the therapeutic efficacy in a subject of a treatment for the cancer.

Accordingly, in a sixth aspect, the present invention provides a method of assessing progression of cancer in a subject, the method including the steps of:

measuring the level of expression and/or activity of Flightless I in the subject;

comparing the level of expression and/or activity of Flightless I in the subject to a reference level of expression and/or activity of Flightless I; and assessing the progression of cancer in the subject on the basis of the comparison.

Methods and assays which may be used to measure expression and/or activity of Flightless I (and the level thereof) have been described in detail above. The aforementioned methods and assays may measure the level of expression of Flightless I at the transcriptional (mRNA) or translational (protein) stage of expression.

In the subject, the level of expression and/or activity of Flightless I may be measured directly, or in an alternative embodiment, the level of expression and/or activity of Flightless I may be measured in a sample obtained from a subject. It is to be made clear that the sample obtained from the subject that is analysed by the methods of the present invention may have previously been obtained from the subject, and, for example, stored in an appropriate repository. In this instance, the sample would have been obtained from the subject in isolation of, and therefore separate to, the methods of the present invention.

The sample which is obtained from the subject may include, but is not limited to, a tissue or tumour biopsy sample, including a corresponding normal tissue sample, blood sample, or a sample derived from blood (for example a serum sample or a plasma sample or a fraction of a blood, serum or plasma sample, blood cells), skin, saliva, buccal swab, stool sample, bladder washing, semen, and urine. In certain circumstances, the sample may be manipulated in any way after procurement, such as by treatment with reagents, solubilization, or enrichment for certain components, such as the relevant protein or polynucleotide under investigation.

Once the level of expression and/or activity of Flightless I been measured in the subject, or in a sample obtained from the subject, the level of expression and/or activity is compared to a reference level of expression and/or activity for Flightless I. The reference level of expression and/or activity for Flightless I is a level of expression and/or activity that is associated with a known cancer status, i.e. a level of expression and/or activity which is known to be found in a subject not suffering from cancer (a "normal" subject in the context of the present invention). A reference level of expression and/or activity of Flightless I may be derived from at least one normal subject and is preferably derived from an average of normal subjects (e.g. n=2 to 100 or more), wherein the subject or subjects have no prior history of cancer. A reference level of expression and/or activity of Flightless I can also be obtained from one or more normal samples from a subject suspected to have cancer. For example, a reference level of expression and/or activity of Flightless I may be obtained from at least one normal sample and is preferably obtained from an average of normal samples (e.g. n=2 to 100 or more) from the subject.

As indicated above, the inventors have found that the level of expression of Flightless I is increased in cancer cells and tumours. Accordingly, in an embodiment of the fourth, fifth and sixth aspects of the invention, a level of expression and/or activity of Flightless I in the subject that is higher than the reference level of expression and/or activity for Flightless I is indicative of cancer in the subject, indicates that the subject is susceptible to cancer, or is indicative of the progression of cancer in the subject.

In some embodiments of the present invention, a level of expression and/or activity of Flightless I is measured at more than one time points. Such "serial" sampling is well suited, for example, to monitoring the progression of cancer. Serial sampling can be performed for any desired timeline, such as monthly, quarterly (i.e. every three months), semi-annually, annually, biennially, or less frequently. The comparison between the measured expression level in the subject and the reference expression level may be carried out each time a new sample is measured, or the data relating to levels may be held for less frequent analysis.

In one embodiment of the sixth aspect of the invention, the subject is undergoing treatment for the cancer. The treatment may be a conventional therapy such as chemotherapy or radiotherapy, or the treatment may be an alternative therapy. In an alternative embodiment, the subject may not be undergoing treatment at all.

In some embodiments, the method according to the sixth aspect of the invention may be used to perform clinical trials of a new drug, as well as to monitor the progress of a subject on the drug. Therapy or clinical trials involve administering the drug being tested in a particular regimen. The regimen may involve a single dose of the drug or multiple doses of the drug over time. The doctor or clinical researcher monitors the effect of the drug on the subject over the course of administration. If the drug has a pharmacological impact on the cancer, the level of expression and/or activity of Flightless I will approximate or be identical to the reference level of expression and/or activity of Flightless I. Therefore, the trending of the expression and/or activity levels of Flightless I can be monitored in the subject during the course of treatment. The level of expression and/or activity of Flightless I can be determined using the methods described in detail above. One embodiment of this method involves determining the level of expression and/or activity of Flightless I for at least two different time points during a course of drug therapy, e.g. a first time and a second time, and comparing the change in expression and/or activity level over that time, if any. For example, the level of expression and/or activity of Flightless I can be measured before and after drug administration or at two different time points during drug administration. The effect of therapy is determined based on these comparisons. If a treatment is effective, the level of expression and/or activity of Flightless I will approximate or be identical to the reference level of expression and/or activity of Flightless I, while if treatment is ineffective, the level of expression and/or activity of Flightless I will remain higher than the reference level.

In a seventh aspect, the present invention provides a method of screening for a candidate therapeutic agent useful for treating or preventing cancer in a subject, the method including the step of assaying the candidate therapeutic agent for activity in decreasing the level of expression and/or activity of Flightless I, wherein an agent that decreases the level of expression and/or activity of Flightless I is a candidate therapeutic agent useful for treating or preventing cancer in the subject. Examples of suitable agents to screen are as described above.

Screening assays may be performed in vitro and/or in vivo. For example, prospective agents may be screened to identify candidate therapeutic agents for the treatment of cancer in a cell-based assay. In this regard, each prospective agent is incubated with cultured cells (for example cells obtained from a tumour of a subject suffering from cancer, cells obtained from a normal non-affected subject, from normal tissue of a subject suffering from cancer, or from cell lines derived from a normal or affected subject), and modulation of the level of expression and/or activity of Flightless I is measured. In another example, candidate therapeutic agents may be screened in organ culture-based assays. In this regard, each prospective agent is incubated with either a whole organ or a portion of an organ derived from a non-human animal and modulation of the level of expression and/or activity of Flightless I is measured.

Screening methods may also employ administering prospective therapeutic agents to a subject suffering from cancer. Accordingly, in one embodiment, the method includes measuring a level of expression and/or activity of Flightless I in the subject, wherein the level of expression and/or activity is measured after administration of the candidate therapeutic agent to the subject. The level of expression and/or activity of Flightless I in the subject is then compared to a reference level of expression and/or activity of Flightless I. If the level of expression and/or activity of Flightless I in the subject approximates or is identical to the reference level of expression and/or activity of Flightless I, the candidate therapeutic agent can be said to be useful for the treatment of cancer. The level of expression and/or activity of Flightless I may be measured by the methods described in detail above.

The methods of the aforementioned aspects of the invention require the level of expression and/or activity of Flightless I to be measured. However, it would be well understood by a person skilled in the art that the level of expression and/or activity of other biomarkers may be measured in addition or concurrently with Flightless I. For example, biomarkers which are known to be differentially expressed in cancer can also be incorporated into the methods of the invention.

In an eighth aspect, the present invention provides a pharmaceutical composition when used for treating or preventing cancer in a subject, the composition including an effective amount of an agent that decreases expression and/or activity of Flightless I. Examples of suitable agents have been described in detail above. The meaning of "decreasing the expression and/or activity of Flightless I" has also been described in detail above with respect to the first aspect of the invention. Furthermore, the nature of the cancer has also been described in detail above.

The delivery or administration of the agent in the various embodiments of the present invention may be delivery or administration of the agent alone, or delivery or administration of the agent formulated into a suitable pharmaceutical composition, as referred to above.

In this regard, the pharmaceutical composition may also include the use of one or more pharmaceutically acceptable additives, including pharmaceutically acceptable salts, amino acids, polypeptides, polymers, solvents, buffers, excipients and bulking agents, taking into consideration the particular physical and chemical characteristics of the agent to be administered.

The preparation of such pharmaceutical compositions is known in the art, for example as described in Remington's Pharmaceutical Sciences, 18th ed., 1990, Mack Publishing Co., Easton, Pa. and U.S. Pharmacopeia: National Formulary, 1984, Mack Publishing Company, Easton, Pa.

For example, the agent can be prepared into a variety of pharmaceutical compositions in the form of, for example, an aqueous solution, an oily preparation, a fatty emulsion, an emulsion, a gel, etc., and these preparations can be administered as intramuscular or subcutaneous injection or as injection to an organ, or as an embedded preparation or as a transmucosal preparation through nasal cavity, rectum, uterus, vagina, lung, etc. The composition may be administered in the form of oral preparations (for example solid preparations such as tablets, capsules, granules or powders; liquid preparations such as syrup, emulsions or suspensions). Compositions containing the agent may also contain a preservative, stabiliser, dispersing agent, pH controller or isotonic agent. Examples of suitable preservatives are glycerin, propylene glycol, phenol or benzyl alcohol. Examples of suitable stabilisers are dextran, gelatin, a-tocopherol acetate or alpha-thioglycerin. Examples of suitable dispersing agents include polyoxyethylene (20), sorbitan monooleate (Tween 80), sorbitan sesquioleate (Span 30), polyoxyethylene (160) polyoxypropylene (30) glycol (Pluronic F68) or polyoxyethylene hydrogenated castor oil 60. Examples of suitable pH controllers include hydrochloric acid, sodium hydroxide and the like. Examples of suitable isotonic agents are glucose, D-sorbitol or D-mannitol.

The administration of the agent in the various embodiments of the present invention may also be in the form of a composition containing a pharmaceutically acceptable carrier, diluent, excipient, suspending agent, lubricating agent, adjuvant, vehicle, delivery system, emulsifier, disintegrant, absorbent, preservative, surfactant, colorant, flavorant or sweetener, taking into account the physical and chemical properties of the agent being administered.

For these purposes, the composition may be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term parenteral as used herein includes subcutaneous, intravenous, intramuscular, intraperitoneal, intrathecal, intraventricular, intrasternal, and intracranial injection or infusion techniques.

When administered parenterally, the composition will normally be in a unit dosage, sterile injectable form (solution, suspension or emulsion) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic parenterally-acceptable diluents or solvents, for example, as solutions in 1,3-butanediol. Among the acceptable vehicles and solvents that may be employed are water, saline, Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

The carrier may contain minor amounts of additives, such as substances that enhance solubility, isotonicity, and chemical stability, for example anti-oxidants, buffers and preservatives.

When administered orally, the agent will usually be formulated into unit dosage forms such as tablets, cachets, powder, granules, beads, chewable lozenges, capsules, liquids, aqueous suspensions or solutions, or similar dosage forms, using conventional equipment and techniques known in the art. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

A tablet may be made by compressing or moulding the agent optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Moulded tablets may be made by moulding in a suitable machine, a mixture of the powdered active ingredient and a suitable carrier moistened with an inert liquid diluent.

The administration of the agent in the various embodiments of the present invention may also utilise controlled release technology. The agent may also be administered as a sustained-release pharmaceutical. To further increase the sustained release effect, the agent may be formulated with additional components such as vegetable oil (for example soybean oil, sesame oil, camellia oil, castor oil, peanut oil, rape seed oil); middle fatty acid triglycerides; fatty acid esters such as ethyl oleate; polysiloxane derivatives; alternatively, water-soluble high molecular weight compounds such as hyaluronic acid or salts thereof (weight average molecular weight: ca. 80,000 to 2,000,000), carboxymethylcellulose sodium (weight average molecular weight: ca. 20,000 to 400,000), hydroxypropylcellulose (viscosity in 2% aqueous solution: 3 to 4,000 cps), atherocollagen (weight average molecular weight: ca. 300,000), polyethylene glycol (weight average molecular weight: ca. 400 to 20,000), polyethylene oxide (weight average molecular weight: ca. 100,000 to 9,000,000), hydroxypropylmethylcellulose (viscosity in 1% aqueous solution: 4 to 100,000 cSt), methylcellulose (viscosity in 2% aqueous solution: 15 to 8,000 cSt), polyvinyl alcohol (viscosity: 2 to 100 cSt), polyvinylpyrrolidone (weight average molecular weight: 25,000 to 1,200,000).

Alternatively, the agent may be incorporated into a hydrophobic polymer matrix for controlled release over a period of days. The agent may then be moulded into a solid implant, or externally applied patch, suitable for providing efficacious concentrations of the agent over a prolonged period of time without the need for frequent re-dosing. Such controlled release films are well known to the art. Other examples of polymers commonly employed for this purpose that may be used include nondegradable ethylene-vinyl acetate copolymer a degradable lactic acid-glycolic acid copolymers which may be used externally or internally. Certain hydrogels such as poly(hydroxyethylmethacrylate) or poly(vinylalcohol) also may be useful, but for shorter release cycles than the other polymer release systems, such as those mentioned above.

The carrier may also be a solid biodegradable polymer or mixture of biodegradable polymers with appropriate time release characteristics and release kinetics. The agent may then be moulded into a solid implant suitable for providing efficacious concentrations of the agent over a prolonged period of time without the need for frequent re-dosing. The agent can be incorporated into the biodegradable polymer or polymer mixture in any suitable manner known to one of ordinary skill in the art and may form a homogeneous matrix with the biodegradable polymer, or may be encapsulated in some way within the polymer, or may be moulded into a solid implant.

For topical administration, the composition of the present invention may be in the form of a solution, spray, lotion, cream (for example a non-ionic cream), gel, paste or ointment. Alternatively, the composition may be delivered via a liposome, nanosome, or nutri-diffuser vehicle.

A cream is a formulation that contains water and oil and is stabilized with an emulsifier. Lipophilic creams are called water-in-oil emulsions, and hydrophilic creams oil-in-water emulsions. The cream base for water-in-oil emulsions are normally absorption bases such as vaseline, ceresin or lanolin. The bases for oil-in-water emulsions are mono-, di-, and tri-glycerides of fatty acids or fatty alcohols with soaps, alkyl sulphates or alkyl polyglycol ethers as emulsifiers.

A lotion is an opaque, thin, non-greasy emulsion liquid dosage form for external application to the skin, which generally contains a water-based vehicle with greater than 50% of volatiles and sufficiently low viscosity that it may be delivered by pouring. Lotions are usually hydrophilic, and contain greater than 50% of volatiles as measured by LOD (loss on drying). A lotion tends to evaporate rapidly with a cooling sensation when rubbed onto the skin.

A paste is an opaque or translucent, viscous, greasy emulsion or suspension semisolid dosage form for external application to the skin, which generally contains greater than 50% of hydrocarbon-based or a polyethylene glycol-based vehicle and less than 20% of volatiles. A paste contains a large proportion (20-50%) of dispersed solids in a fatty or aqueous vehicle. An ointment tends not to evaporate or be absorbed when rubbed onto the skin.

An ointment is an opaque or translucent, viscous, greasy emulsion or suspension semisolid dosage form for external application to the skin, which generally contains greater than 50% of hydrocarbon-based or a polyethylene glycol-based vehicle and less than 20% of volatiles. An ointment is usually lipophilic, and contains >50% of hydrocarbons or polyethylene glycols as the vehicle and <20% of volatiles as measured by LOD. An ointment tends not to evaporate or be absorbed when rubbed onto the skin.

A gel is usually a translucent, non-greasy emulsion or suspension semisolid dosage form for external application to the skin, which contains a gelling agent in quantities sufficient to impart a three-dimensional, cross-linked matrix. A gel is usually hydrophilic, and contains sufficient quantities of a gelling agent such as starch, cellulose derivatives, carbomers, magnesium-aluminum silicates, xanthan gum, colloidal silica, aluminium or zinc soaps.

The composition for topical administration may further include drying agents, anti-foaming agents; buffers, neutralizing agents, agents to adjust pH; colouring agents and decolouring agents; emollients; emulsifying agents, emulsion stabilizers and viscosity builders; humectants; odorants; preservatives, antioxidants, and chemical stabilizers; solvents; and thickening, stiffening, and suspending agents, and a balance of water or solvent.

It should also be appreciated that other methods of delivery of an agent to modulate the expression and/or activity of Flightless I are contemplated. For example, the agent may be delivered by way of a nucleic acid or vector that allows for expression of the agent in the appropriate target cells. For example, the agent may be delivered by way of a viral vector that causes expression of the agent in target cells.

In a ninth aspect, the present invention provides a kit for diagnosing cancer in a subject, determining if a subject is susceptible to developing cancer, or assessing progression of cancer in a subject, the kit including means for measuring the level of expression and/or activity of Flightless I in the subject.

In one embodiment, a level of expression and/or activity of Flightless I in the subject that is higher than a reference level of expression and/or activity for Flightless I diagnoses cancer in the subject, is indicative that the subject is susceptible to developing cancer, or is indicative of progression of cancer in the subject.

Means and methods for measuring the level of expression and/or activity of Flightless I in the subject according to the ninth aspect of the invention are described in detail above.

In one embodiment, the kit includes a solid support, such as a chip, sensor, a microtiter plate or a bead or resin having a capture reagent attached thereon, wherein the capture reagent binds Flightless I. Therefore, for example, a kit of the present invention can comprise mass spectrometry probes for SELDI, such as ProteinChip® arrays, or a versatile fibre-based SPR sensing device. In the case of biospecfic capture reagents, the kit can comprise a solid support with a reactive surface, and a container comprising the biospecific capture reagent.

In one embodiment, the kit can also include a washing solution or instructions for making a washing solution, in which the combination of the capture reagent and the washing solution allows capture of Flightless I on the solid support for subsequent detection by, for example, mass spectrometry. The kit may include more than one type of adsorbent, each present on a different solid support.

In some embodiments, such a kit can include instructions for suitable operational parameters in the form of a label or separate insert. For example, the instructions may inform a consumer about how to collect the sample, how to wash the probe or the Flightless I to be detected.

In some embodiments, the kit can include one or more containers with samples that represent a reference expression level for Flightless I, and are therefore to be used as a standard for calibration.

It is to be noted that where a range of values is expressed, it will be clearly understood that this range encompasses the upper and lower limits of the range, and all values in between these limits.

Furthermore, the term "about" as used in the specification means approximately or nearly and in the context of a numerical value or range set forth herein is meant to encompass variations of +/−10% or less, +/−5% or less, +/−1% or less, or +/−0.1% or less of and from the numerical value or range recited or claimed.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

Finally, reference is made to standard textbooks of molecular biology that contain methods for carrying out basic techniques encompassed by the present invention, including DNA restriction and ligation for the generation of the various genetic constructs described herein. See, for example, Sambrook and Russell, *Molecular Cloning: A Laboratory Manual* (3rd edition), Cold Spring Harbor Laboratory Press, 2001.

The invention is further illustrated in the following examples. The examples are for the purpose of describing particular embodiments only and are not intended to be limiting with respect to the above description.

EXAMPLE 1

Flightless I Expression in Melanoma Cell Lines

Epithelial-mesenchymal transition of tumour cells followed by differentiation, invasion, adhesion and migration are crucial in understanding tumour development and progression as well as development of novel therapies. One cytoskeletal protein important in mediating cellular responses is Flightless I. Through its bipartite domain structure, Flightless I is uniquely able to interact with numerous structural and signalling proteins and transduce cell signalling events into a cytoskeleton remodelling, hence linking the signalling pathways with the actin cytoskeleton.

Considering the role of Flightless I in cellular processes, a number of melanoma cell lines were screened for expression of Flightless I protein. Briefly, human melanoma cell lines NM39, NM170, NM176 and SK-MEL28 were cultured in DMEM:Ham's F12 (3:1) supplemented with 10% FCS, 1% L-glutamine (200 mM) and Ready Mix Plus (0.4 µg/ml hydrocortisone, 5 µg/ml insulin, 10 ng/ml EGF, 5 µg/ml transferrin, 8.4 ng/ml cholera toxin and 13 ng/ml liothyronine).

Protein lysates from the melanoma cell cultures were prepared and were run following a standard Western Blotting procedure. Protein amounts in each sample were equalised by dilution and heated at 95'C prior to electrophoresis. Protein fractions were run on a 10% SDS-PAGE (sodium dodecyl sulfate/polyacrylamide) gel consisting of a 10% separating solution (3.35 ml 30% Acrylamide-Bis solution (37.5:1, 2.6% C, BioRad Laboratories, CA, USA), 1.25 ml 3M Tris pH 8.9, 5.25 ml distilled water, 125 µl 10% SDS, 100 µl 10% APS (Ammonium Per-sulfate)(Sigma-Aldrich Chemical Company, Sydney, Australia) and 6.25 µl TEMED (N,N,N',N'-Tetramethylethylene-diamine)(Sigma-Aldrich Chemical Company, Sydney, Australia) and 4% stacking solution (0.5 ml 30% Acrylamide, 0.276 ml 0.5M Tris pH 6.8, 4.104 ml distilled water, 50 µl 10% SDS, 40 µl 10% APS and 4 µl TEMED). Protein fractions were run at 100V for 90 min in the electrophoresis tank. The gel was then transferred onto a 0.2 µm pore nitrocellulose membrane (Advantec MFS Inc, CA, USA) by the process of Wet Transfer using the Bio-Rad Mini-ProteanII Transfer Apparatus (Bio-Rad Laboratories, NSW, Australia) and 1× Wet Transfer Buffer—Tobins Buffer (3.3 g Tris, 14.4 g Glycine, 900 ml MilliQ Water, 100 ml Methanol) at 100V for 1 hr. Proteins were then stained in Ponceau Red Stain (Sigma-Aldrich, Sydney, Australia) for 10 min and then destained in MilliQ water and washed in PBS Tween (0.3% Tween/PBS) (50 ml 20×PBS, 3 ml Tween, 947 ml MilliQ water). The gel was subjected to Coomassie Staining (Sigma-Aldrich, Sydney, Australia) for 30 min and destained in 40% Methanol, 10% Acetic Acid and 50% MilliQ water overnight to check for the transfer efficiency.

Membranes were then blocked in 5% skimmed milk in 0.3% Tween/PBS for 1 hr and hybridised with appropriate primary antibody at 1 µg/ml concentration, diluted in blocking buffer prior to addition to the membrane overnight at 4° C. Flightless I anti-rabbit antibodies (sc-30046) were purchased from Santa Cruz Biotechnology (CA, USA), and β-tubulin anti-mouse antibodies (T4026) were purchased from Sigma Aldrich. After blocking, membranes were washed in 5% skim milk, 0.3% Tween/PBS blocking buffer (4×10 min), and appropriate secondary antibody conjugated to horse radish peroxidise (HRP) at 1 µg/ml diluted in blocking buffer was applied to membranes in the dark for 1 hr at room temperature. The HRP secondary antibodies used (HRP-conjugated anti-mouse IgG—2017-10 and HRP-conjugated anti-rabbit IgG—2018-05) were obtained from Dako Cytomotion. This was followed by further membrane washes of 4×10 min in 0.3% Tween/PBS and signal detection using Super Signal West Femto Maximum Sensitivity Substrate (Pierce Biotechnology, Rockford, USA) and signal capture using GeneSnap analysis software program (Syngene, Md., USA). Membranes were stripped by incubation in Stripping Buffer (5 ml 20% SDS, 350 µl 2-Mercaptoethanol (#M7522, Sigma-Aldrich, Sydney, Australia), 6.25 ml 0.5 M Tris/HCl pH 6.7, 38.4 ml MilliQ Water) for 30 min with gentle shaking every 10 min followed by re-probing of membranes with 3-tubulin (Sigma-Aldrich, Sydney, Australia) as a loading/transfer control.

Results of these experiments are shown in FIG. 1. Flightless I is expressed in all melanoma cell lines tested suggesting a potential role for Flightless I in modulating cellular responses during development of melanoma, the most common skin cancer in Australia.

EXAMPLE 2

Analysis of Chemically-Induced Squamous Cell Carcinoma in Flightless I Transgenic Mice Using a well described model of chemically induced squamous cell carcinoma (SCC) in mice (a model that results in a 100% incidence of tumours—60% SCC, 40% sarcoma), including Flightless I transgenic mice, the effect of decreased, normal or increased Flightless I levels on development of primary SCC in vivo was investigated. SCC was induced in mice heterozygous for Flightless I (i.e. mice expressing a single copy of Flightless I-Flii$^{+/-}$) wild type mice (i.e. mice expressing both copies of Flightless I—WT), and transgenic mice overexpressing Flightless I (i.e. mice expressing extra copies of Flightless I—Flii$^{Tg/Tg}$) (n=12) following a single intradermal injection at right flank with 0.1 ml corn oil containing 500 µg of 3-Methylcholanthrene (MCA). The mice were monitored twice weekly for the development of primary tumours including taking photographs of tumours, measuring tumour volume using electronic callipers and clinically scoring the tumour development progression. At end of a 12 week period, mice were euthanized using $CO_2$ and cervical dislocation and tumour samples collected for histological analysis and cytokeratin staining to confirm tumour identification as SCC.

Preparation for histological analysis involved fixing the tumour samples in 10% formalin overnight, followed by processing in a Leica TP1020 tissue processor which dehydrated the tissues in a graded alcohol series (70% for 120 mins, 80% for 60 mins, 90% for 105 mins and 100% for 240 mins). They were then cleared in transitional solvent xylene for 180 mins followed by 240 mins of tissue infiltration with paraffin wax. Tissue sections (4 µm) were cut from paraffin-embedded fixed tissue using a Leica RM2235 microtome. Prior to staining, tissue sections were dewaxed by a series of xylene (30 mins) and graduated ethanol washes (bringing sections to water) (100% for 1 min, 70% for 1 min and 30% for 1 min) before further processing. Tissue sections were stained with Haematoxylin and Eosin (H&E). Staining the sections in H&E involved bringing sections to water as mentioned above, followed by staining in Lillie's-Mayer's Haematoxylin for 6 min, "blueing" sections in bicarbonate water for 15 sec, differentiating Haematoxylin in 0.25% Acid Alcohol for 6 sec, staining in alcohol based Eosin stain for 2 min, dehydrating in grated alcohol series (30% for 30 sec, 70% for 30 sec, 100% for 1 min) and clearing in transitional solvent xylene for 2 min before mounting in DePeX mounting medium. H&E stained tissue was examined histologically for the tumour morphology and presence of metastatic nodules.

Figure 2:
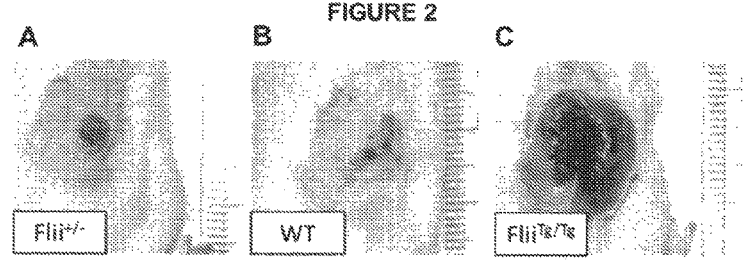
FIG. 2—images of chemically induced squamous cell carcinoma (SCC) development in Flightless I genetic mice. A: mice heterozygous for Flightless I (Flii$^{+/-}$); B: wild type mice (WT); and C: transgenic mice overexpressing Flightless I (Flii$^{Tg/Tg}$).
Figure 3:
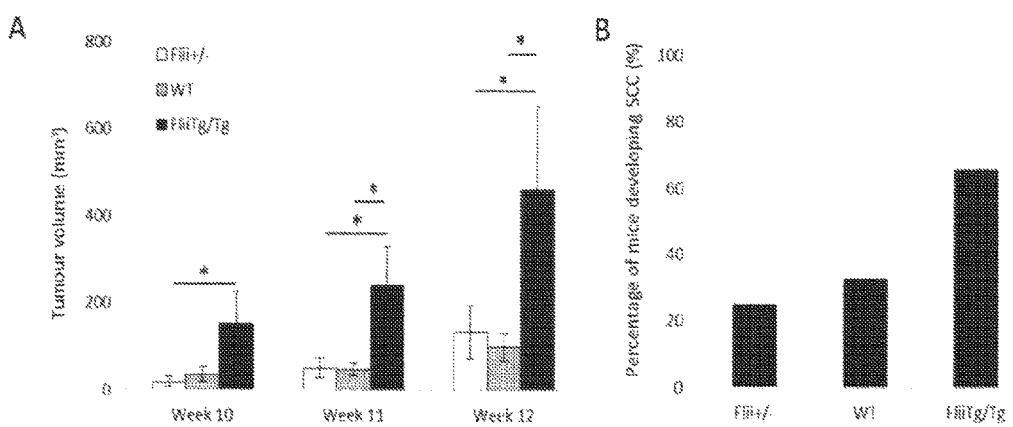
FIG. 3—graphs depicting characteristics of SCC tumour development in Flii$^{+/-}$, WT, and Flii$^{Tg/Tg}$ mice. A: tumour volume at weeks 10, 11 and 12 post chemical inducement; B: percentage of mice developing SSC tumours in each of the Flii$^{+/-}$, WT, and Flii$^{Tg/Tg}$ groups.
Figure 4:
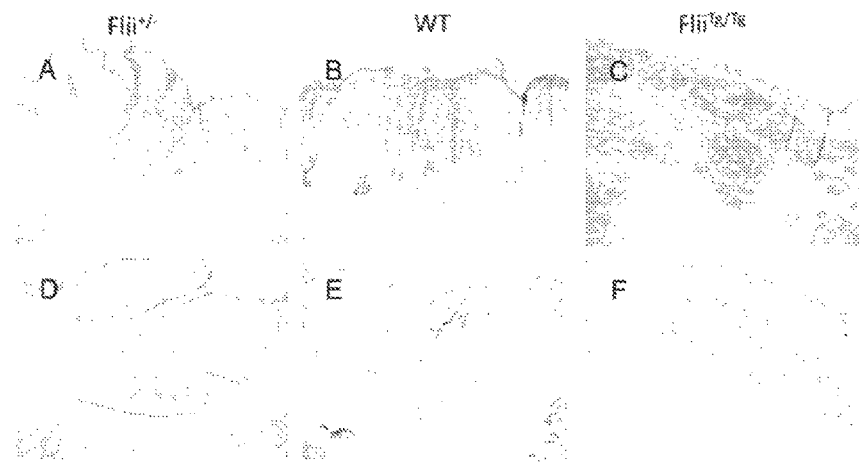
FIG. 4—representative images of SCC tumour development in Flii$^{+/-}$ (panels A and D), WT (panels B and E), and Flii$^{Tg/Tg}$ (panels C and F) mice at low magnification (×4), illustrating histological features of SCC in each of the three groups of mice.

Results show that compared to both Flii$^{+/-}$ and WT mice, a higher percentage of Flii$^{Tg/Tg}$ mice developed cancerous SCC lesions and these tumours appeared more severe, ulcerated and necrotic (see representative images in FIG. 2). This indicates that Flightless I may directly affect cancer progression. Increased levels of Flightless I also result in development of macroscopically larger SCC tumours (FIG. 3A) and higher incidence of tumours (FIG. 3B). Histological examination showed more invasive well differentiated invading SCC tumours in Flightless I overexpressing mice (FIG. 4). Specifically, compared to the SCC lesions observed in Flii$^{+/-}$ and WT mice illustrating epidermal hyperplasia and ulcerative lesions, tumours in Flii$^{Tg/Tg}$ mice appear well differentiated and more invasive with spate clusters of tumour cells and keratin pearls invading deep into the dermis (n=12). These results indicate that Flightless I not only plays an important role in SCC development but may directly influence the progression of tumour growth.

Figure 5:
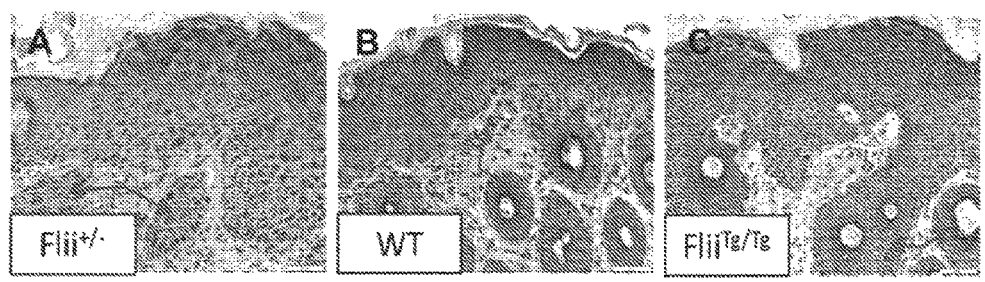
FIG. 5—representative images of SCC tumour development in A: Flii$^{+/-}$, B: WT, and C: Flii$^{Tg/Tg}$ mice illustrating epithelial origin of SCC tumors in all three genotypes (arrow). Magnification ×20. n=12. Scale bar =50 µm.
Figure 6:
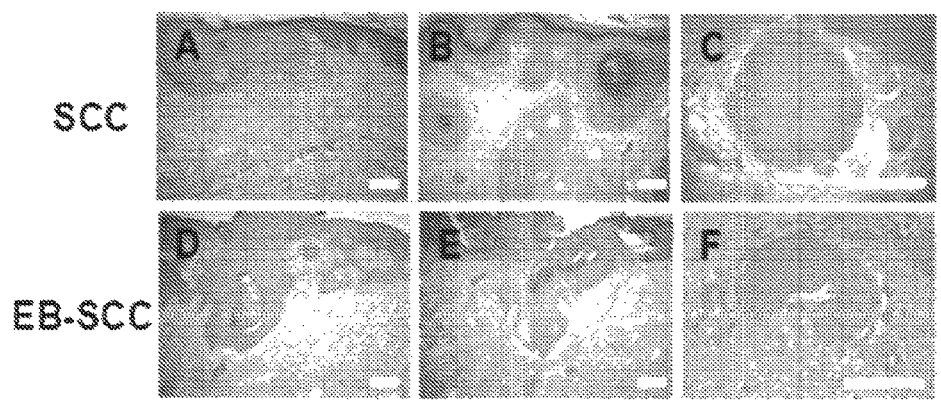
FIG. 6—histological representations of SCC (panels A to C) and Epidermal Bullosa-SCC (EB-SCC—panels D to F) tumours.
Figure 7:
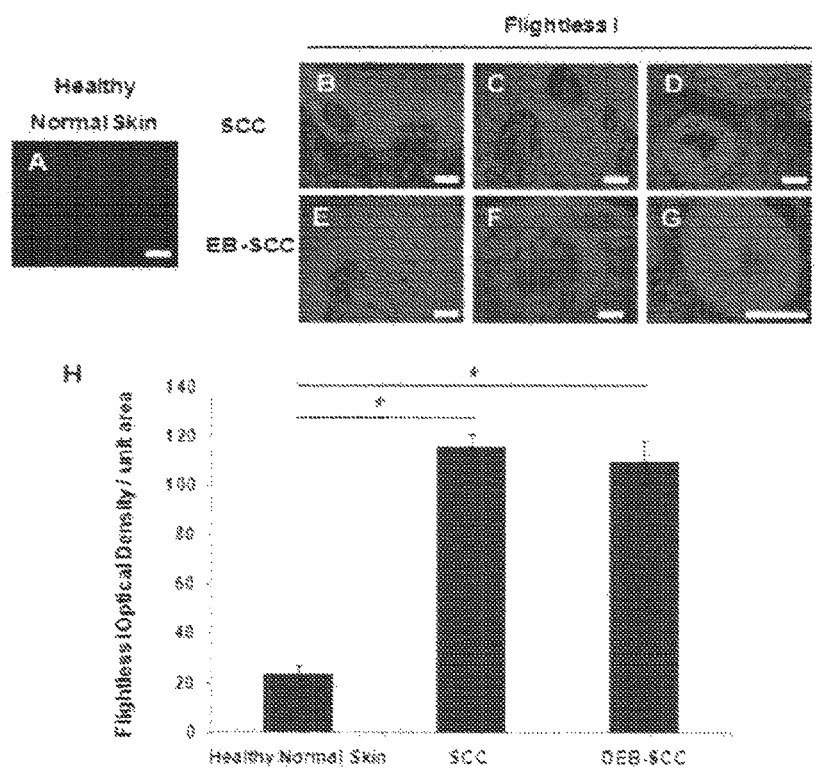
FIG. 7—representative images of the expression characteristics of Flightless I protein in normal healthy skin (panel A), SCC lesions of otherwise healthy patients (panels B to D) and SCC lesions from Epidemal Bullosa patients (EB-SCC—panels E to G). Panel H is a graphical analysis of the results represented in panels A to G.

The origin of SCC tumours in all three genotypes was also examined using pan-cytokeratin staining of invading epidermal cells. Briefly, pan-cytokeratin staining was performed on paraffin embedded SCC tumours of Flii$^{+/-}$, wild-type and Flii$^{Tg/Tg}$ mice. Sections were first quenched for the endogenous peroxidase activity with 0.3% hydrogen peroxide/methanol for 20 min on ice before blocking the non-specific activity using 3% normal goat serum in PBS for 30 min. Primary antibody goat anti-mouse cytokeratin (Adellab) was applied at a 1:100 dilution in 3% normal goat serum/PBS overnight at 4 degrees. Following 3×2 min washes with PBS, species specific biotinylated secondary antibody (Vector Laboratories, CA, USA) was applied at a 1:200 dilution in PBS for 1 hr. This was followed by further 3×2 min washes in PBS and application of Vectastain ABC kit following manufacturer's instructions. Following the formation of the Avidin-enzyme complex, sections were washed 3×2 min in PBS and Vector DAB (3,3'-diaminobenzidine) substrate kit was applied as per manufacturer's instructions. Sections were counterstained using standard haematoxylin staining for 6 min. Sections were examined using light microscopy for confirmation of cytokeratin positive brown cells of epithelial origin invading the deep dermis. Results are shown in FIG. 5 confirming the epithelial origin of SCC tumours in all three genotypes.

EXAMPLE 3

Flightless I Expression in Skin, Serum and Flightless I Transgenic Mice

Squamous Cell Carcinoma (SCC) is a particular problem in patients suffering from Epidermolysis bullosa (EB), a skin blistering condition. A 20 year study of EB patients in USA has shown that the cumulative risk of developing SCC and subsequent death in patients with generalized severe Recessive Dystrophic EB (RDEB) at age 55 is greater than 90% and 78% respectively (South A P and O'Toole E A, 2010, *Dermatol. Clin.*, 28: 171-178). In addition, children with RDEB have an increased risk of developing SCC (2.5% by age 12 vs. 1.35-2.7% lifetime risk in general population) (Fine J D et al., 2009, *J. Am. Acad. Dermatol.*, 60: 203-211).

The histological features between SCC and EB-SCC were examined. Human SCC and EB-SCC samples were obtained and fixed, stained and examined as described in Example 2. The results show that patients suffering from RDEB (n=4) illustrate similar histological features (to SCC) of invasive poorly differentiated aggressive cancers with typical features of dysplastic epithelial cells, epidermal keratinocyte atypia, epidermal hyperkeratotic nodules and membrane rafts invading the dermis (FIGS. 6A-F).

The expression of Flightless I was next examined in normal skin (n=4), the skin of melanoma (n=4), SCC (n=10), EB-SCC (n=4) and BCC (n=4) patients, and in SCC induced wild-type and Flightless I oberexpressing mice (n=12) using immunohistochemistry. In addition, Flightless I protein levels were quantified in the serum of SCC (n=3), BCC (n=3), melanoma (n=1) patients and a Normal Human Serum (NHS) control. Skin and serum samples were obtained from the RMIT University Tissue Bank containing samples collected from patients, male and female, of all ages. All patients signed the consent form agreeing to donate samples for research purposes and no ethics approval was sought as all tissue was received unidentified for educational and research purposes by the RMIT University. Classifications of melanoma, SCC or BCC were based on clinical presentations and histological presentations. Skin samples were formalin fixed and cut into 4 micron sections as described in Example 2. Skin tissue sections were then subjected to antigen retrieval and immunohistochemistry. This involved the use of a standard antigen retrieval procedure using the primary antibodies described in Example 1, and secondary antibodies as described below. Briefly, tissue sections were dewaxed by a series of xylene changes (30 min) and gradual ethanol washes (100% for 1 min, 70% for 1 min and 30% for 1 min), before being rinsed in 1× Phosphate Buffered Saline (PBS) and pre-treated with 250 ml Target Retrieval Solution (TRS) solution (2.8 g Citric Acid, 3.76 g Glycine, 0.372 g EDTA, pH 5.9 in 1 L 1×PBS). The sections were then microwaved for 2 min on "high" after which a "ballast" pot of water was added to help absorb some heat and pre-treatment continued for 2×5 min with regular "airing" to let the steam out and ensure that the temperature reached 94° C. but not 100° C. Sections were then cooled to 50° C. on ice before they were washed in fresh 1×PBS, and then enzyme digestested with 0.0625 g of Trypsin (Sigma-Aldrich, Sydney, Australia) dissolved in 1×PBS and pre-warmed to 37° C. Following the 3 min enzyme digestion at 37° C., sections were washed in 1×PBS and then incubated for 30 min in NHS blocking solution (3% NHS in 1×PBS). Slides were then washed in 1×PBS for 2 min and then incubated in primary antibody in a humid airtight box overnight at 4° C. Sections were then washed 3×2 min in 1×PBS and then incubated in Alexa Flour fluorescent species specific secondary antibody for 1 hr in a dark humid box. The secondary antibody used was Alexa Flour 488 anti-rabbit (A11008) obtained from Invitrogen. Slides were then washed 3×2 min in 1×PBS to remove any non-specific binding and mounted in a Dako Fluorescent Mounting Medium (DAKO Corporation, Botany, Australia). Slides were stored in the dark at −20° C. Integrated fluorescence intensity was determined using the AnalySIS software package (Soft-Imaging System GmbH, Munster, Germany). Negative controls were included to demonstrate antibody staining specificity. Control samples enderwent the same staining procedure outlined above, except omitting the primary or secondary antibody. All control sections had negligible immunofluorescence.

Figure 8:
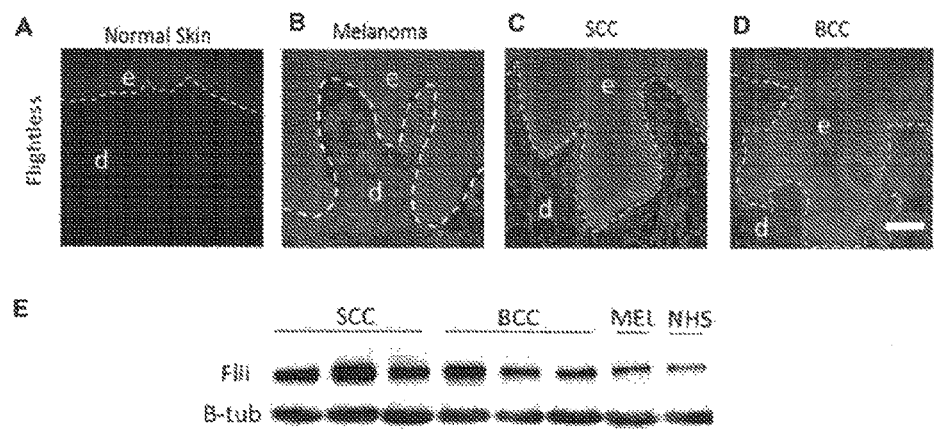
FIG. 8—representative images of the expression characteristics of Flightless I protein in normal healthy skin (panel A), and the skin of melanoma (panel B), SCC (panel C) and BCC (panel D) patients. e=epidermis, d=dermis, dotted line=basement membrane. Magnification ×20. Scale bar=100 µm. Panel E—Flightless I expression in the serum of SCC, BCC and melanoma (MEL) patients, and in a Normal Human Serum (NHS) control as determined by Western Blotting. β-tubulin (β-tub)=loading control.
Figure 9:
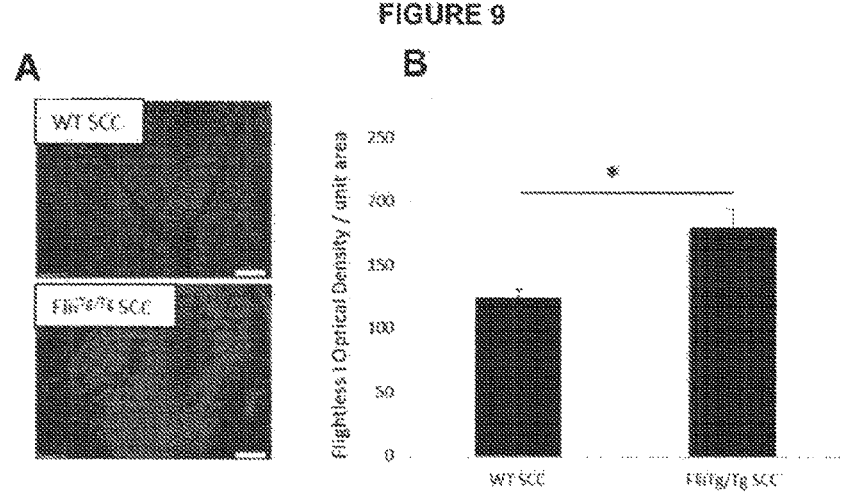
FIG. 9—representative images (A) and graphical analysis (B) of Flightless I expression in SCC tumours induced in wild-type (WT SCC) and Flightless I overexpressing mice (Flii$^{Tg/Tg}$ SCC). n=12. Magnification=×20. Scale bar=100 µm. Figure is representative of two independent experiments.
Figure 10:
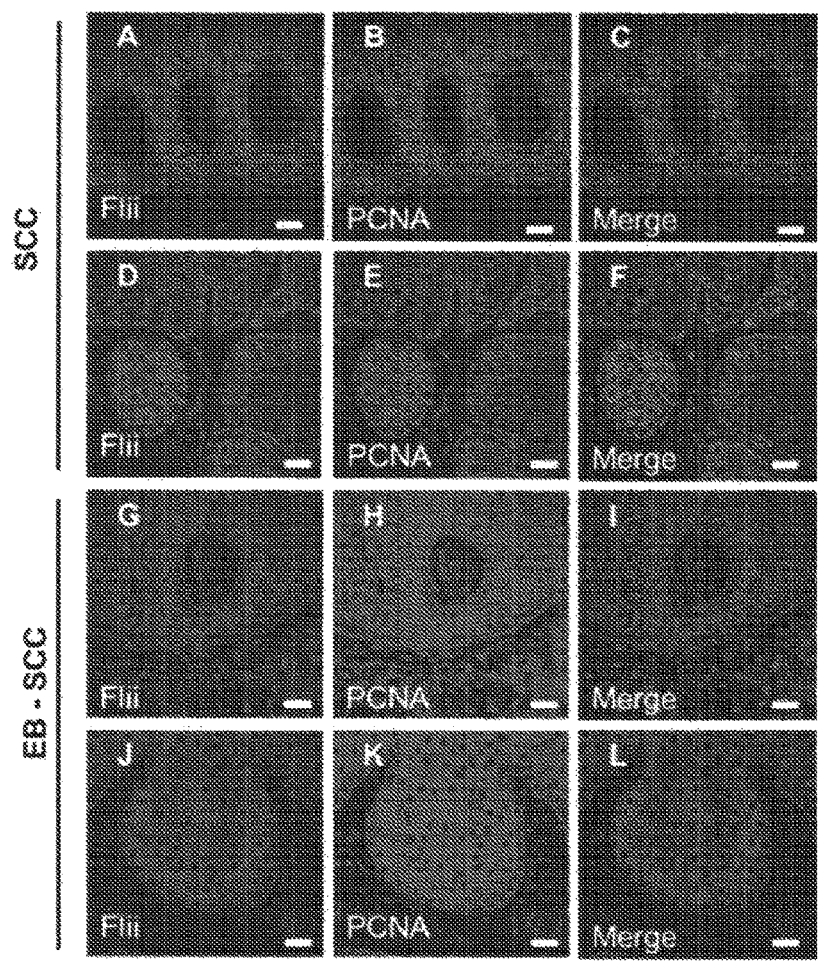
FIG. 10—images of the localisation of Flightless I protein in SCC lesions of otherwise healthy patients (panels A and D), and SCC lesions from Epidemal Bullosa patients (EB-SCC—panels G and J). Panels B and E show the localisation of the PCNA protein (a marker of proliferating cells) in SCC lesions of otherwise healthy patients, and panels H and K show the localisation of PCNA in SCC lesions from Epidemal Bullosa patients (EB-SCC). Panels C, F, I and L show the merged images of panels A/B, D/E, G/H, and J/K, respectively.

Results showed significantly increased expression of Flightless I in both human SCC and EB-SCC lesions compared to normal healthy skin with specific staining in dysplastic hyperproliferative epithelial cells, epidermal hyperkeratotic nodules and in dermal cells of tumour stroma (FIGS. 7A-H). Furthermore, Flightless I expression is increased in both the epidermis and dermis in response to tumour development and is specifically high in invading epithelial tumour cells of melanoma, SCC and BCC patients (FIGS. 8A-D). Finally, tumour sections of Flightless I overexpressing mice have significantly higher Flightless I levels in vivo (FIGS. 9A and B). These results indicate that Flightless I levels are increased in cancer development independent of EB. Furthermore, these results indicate that the increased incidence of SCC development observed in Flightless I overexpressing mice may be attributed to the increased levels of Flightless I in these mice.

Flightless I protein expression was also examined in the serum of SCC (n=3), BCC (n=3) and melanoma (n=1) patients and a Normal Human Serum (NHS) control as determined by Western Blotting. The procedure used was as described in Example 1 and results of two idependent experiments are shown in FIG. 8E. While Flightless I is expressed in NHS, its level of expression is higher in the serum of melanoma patients and significantly higher in the serum of BCC and SCC patients. Collectively, the data from these experiments suggest a role for Flightless I in different cutaneous tumour pathologies.

Tissue sections were also examined by immunohistochemistry for the presence of the PCNA protein, a marker of proliferating cells. Antigen retrieval and immunohistochemistry was performed as described above using a PCNA anti-mouse primary antibody (sc-56) obtained from Santa Cruz, and the Alexa Flour 594 anti-mouse secondary antibody. Flightless I was found to collocalize with PCNA in both SCC (n=10) and EB-SCC (n=4) suggesting a role for Flightless I in promoting proliferation of cancer cells (FIGS. 10A-L) and a role in cutaneous cancer pathology. Accordingly, Flightless I may affect epithelial cancer development, growth and metastasis either through a direct effect on cancer cells or through its effects on surrounding tumour stroma.

EXAMPLE 4

Flightless I Expression in SCC Cell Lines and RDEB-SCC Keratinocytes

Flightless I expression in SCC cell lines and RDEB-SCC keratinocytes was determined using Western analysis and immunohistochemistry, as described in detail above. SCC cell lines (SCC-IC1, SCC-IC2 and MET-1) were cultured as described above in Example 1, while human RDEB-SCC keratinocytes (CC, SBK and GP) were first lysed in 1× Triton-lysis buffer (20 mM Tris pH 7.4, 137 mM NaCl, 2 mM EDTA pH 7.4, 1% Triton X-100 and 10% glycerol) containing a protease-inhibitor cocktail (Roche, UK) and 10 mM EDTA prior to Western blotting. The expression of FLAP-1, a protein which binds to Flightless I, was also determined in the SCC cell lines SCC-IC1 and MET-1. The primary antibody used in this experiment was anti-FLAP-1 rabbit polyclonal antibody (ARP59016_P050) purchased from Aviva Systems Biology, and the secondary antibody was polyclonal goat anti-rabbit IgG-HRP (PO488) purchased from Dako An agilent Technologies Company.

The effect of Flightless I and FLAP-1 expression in response to decreasing Collagen VII (ColVII) levels in the SCC cell lines SCC-IC1 and MET-1 was also determined. Collagen VII is the main constituent of anchoring fibrils holding the skin layers together. Patients suffering from EB have mutations in the ColVII gene resulting in decreased or absent expression of ColVII, subsequent impaired anchoring fibrils and fragile skin. This results in spontaneous wide spread blistering that often leads to development of aggressive SCC. Therefore, this experiment examined the effect of Flightless I and FLAP-1 on SCC cells that have decreased ColVII levels which would mimic the features seen in EB patients. To effect ColVII knock-down, the SCC-IC1 and MET-1 cell lines were transfected with a SMARTpool of four synthetic siRNAs (Dharmacon, UK), targeting ColVII (#M-011017-00). Transfection was performed according to the manufacturer's protocol and optimized for a six-well plate. Briefly, cells were plated at 50% confluency and subjected to transfection the following day using 4 µg of DharmaFECT1 (Dharmacon, UK) transfection reagent and 12.5 nM final concentration of each siRNA. Transfection media were replaced with complete DMEM:Ham's F12 media after 16 hours. Flightless I or FLAP-1 protein expression was analyzed by Western Blotting on cell extracts, as described above. Cells incubated with the transfection reagent only (Mock) as well as cells transfected with a pool of non-targeting siRNAs (siCONTROL Non-Targeting siRNA Pool) were used as negative controls. β-tubulin or GAPDH were used as loading controls.

Figure 11:
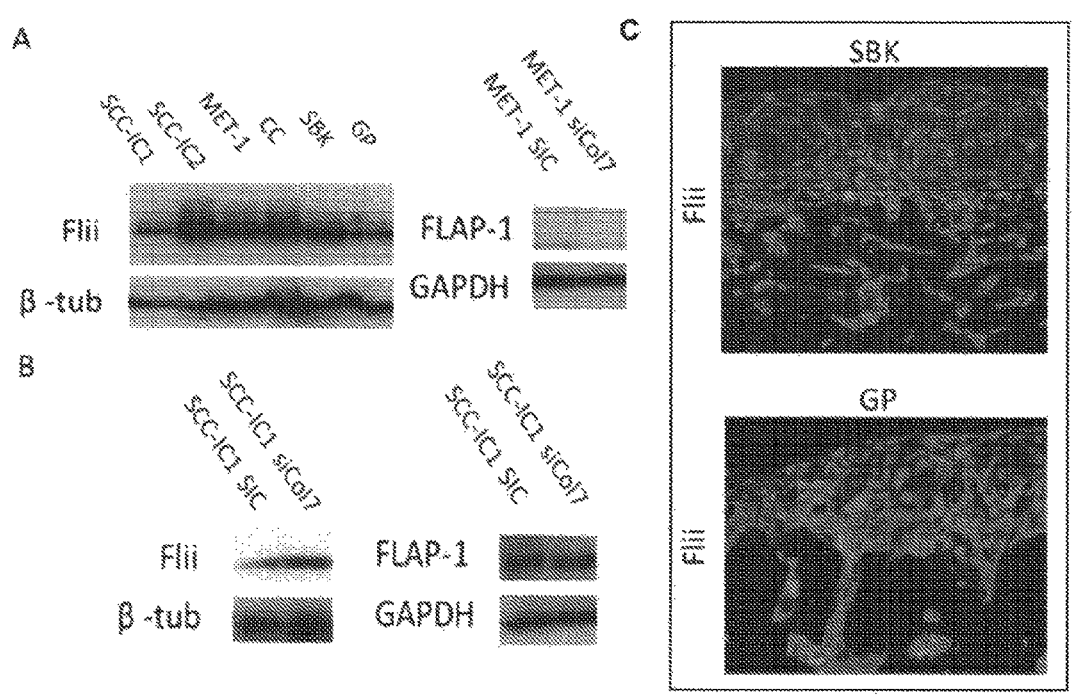
FIG. 11—results of expression analysis of Flightless I protein (Flii) and the Flightless I binding protein (FLAP-1). A: expression of Flii and FLAP-1 in different SCC (SCC-IC1, SCC-IC2, and MET-1) and EB-SCC (CC, SBK, and GP) cell lines. B: expression of Flii and FLAP-1 in the SCC-IC1 cell line in the absence (SCC-IC1 SIC) and presence (SCC-IC1 siCol7) of an siRNA to Col7. C: localisation of expression of Flightless I (Flii) protein in EB-SCC keratinocytes (SBK and GP) in a 3 dimensional organotypical model of EB-SCC.

The results of these experiments are shown in FIG. 11. Flightless I, but not its binding protein FLAP-1, was expressed in the SCC cell lines and human RDEB-SCC keratinocytes which have different expression levels of ColVII (n=3) (FIG. 11A). In addition, reduction of ColVII significantly increases the expression of Flightless I, but not FLAP-1, in SCC cell lines (FIG. 11B), and Flightless I is specifically expressed by invading human RDEB-SCC keratinocytes (SBK and GP) in a 3D organotypic model of RDEB-SCC (FIG. 11C). This suggests a role for Flightless I in development of SCC in EB patients. These findings also suggest that modulation of Flightless I levels in skin of EB patients may be beneficial in decreasing the onset of SCC lesions or decreasing the growth and metastasis of SCC tumours. This is of vital importance as two thirds of RDEB patients die from aggressive metastatic SCC.

EXAMPLE 5

Decreasing the Level of Flightless I in Epidermal Models of SCC and EB-SCC

A three dimensional organotypic model of EB-SCC was used to determine the effect that decreasing Flightless I expression had on the invasion properties of SCC tumour cells. Briefly, organotypic cultures on collagen:matrigel gels were performed as previously described (Martins et al., 2009, J. Cell Sci., 122: 1788-1799). Collagen:matrigel gels were prepared by mixing 3.5 volumes of type I collagen (First Link, UK), 3.5 volumes of Matrigel (BD Biosciences, UK), 1 volume of 10×DMEM, 1 volume of FCS and 1 volume of DMEM with 10% FCS/HFF (resuspended at a density of $5 \times 10^6$/ml). One ml of the gel mixture was placed into each well of a 24-well plate and allowed to polymerize at 37° C. for 1 hour. After polymerization, 1 ml of DMEM was added per well and gels were incubated for 18 hours to equilibrate. SBK, GP, MET-1 and/or CC cells were seeded into a plastic ring placed on the top of the gel at a density of $5 \times 10^5$ per gel. Cells were seeded in media containing rFLAP-1 (100 ng/ml), a Flightless I neutralising antibody (FnAB—100 µg/ml), a dose matched IgG control antibody, or a PBS control. The rFLAP-1 protein was purchased from Abnova Technologies (LRRFIP1 (657-784) Protein—H00009208-Q01). The Flightless I neutralising antibody was made in-house and was an affinity-purified mouse monoclonal anti-Flightless (FnAb) $IgG_1$ antibody raised against a Leucine-Rich Repeat (LRR) domain of the Flightless I protein. After 24 hours, the rings were removed and gels were raised to the air-liquid interface on stainless steel grids. Media, containing rFLAP-1, FnAb, IgG control or PBS control, was changed every second day and gels were harvested at day 10, fixed in 4% paraformaldehyde (PFA) and embedded in paraffin. Paraffin sections of invading SCC cells (SBK and GP—for Example 4) were stained for Flightless I expression using the immunohistochemistry protocol described above. Paraffin sections of invading sporadic SCC cells (MET-1) and EB-SCC cells (CC) treated with rFLAP-1, FnAB, IgG control or PBS control were either stained for Haematoxylin and Eosin with depth of invasion measured using AnalySIS software package (Soft-Imaging System GmbH, Munster, Germany), or were used for Flightless and TGF-β1 expression (Example 6) and co-localization analysis as detailed above.

Figure 12:
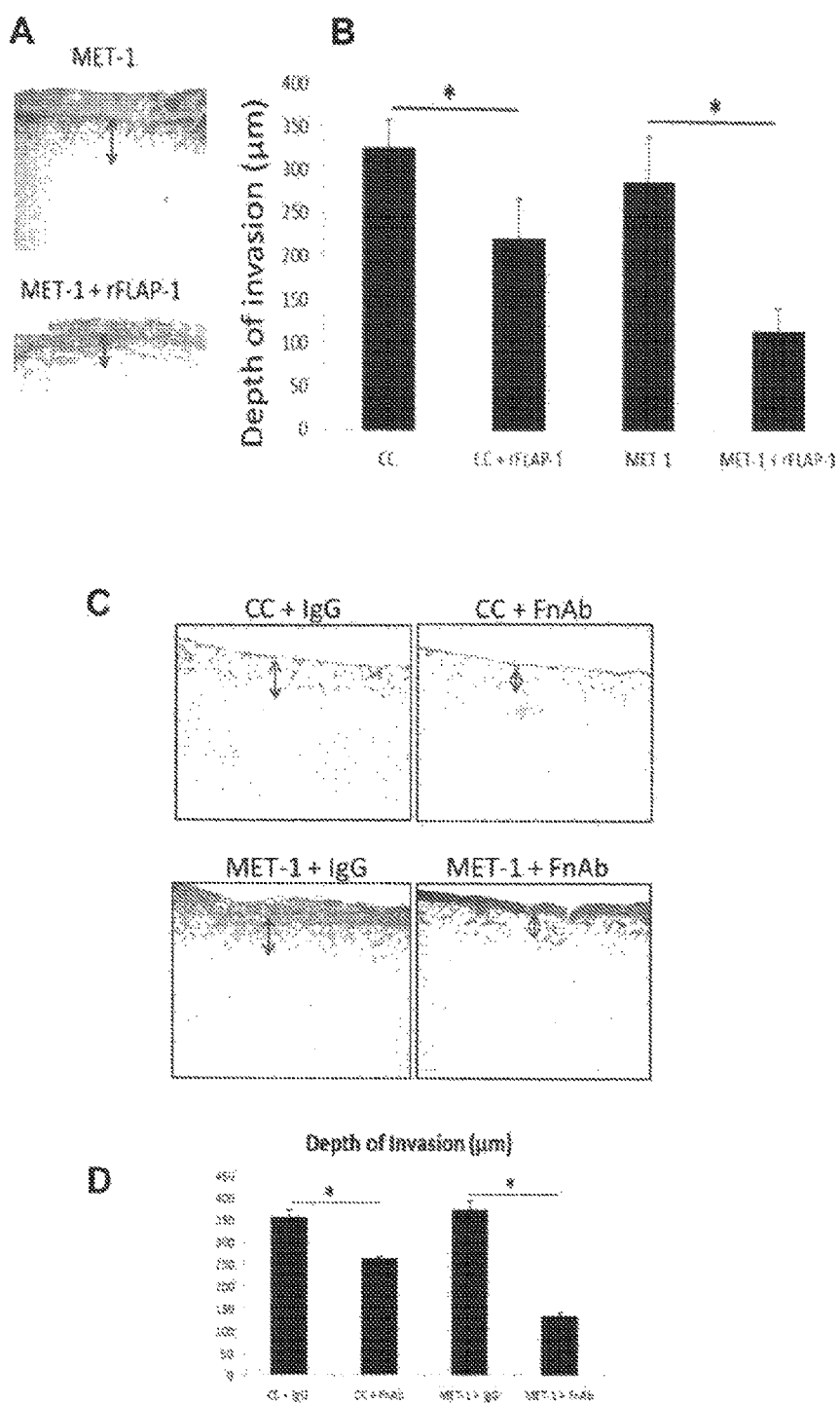
FIG. 12—results of the presence of Flightless I inhibitors (FLAP-1 and FnAb) on Flightless I protein expression in sporadic SCC (MET-1) and EB-SCC (CC) cell lines. A: histological representation of tumour invasion in the absence (MET-1) and presence (MET-1+rFLAP-1) of FLAP-1; B: a graph showing the depth of tumour invasion in the absence (CC and MET-1) and presence (CC+rFLAP-1 and MET-1+rFLAP-1) of FLAP-1; C: histological representation of tumour invasion in the absence (CC+IgG and MET-1+IgG) and presence (CC+FnAb and MET-1+FnAb) of a neutralising antibody to Flightless I (FnAb); D: a graph showing the depth of tumour invasion in the absence (CC+IgG and MET-1+IgG) and presence (CC+FnAb and MET-1+FnAb) of a neutralising antibody to Flightless I (FnAb).

As shown in FIG. 12A, sporadic SCC (MET-1) and RDEB-SCC (CC) cell invasion properties, in response to decreasing Flightless I levels by means of rFLAP-1, were significantly reduced by 60% and 30% respectively. Furthermore, decreasing Flightless I levels using a Flightless neutralising antibody (FnAb) also significantly reduced the depth of SCC cell invasion of human EB-SCC (26% reduction) or sporadic SCC (64% reduction) keratinocytes (FIG. 12C). These results suggested that Flightless I is a novel target for SCC therapy development and that by reducing Flightless I a decrease in tumour invasion and metastasis may be achieved.

EXAMPLE 6

Effect of Flightless I on TGF-β Signalling

Figure 13:
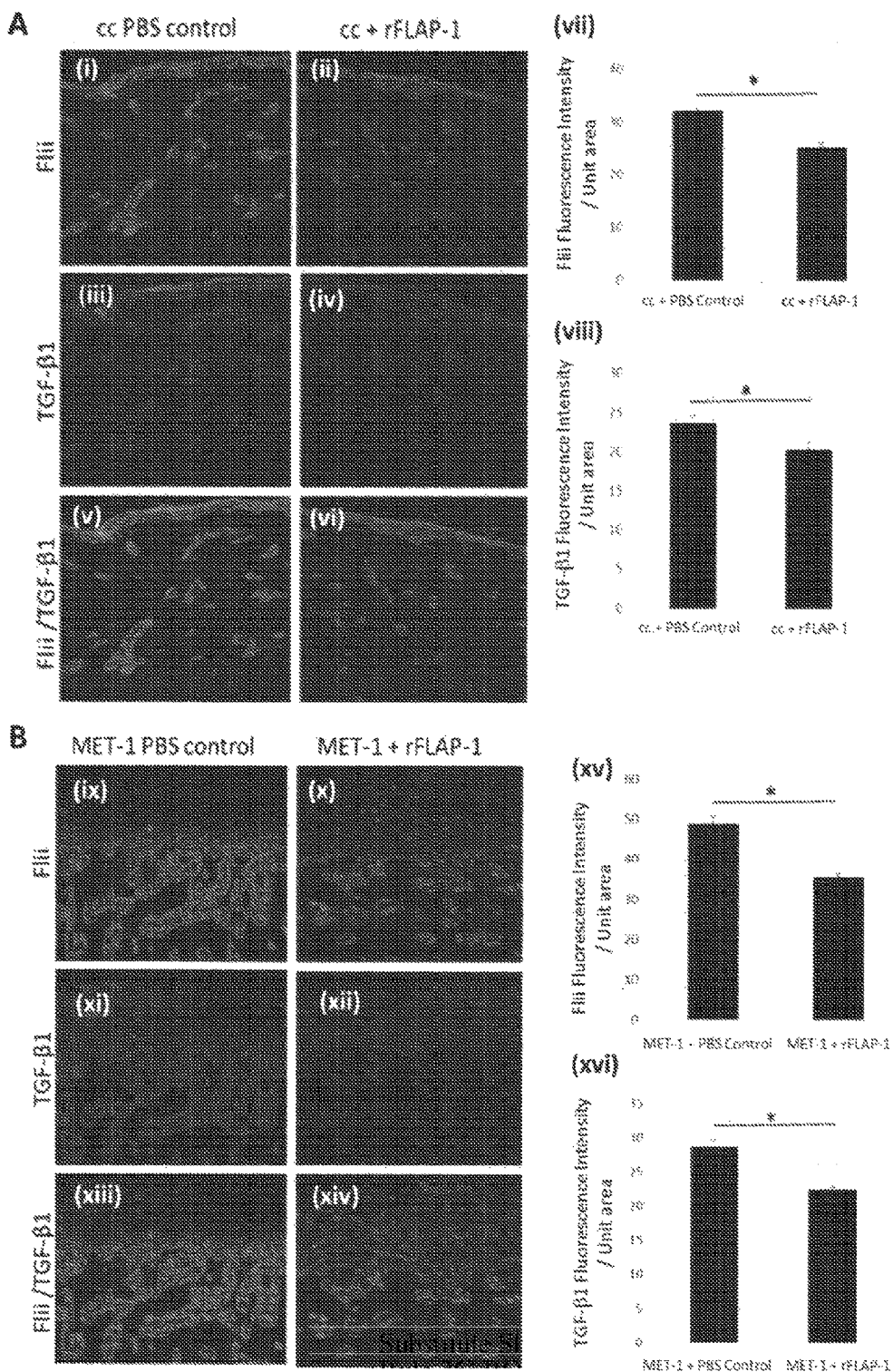
FIG. 13—results of decreasing Flightless I (Flii) expression/activity by FLAP-1 on TGF-β signalling in SCC (CC) and EB-SCC (MET-1) cells. A: histological representation of the results for CC cells in the absence (cc PBS control) and presence (cc+rFLAP-1) of FLAP-1 (left panels). A graphical representation of the results is shown on the right of the panels; B: histological representation of the results for MET-1 cells in the absence (MET-1 PBS control) and presence (MET-1+rFLAP-1) of FLAP-1 (left panels). A graphical representation of the results is shown on the right of the panels.

One possible mechanism behind the effect of Flightless I on SCC cell invasion and tumour growth is the effect of Flightless I on the TGF-β signalling pathway. TGF-β signalling is instrumental in cancer invasion and metastasis and contributes to the development of SCC in patients with EB (Ng Y Z et al., 2012, *Cancer Res.,* 72: 3522-3534). Immunohistochemistry was used according to the methods described above in Example 5 to investigate the effect that decreasing the expression of Flightless I (by rFLAP-1) had on TGF-β1 expression in 3D organotypic SCC (CC) or RDEB-SCC (MET-1) gels treated with rFLAP-1 or PBS control. Results showed that using the rFLAP-1 treatment, Flightless I expression can be decreased which subsequently reduces TGF-β signalling (FIG. 13A and FIG. 13B). Invading hyperproliferative cancerous cells have a specifically high Flightless I expression. Taken together these results suggest that modulating Flightless I expression may be beneficial in reducing development, growth and invasion of SCC mediated through TGF-6 signalling in both SCC and EB-SCC pathology.

EXAMPLE 7

Decreasing the Level of Flightless I in Primary Cutaneous SCC of Wild-Type and Transgenic Mice Primary cutaneous SCC was induced in twenty four age and sex matched wild-type Balb/c mice, 4-6 weeks old, with body weights of about 18 grams, by a single intradermal injection of 3-Methylcholanthrene (100 μl corn oil containing 500 μg of MCA) administered to a designated site on the back of each mouse. Mice start developing inflammatory lesions following MCA injection which then progress to ulcerated lesions around week 7 of the trial and necrotic ulcerated nodular SCC by 9 weeks post-SCC induction. Flightless I (Flii) expression/activity was reduced by administrating 100 μl of an in-house produced neutralising antibody to Flightless I (FnAb) (50 μg/ml) or IgG dose matched control antibodies every two weeks including week 0, 2, 4, 6 and 8 using four intradermal injections (25 μl) around the initial MCA injection site or tumour base at later time-points (n=12/treatment). Mice were euthanized at week 10 of the experiment by which time necrotic ulcerated nodular SCC was well developed and samples of non-lesional and lesional tumour skin were collected and either fixed in 10% formalin and processed for histology and immunofluorescence or microdissected and fast frozen for mRNA and protein extraction as previously described. SCC development was analysed macroscopically using electronic callipers in-vivo and ex-vivo following established protocols including microscopic analysis of length of tumour epithelium, cross sectional tumour width and tumour volume.

Figure 14:
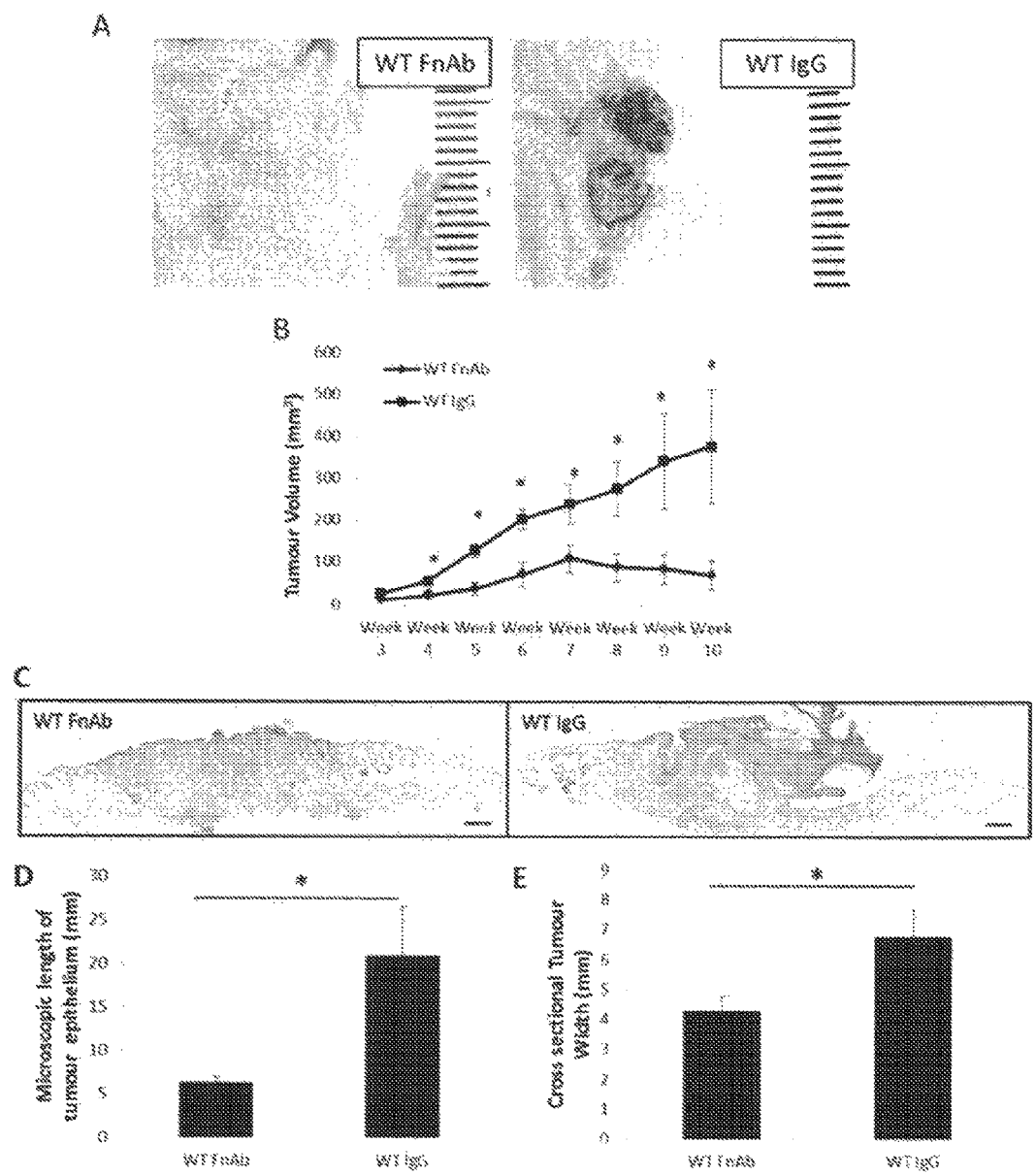
FIG. 14—results of decreasing Flightless I (Flii) expression/activity in wild-type mice using a neutralising antibody to Flii (FnAb) on SCC growth and severity. A—representative macroscopic images of wild-type mice treated with FnAb or IgG antibodies at week ten of the experiment. B—macroscopic assessment of tumour volume showing decreased tumour growth in FnAb treated mice with significantly decreased tumour volume from week 4 of the experiment. C—representative images of haematoxylin and eosin stained sections of wild-type mice treated with FnAb or IgG antibodies at week ten of the experiment. Microscopic analysis of tumour length (D) and width (E) showing decreased SCC tumour growth and severity in FnAb treated mice with IgG control antibody. n=12/treatment.

The results of these experiments are collectively represented in FIG. 14. As shown in FIG. 14A, the growth of SCC tumours in-vivo was visually reduced by the FnAb when compared to control IgG antibodies. These results demonstrate an effective approach to modulating SCC tumour growth in-vivo using FnAb. Mice treated with FnAb had a significantly decreased tumour volume from week 4 of the experiment (FIG. 14B). Representative images of haematoxylin and eosin stained sections of wild-type mice treated with FnAb or IgG antibodies at week ten of the experiment are shown in FIG. 14C. Microscopic analysis of tumour length (FIG. 14D) and width (FIG. 14E) showed decreased SCC tumour growth and severity in FnAb treated mice compared with the IgG control antibody.

Figure 15:
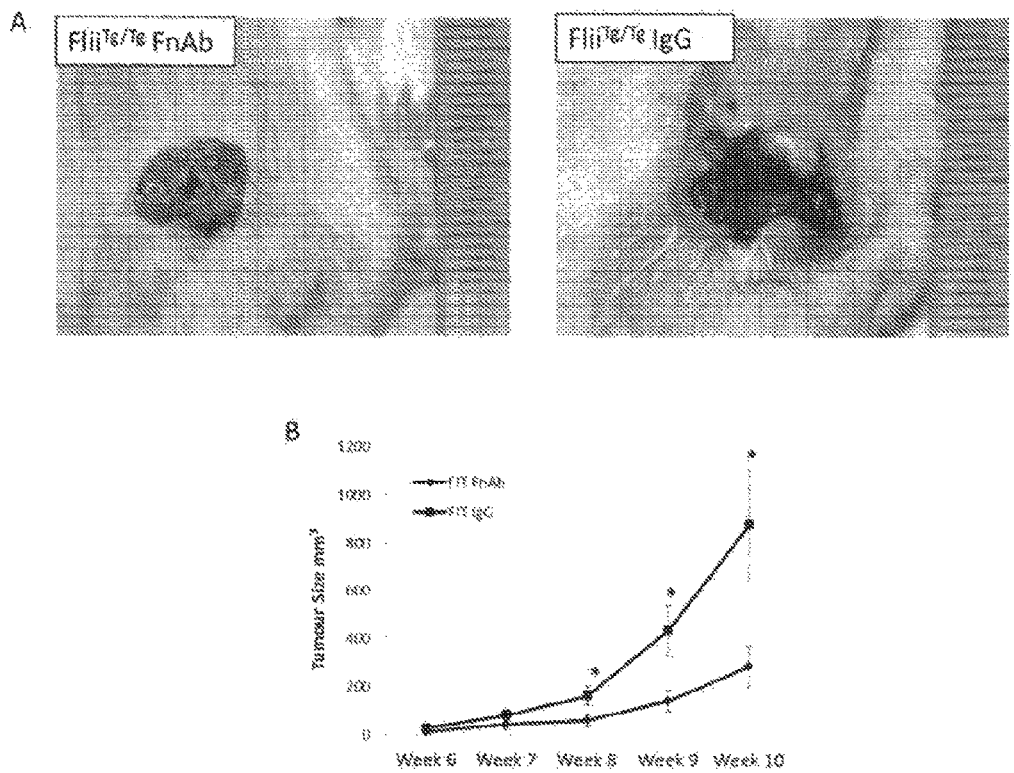
FIG. 15—representative images (A) of Flightless I overexpressing mice (Flii$^{TG/Tg}$) pre-treated with an antibody to Flightless I (FnAb) or IgG and MCA induced for SCC development over a 10 week period. B—a graph showing that Flighltess I overexpressing mice treated with FnAb demonstrated significantly reduced macroscopic tumour volume from week 8 of the experiment. n=12.

The same experiment was conducted on Flightless I overexpressing mice ($Flii^{Tg/Tg}$) induced for SCC. This is because patients with epidermolysis bullosa, who have a high predisposition to the development of SCC, also have higher expression of Flightless I in blistered skin. As shown in FIG. 15, pre-treatment of Flightless I overexpressing mice with an antibody to Flightless I significantly reduced SCC tumour growth and severity in vivo.

These studies provide evidence that reducing Flightless I levels in vivo, for example using a neutralising antibody to Flightless I (FnAb), can significantly reduce the growth and severity of primary cutaneous SCC. Furthermore, inhibitors of Flightless I can also be used as a preventative treatment for SCC cancer development in individuals who are at high risk of developing SCC.

EXAMPLE 8

Effect of Flightless I Expression on Other Cancer Types

To examine the effects of Flightless I expression on other cancer types, primary and metastatic tumour development was examined in transgenic Flightless mice. CT26 mouse colon cancer cells were used to induce primary and metastatic tumors in $Flii^{+/-}$ (mice underexpressing Flightless I), WT and $Flii^{Tg/-}$ (mice overexpressing Flightless I) female mice aged six-eight weeks. To induce primary tumours, cells were injected into the dermis of the flank, specifically $5\times10^5$ cells in an injection volume of 100 μl was used. Primary tumours were measured using electronic callipers daily after injection. Primary tumours were then weighed and fixed for histology at sacrifice of the animals which was 19 days post-injection. For the metastatic model, $3\times10^5$ CT26 cells were injected into the tail vein of the mouse and the lungs were removed at sacrifice (day 14). At this time visible macroscopic metastases werecounted (on the surface of the lung) and lungs were weighed and fixed for histology, as described above. Macroscopic primary tumour size and metastatic tumour numbers were analysed. Both primary and metastatic tumour samples were analysed for expression of α-SMA indicative of cancer associated fibroblasts surrounding the tumour stoma, using immunohistochemistry as detailed above. Primary lung fibroblasts collected from $Flii^{+/-}$ and $Flii^{Tg/-}$ mice were also analysed for expression of α-SMA using flow cytometry to investigate the effect of Flightless I expression on α-SMA expression in fibroblasts.

Figure 16:
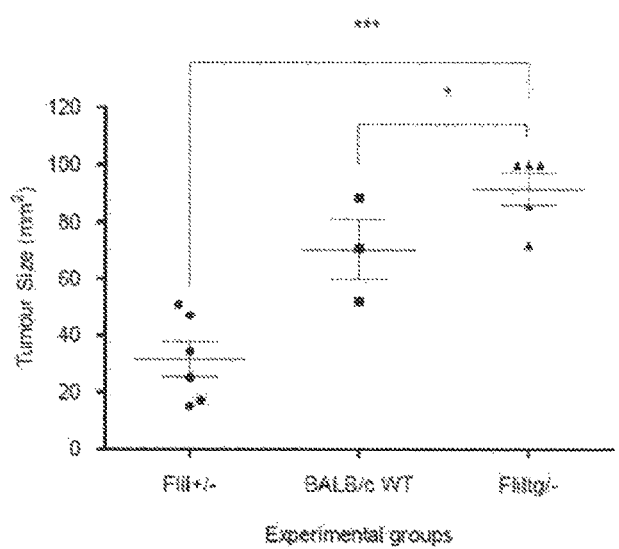
FIG. 16—graph showing the effect of Flightless I expression in other cancer types. Mice were injected with colon cancer cells and the growth of primary tumour development was analysed. Fliitg/–: mice overexpressing Flightless I; BALB/c WT: wildtype mice; and Flil+/–: mice with reduced Flightless I expression.
Figure 17:
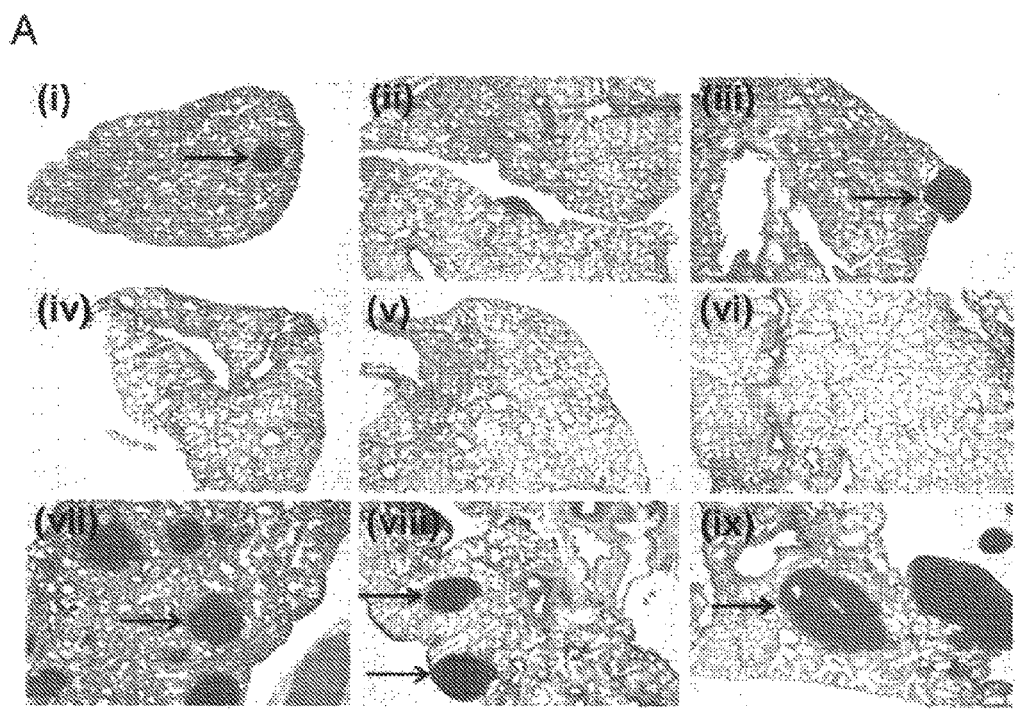
FIG. 17—analysis of the development of metastatic nodules in lung tissue of the mice of FIG. 12 which were injected with colon cancer cells. A: histological representations of the results. Top panels: wildtype mice; middle panels: Flil+/– mice; bottom panels: Fliltg/– mice. B: graphical representation of the number of tumour nodules in lung tissue from each of three mice groups. Metstatic nodules are represented by arrows.
Figure 17:
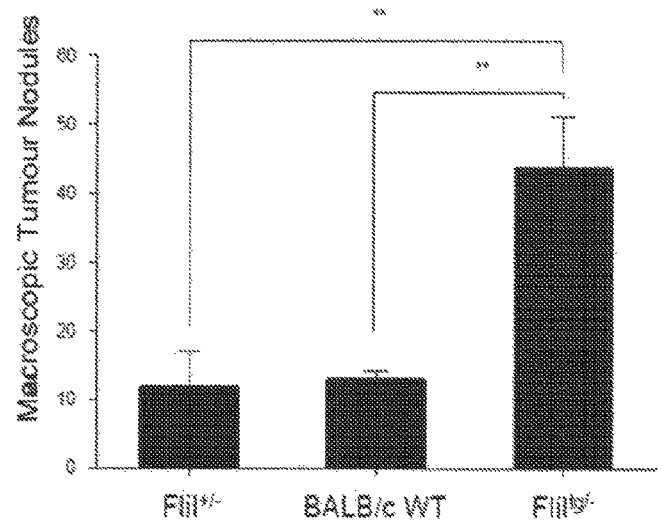

Results of these experiments are shown in FIGS. 16 to 19. Mice with reduced Flightless I expression (Flii$^{+/-}$) showed significantly smaller primary tumours than either control (WT) or Flightless I (FliI$^{Tg/-}$) over-expressing mice (p<0.001, n=10)(FIG. 16). Furthermore, mice overexpressing Flightless I showed a significantly greater spread of tumours to metastatic nodules in the lung (p<0.001, n=10) (FIG. 17A). Conversely, mice with reduced Flii expression (FliI$^{+/-}$ mice) grew smaller tumours (FIG. 17B) and showed fewer metastatic nodules in the lung (FIG. 17A). Control mice of the same genetic background (BALBc) expressing normal levels of Flii (WT), showed a phenotype that was intermediate between the other two mice strains.

Figure 18:
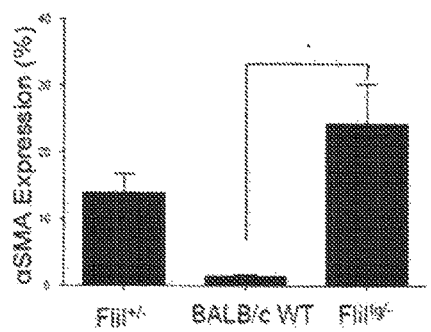
FIG. 18—graphs summarising analysis of the expression of α-SMA in Flightless I overexpressing mice (Fliltg/–), wildtype mice (BALB/c WT) and mice with reduced Flightless I expression (Flil+/–) in primary (A) and metastatic (B) tumours. (n=10).
Figure 18:
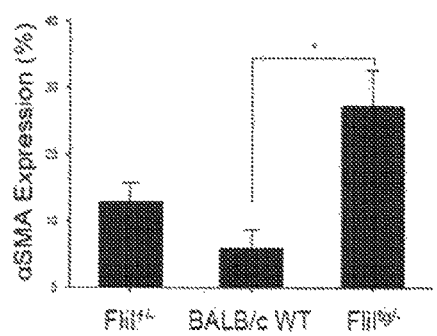
Figure 19:
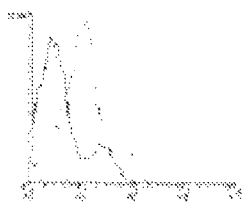
FIG. 19—graphs summarising analysis of the expression of α-SMA in unstimulated primary lung fibroblasts from Flightless I overexpressing mice (Fliltg/–) (panel B) compared to lung fibroblasts from Flightless I heterozygous mice (Flil+/–) (panel A), and a side-by-side comparison of the same (panel C). (n=10).
Figure 19:
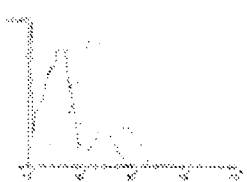
Figure 19:
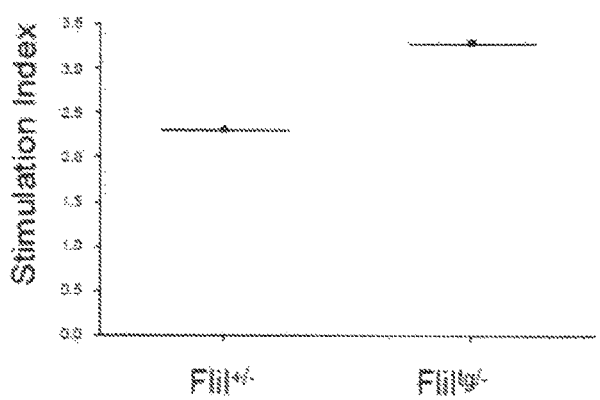

Myofibroblasts (α-SMA positive cells) in a tumour environment are referred to as cancer associated fibroblasts (CAFs) and compose up to 70-90% of the tumour mass in some cancers (Desmouliere A et al., 2004, *Int. J. Dev. Biol.*, 48: 509-517). Both primary and metastatic tumours in Flightless I overexpressing mice had a significantly higher expression of α-SMA compared to WT controls (FIG. 18). Higher expression of α-SMA promotes higher activation of CAFs which through altered secretion of growth factors and cytokines promote tumour proliferation and metastasis (Basset P et al., 1990, *Nature* 348: 699-704). In addition, α-SMA expression was higher in unstimulated primary lung fibroblasts extracted from Flightless I overexpressing mice suggesting a more differentiated cell phenotype that could promote more tumour stroma (FIG. 19). Taken together the increased expression of α-SMA observed in Flightless I overexpressing mice could be one potential mechanism behind increased activation of CAF's and may explain increased primary cancer growth as well as metastasis to the lung.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

The invention claimed is:

1. A method of treating skin cancer in a subject, inhibiting the growth of a cancerous skin cell in a subject, inhibiting growth of a skin cancer in a subject, or inhibiting invasion and metastasis of a skin cancer in a subject, the method including the step of administering to the subject an effective amount of an active agent that decreases the expression and/or activity of Flightless I in the subject, wherein the active agent is a neutralizing antibody to Flightless I or an antigen binding part of a neutralizing antibody to Flightless I.

2. The method of claim 1, wherein the skin cancer or cancerous skin cell is a squamous cell carcinoma or a cancerous squamous cell.

* * * * *

SEQUENCE LISTING

<160> NUMBER OF SEQ ID NOS: 16

<210> SEQ ID NO 1
<211> LENGTH: 4387
<212> TYPE: DNA
<213> ORGANISM: Homo sapiens

<400> SEQUENCE: 1

```
aactccagca caggggggc ccgcactcct tggtgcctcc gcagtcttcg aacagacggg      60
gaaactgagg ccctaagagg cctaaagcct acacttcccc gcggaatgcg gcgggcgcgg     120
gcgggttaaa ggggcggggc cggcgctggc ccagcccgcg gctccccca gcgccctcgc     180 cccggcgctc cctagcccgg cgcggcccgg cagcgagagc ggcgccatgg aggccaccgg     240
ggtgctgccg ttcgtgcgtg gcgtggacct cagcggcaac gacttcaagg gcggctactt     300
ccctgagaat gtcaaggcca tgaccagcct gcggtggctg aagctgaacc gcactggcct     360
ctgctacctg cccgaggagc tggccgcct gcagaagctg aacacttgt ctgtgagcca     420 caacaacctg accacgcttc atggggagct gtccagcctg ccatcgctgc gcgccatcgt     480
ggcccgagcc aacagtctga agaattccgg agtcccgat gacatcttca agctagatga     540
tctctcagtc ctggacttga gccacaacca gctgacagag tgcccgcggg agctggagaa     600
cgccaagaac atgctggtgc tgaacctcag ccacaacagc atcgacacca tccccaacca     660
gctcttcatc aacctcactg acctactata cctggacctc agcgagaacc gcctggagag     720 cctgccccg cagatgcgcc gcctggtgca cctgcagacg ctcgtgctca atggaaaccc     780
cctgctgcat gcacagctcc ggcagctccc agcgatgacg gccctgcaga ccctgcacct     840
gcggagcacc cagcgcaccc agagcaacct gcccaccagc ctggagggtc tgagcaacct     900
cgcagacgtg gatctgtcct gcaatgacct gacacgggtg cccgagtgtc tgtacaccct     960
ccccagcctg cgccgcctca acctcagcag caaccagatc acggagctgt ccctgtgcat    1020
agaccagtgg gtgcacgtgg aaactctgaa cctgtcccga aatcagctca cctcactgcc    1080
ctcagccatt tgcaagctga gcaagctgaa gaagctgtac ctgaattcca acaagctgga    1140
ctttgacggg ctgccctcag gcattggcaa gctcaccaac ctggaagagt tcatggctgc    1200
caacaacaac ctggagctgg tccctgaaag tctctgcagg tgcccaaagc tgaggaaact    1260
```

```
tgtcctgaac aagaaccacc tggtgaccct cccagaagcc atccatttcc tgacggagat    1320
cgaggtcctg gatgtgcggg agaaccccaa cctggtcatg ccgcccaagc ccgcagaccg    1380
tgccgctgag tggtacaaca tcgacttctc gctgcagaac cagctgcggc tagcgggtgc    1440
ctctcctgct accgtggctg cagctgcagc tgcaggagt gggcccaagg accctatggc     1500
tcgcaagatg cgactgcgga ggcgcaagga ttcagcccag gatgaccagg ccaagcaggt    1560
gctgaagggc atgtcagatg ttgcccagga gaagaacaaa aagcaggagg agagcgcaga    1620
tgcccgggcc cccagcggga aggtgcggcg ttgggaccag ggcctggaga gccccgcct    1680 tgactactcc gagttcttca cggaggacgt gggccagctg cccggactga ccatctggca    1740
gatagagaac ttcgtgcctg tgctggtgga ggaagccttc cacggcaagt tctacgaggc    1800
tgactgctac attgtgctca agacctttct ggatgacagc ggctccctca actgggagat    1860
ctactactgg attggcgggg aggccacact cgacaagaaa gcttgctctg ccatccacgc    1920
tgtcaacttg cgcaactacc tgggtgctga gtgccgcact gtccgggagg agatgggcga    1980
tgagagcgag gagttcctgc aggtgtttga caacgacatc tcctacattg agggtggaac    2040
agccagtggc ttctacactg tggaagacac acactatgtc accaggatgt atcgtgtgta    2100
tgggaaaaag aacatcaagt tggagcctgt gcccctcaag gggacctctc tggacccaag    2160
gtttgttttc ctgctggacc gagggctaga catctacgta tggcgggggg cccaggccac    2220
actgagcagc accaccaagg ccaggctctt tgcagagaaa attaacaaga atgagcggaa    2280
agggaaggct gagatcacac tgctggtgca gggccaggag ctcccagagt tctgggaggc    2340
actgggtggg gagccctctg agatcaagaa gcacgtgcct gaagacttct ggccgccgca    2400
gcccaagctg tacaaggtgg gcctgggctt gggctacctg gagctgccac agatcaacta    2460
caagctctcc gtggaacata gcagcgtcc caaggtggag ctgatgccaa gaatgcggct    2520
gctgcagagt ctgctggaca cgcgctgcgt gtacattctg gactgttggt ccgacgtgtt    2580
catctggctc ggccgcaagt ccccgcgcct ggtgcgcgct gccgccctca gctgggtca    2640 ggagctgtgc gggatgctgc accggccacg ccatgccacg gtcagccgca gcctcgaggg    2700
caccgaggcg caggtgttca aggccaagtt caagaattgg gacgatgtgt tgacggtgga    2760
ctacacacgc aatgcggagg ccgtgctgca gagcccgggt ctctccggga aggtgaaacg    2820
cgacgccgag aagaaagacc agatgaaggc tgacctcact gcgcttttcc tgccgcggca    2880
gccgcccatg tcgctggccg aggcggagca gctgatggag gagtggaacg aagacctaga    2940
cggcatggag ggtttcgtgc tggagggcaa gaagtttgcg cggctgccgg aagaggagtt    3000
tggccacttc tacacgcagg actgctacgt cttcctctgc aggtactggg tgcctgtgga    3060
gtacgaggag gaggaaaaga aggaagacaa ggaggagaag gccgagggca agaaggcga    3120 ggaagcaacc gctgaggcag aggagaagca gccagaggag gacttccagt gcatcgtgta    3180
cttctggcag ggccgtgaag cctccaatat gggctggctc accttcacct tcagcctgca    3240
aaagaagttc gagagcctct tccctgggaa gctggaggtg gtacgcatga cgcagcagca    3300
ggagaacccc aagttcctgt cccatttcaa gaggaagttc atcatccacc ggggcaagag    3360
gaaggcggtc cagggcgccc aacagcccag cctctaccag atccgcacca acggcagcgc    3420
cctctgcacc cggtgcatcc agatcaacac cgactccagc ctcctcaact ccgagttctg    3480
cttcatcctc aaggttccct ttgagagtga ggacaaccag ggcatcgtgt atgcctgggt    3540
gggccgggca tcagaccctg acgaagccaa gttggcagaa gacatcctga acaccatgtt    3600
```

```
tgacacctcc tacagcaagc aggttatcaa cgaaggtgag gagcctgaga acttcttctg    3660
ggtgggcatt gggcacagaa agccctatga tgacgatgcc gagtacatga aacacacacg    3720
tctcttccgg tgctccaacg agaagggcta ctttgcagtg actgagaaat gctccgactt    3780
ttgccaagat gacctggcag atgatggcat catgttgcta acaatggcc aagaggtcta     3840 catgtgggtg gggacccaga ctagccaggt ggagatcaag ctgagcctga aggcctgcca    3900
ggtatatatc cagcacatgc ggtccaagga acatgagcgg ccgcgccggc tgcgcctggt    3960
ccgcaagggc aatgagcagc acgcctttac ccgctgcttc cacgcctgga gcgccttctg    4020
caaggccctg gcctaagaca ggctggcaca gccccaggct tggtgaggaa gaggaagggg    4080
cctcatccac tgtctgctag caaagaatgt actcaggtga caccacctgc tccagccacg    4140
tccagtgcca cagtccccag tagcctcaag cagcaccaat ggggatgacc ctgacaggtg    4200
ccctcagggg tctgggaaat ccaactctct ccacagtgtg agtgcacgtg tgaagccccc    4260
tcactcttcc gctagggata aagcagatgt ggatgcccct taagagatat taaatgcttt    4320
tattttcaat attaaaaatc agtattttta atattaaaaa aaaaaaaaaa aaaaaaaaaa    4380
aaaaaaa                                                              4387

<210> SEQ ID NO 2
<211> LENGTH: 1269
<212> TYPE: PRT
<213> ORGANISM: Homo sapiens

<400> SEQUENCE: 2

Met Glu Ala Thr Gly Val Leu Pro Phe Val Arg Gly Val Asp Leu Ser
1               5                   10                  15

Gly Asn Asp Phe Lys Gly Gly Tyr Phe Pro Glu Asn Val Lys Ala Met
            20                  25                  30

Thr Ser Leu Arg Trp Leu Lys Leu Asn Arg Thr Gly Leu Cys Tyr Leu
        35                  40                  45

Pro Glu Glu Leu Ala Ala Leu Gln Lys Leu Glu His Leu Ser Val Ser
    50                  55                  60

His Asn Asn Leu Thr Thr Leu His Gly Glu Leu Ser Ser Leu Pro Ser
65                  70                  75                  80

Leu Arg Ala Ile Val Ala Arg Ala Asn Ser Leu Lys Asn Ser Gly Val
                85                  90                  95

Pro Asp Asp Ile Phe Lys Leu Asp Asp Leu Ser Val Leu Asp Leu Ser
            100                 105                 110

His Asn Gln Leu Thr Glu Cys Pro Arg Glu Leu Glu Asn Ala Lys Asn
        115                 120                 125

Met Leu Val Leu Asn Leu Ser His Asn Ser Ile Asp Thr Ile Pro Asn
    130                 135                 140

Gln Leu Phe Ile Asn Leu Thr Asp Leu Leu Tyr Leu Asp Leu Ser Glu
145                 150                 155                 160

Asn Arg Leu Glu Ser Leu Pro Pro Gln Met Arg Arg Leu Val His Leu
                165                 170                 175

Gln Thr Leu Val Leu Asn Gly Asn Pro Leu Leu His Ala Gln Leu Arg
            180                 185                 190

Gln Leu Pro Ala Met Thr Ala Leu Gln Thr Leu His Leu Arg Ser Thr
        195                 200                 205

Gln Arg Thr Gln Ser Asn Leu Pro Thr Ser Leu Glu Gly Leu Ser Asn
    210                 215                 220

Leu Ala Asp Val Asp Leu Ser Cys Asn Asp Leu Thr Arg Val Pro Glu
```

```
                225                 230                 235                 240
Cys Leu Tyr Thr Leu Pro Ser Leu Arg Arg Leu Asn Leu Ser Ser Asn
                    245                 250                 255

Gln Ile Thr Glu Leu Ser Leu Cys Ile Asp Gln Trp Val His Val Glu
                    260                 265                 270

Thr Leu Asn Leu Ser Arg Asn Gln Leu Thr Ser Leu Pro Ser Ala Ile
                    275                 280                 285

Cys Lys Leu Ser Lys Leu Lys Lys Leu Tyr Leu Asn Ser Asn Lys Leu
    290                 295                 300

Asp Phe Asp Gly Leu Pro Ser Gly Ile Gly Lys Leu Thr Asn Leu Glu
305                 310                 315                 320

Glu Phe Met Ala Ala Asn Asn Leu Glu Leu Val Pro Glu Ser Leu
                    325                 330                 335

Cys Arg Cys Pro Lys Leu Arg Lys Leu Val Leu Asn Lys Asn His Leu
                    340                 345                 350

Val Thr Leu Pro Glu Ala Ile His Phe Leu Thr Glu Ile Glu Val Leu
                    355                 360                 365

Asp Val Arg Glu Asn Pro Asn Leu Val Met Pro Pro Lys Pro Ala Asp
    370                 375                 380

Arg Ala Ala Glu Trp Tyr Asn Ile Asp Phe Ser Leu Gln Asn Gln Leu
385                 390                 395                 400

Arg Leu Ala Gly Ala Ser Pro Ala Thr Val Ala Ala Ala Ala Ala Ala
                    405                 410                 415

Gly Ser Gly Pro Lys Asp Pro Met Ala Arg Lys Met Arg Leu Arg Arg
                    420                 425                 430

Arg Lys Asp Ser Ala Gln Asp Gln Ala Lys Gln Val Leu Lys Gly
                    435                 440                 445

Met Ser Asp Val Ala Gln Glu Lys Asn Lys Lys Gln Glu Glu Ser Ala
                    450                 455                 460

Asp Ala Arg Ala Pro Ser Gly Lys Val Arg Arg Trp Asp Gln Gly Leu
465                 470                 475                 480

Glu Lys Pro Arg Leu Asp Tyr Ser Glu Phe Phe Thr Glu Asp Val Gly
                    485                 490                 495

Gln Leu Pro Gly Leu Thr Ile Trp Gln Ile Glu Asn Phe Val Pro Val
                    500                 505                 510

Leu Val Glu Glu Ala Phe His Gly Lys Phe Tyr Glu Ala Asp Cys Tyr
                    515                 520                 525

Ile Val Leu Lys Thr Phe Leu Asp Asp Ser Gly Ser Leu Asn Trp Glu
                    530                 535                 540

Ile Tyr Tyr Trp Ile Gly Gly Glu Ala Thr Leu Asp Lys Lys Ala Cys
545                 550                 555                 560

Ser Ala Ile His Ala Val Asn Leu Arg Asn Tyr Leu Gly Ala Glu Cys
                    565                 570                 575

Arg Thr Val Arg Glu Glu Met Gly Asp Glu Ser Glu Glu Phe Leu Gln
                    580                 585                 590

Val Phe Asp Asn Asp Ile Ser Tyr Ile Glu Gly Gly Thr Ala Ser Gly
                    595                 600                 605

Phe Tyr Thr Val Glu Asp Thr His Tyr Val Thr Arg Met Tyr Arg Val
                    610                 615                 620

Tyr Gly Lys Lys Asn Ile Lys Leu Glu Pro Val Pro Leu Lys Gly Thr
625                 630                 635                 640

Ser Leu Asp Pro Arg Phe Val Phe Leu Leu Asp Arg Gly Leu Asp Ile
                    645                 650                 655
```

-continued

Tyr Val Trp Arg Gly Ala Gln Ala Thr Leu Ser Ser Thr Thr Lys Ala
            660                 665                 670

Arg Leu Phe Ala Glu Lys Ile Asn Lys Asn Glu Arg Lys Gly Lys Ala
675                 680                 685

Glu Ile Thr Leu Leu Val Gln Gly Gln Glu Leu Pro Glu Phe Trp Glu
690                 695                 700

Ala Leu Gly Gly Glu Pro Ser Glu Ile Lys Lys His Val Pro Glu Asp
705                 710                 715                 720

Phe Trp Pro Pro Gln Pro Lys Leu Tyr Lys Val Gly Leu Gly Leu Gly
                725                 730                 735

Tyr Leu Glu Leu Pro Gln Ile Asn Tyr Lys Leu Ser Val Glu His Lys
            740                 745                 750

Gln Arg Pro Lys Val Glu Leu Met Pro Arg Met Arg Leu Leu Gln Ser
        755                 760                 765

Leu Leu Asp Thr Arg Cys Val Tyr Ile Leu Asp Cys Trp Ser Asp Val
    770                 775                 780

Phe Ile Trp Leu Gly Arg Lys Ser Pro Arg Leu Val Arg Ala Ala Ala
785                 790                 795                 800

Leu Lys Leu Gly Gln Glu Leu Cys Gly Met Leu His Arg Pro Arg His
                805                 810                 815

Ala Thr Val Ser Arg Ser Leu Glu Gly Thr Glu Ala Gln Val Phe Lys
            820                 825                 830

Ala Lys Phe Lys Asn Trp Asp Asp Val Leu Thr Val Asp Tyr Thr Arg
        835                 840                 845

Asn Ala Glu Ala Val Leu Gln Ser Pro Gly Leu Ser Gly Lys Val Lys
    850                 855                 860

Arg Asp Ala Glu Lys Lys Asp Gln Met Lys Ala Asp Leu Thr Ala Leu
865                 870                 875                 880

Phe Leu Pro Arg Gln Pro Pro Met Ser Leu Ala Glu Ala Gln Leu
                885                 890                 895

Met Glu Glu Trp Asn Glu Asp Leu Asp Gly Met Glu Gly Phe Val Leu
            900                 905                 910

Glu Gly Lys Lys Phe Ala Arg Leu Pro Glu Glu Glu Phe Gly His Phe
        915                 920                 925

Tyr Thr Gln Asp Cys Tyr Val Phe Leu Cys Arg Tyr Trp Val Pro Val
    930                 935                 940

Glu Tyr Glu Glu Glu Glu Lys Lys Glu Asp Lys Glu Glu Lys Ala Glu
945                 950                 955                 960

Gly Lys Glu Gly Glu Glu Ala Thr Ala Glu Ala Glu Lys Gln Pro
                965                 970                 975

Glu Glu Asp Phe Gln Cys Ile Val Tyr Phe Trp Gln Gly Arg Glu Ala
            980                 985                 990

Ser Asn Met Gly Trp Leu Thr Phe Thr Phe Ser Leu Gln Lys Lys Phe
        995                 1000                1005

Glu Ser Leu Phe Pro Gly Lys Leu Glu Val Val Arg Met Thr Gln
    1010                1015                1020

Gln Gln Glu Asn Pro Lys Phe Leu Ser His Phe Lys Arg Lys Phe
    1025                1030                1035

Ile Ile His Arg Gly Lys Arg Lys Ala Val Gln Gly Ala Gln Gln
    1040                1045                1050

Pro Ser Leu Tyr Gln Ile Arg Thr Asn Gly Ser Ala Leu Cys Thr
    1055                1060                1065

| | | | | | | | | | | |
|---|---|---|---|---|---|---|---|---|---|---|
| Arg | Cys | Ile | Gln | Ile | Asn | Thr | Asp | Ser | Ser | Leu | Leu | Asn | Ser | Glu |
| 1070 | | | | | 1075 | | | | | 1080 | | | | |

Arg Cys Ile Gln Ile Asn Thr Asp Ser Ser Leu Leu Asn Ser Glu
1070                1075              1080

Phe Cys Phe Ile Leu Lys Val Pro Phe Glu Ser Glu Asp Asn Gln
1085                1090              1095

Gly Ile Val Tyr Ala Trp Val Gly Arg Ala Ser Asp Pro Asp Glu
1100                1105              1110

Ala Lys Leu Ala Glu Asp Ile Leu Asn Thr Met Phe Asp Thr Ser
1115                1120              1125

Tyr Ser Lys Gln Val Ile Asn Glu Gly Glu Glu Pro Glu Asn Phe
1130                1135              1140

Phe Trp Val Gly Ile Gly Ala Gln Lys Pro Tyr Asp Asp Asp Ala
1145                1150              1155

Glu Tyr Met Lys His Thr Arg Leu Phe Arg Cys Ser Asn Glu Lys
1160                1165              1170

Gly Tyr Phe Ala Val Thr Glu Lys Cys Ser Asp Phe Cys Gln Asp
1175                1180              1185

Asp Leu Ala Asp Asp Ile Met Leu Leu Asp Asn Gly Gln Glu
1190                1195              1200

Val Tyr Met Trp Val Gly Thr Gln Thr Ser Gln Val Glu Ile Lys
1205                1210              1215

Leu Ser Leu Lys Ala Cys Gln Val Tyr Ile Gln His Met Arg Ser
1220                1225              1230

Lys Glu His Glu Arg Pro Arg Arg Leu Arg Leu Val Arg Lys Gly
1235                1240              1245

Asn Glu Gln His Ala Phe Thr Arg Cys Phe His Ala Trp Ser Ala
1250                1255              1260

Phe Cys Lys Ala Leu Ala
1265

<210> SEQ ID NO 3
<211> LENGTH: 4208
<212> TYPE: DNA
<213> ORGANISM: Homo sapiens

<400> SEQUENCE: 3

```
ttcctgtccc gctcggctcc aggccctgcg tgtcccaggg actgcggccg gggcggggtg      60
gggctctccc ctggccagga atggacctcc gaggcctccg cccagtgcct ggcggctact     120
tccctgagaa tgtcaaggcc atgaccagcc tgcggtggct gaagctgaac cgcactggcc     180
tctgctacct gcccgaggag ctggccgcct gcagaagctg gaacacttg tctgtgagcc      240
acaacaacct gaccacgctt catggggagc tgtccagcct gccatcgctg cgcgccatcg     300
tggcccgagc caacagtctg aagaattccg gagtccccga tgacatcttc aagctagatg     360
atctctcagt cctggacttg agccacaacc agctgacaga gtgcccgcgg gagctggaga     420
acgccaagaa catgctggtg ctgaacctca gccacaacag catcgacacc atccccaacc     480
agctcttcat caacctcact gacctactat acctggacct cagcgagaac cgcctggaga     540
gcctgccccc gcagatgcgc cgcctggtgc acctgcagac gctcgtgctc aatggaaacc     600
ccctgctgca tgcacagctc cggcagctcc cagcgatgac ggccctgcag acctgcacc      660
tgcggagcac ccagcgcacc cagagcaacc tgcccaccag cctggagggt ctgagcaacc     720
tcgcagacgt ggatctgtcc tgcaatgacc tgacacgggt gccgagtgt ctgtacaccc      780
tccccagcct gcgccgcctc aacctcagca gcaaccgat cacggagctg tccctgtgca     840
tagaccagtg ggtgcacgtg gaaactctga acctgtcccg aaatcagctc acctcactgc     900
```

```
cctcagccat tgcaagctg agcaagctga agaagctgta cctgaattcc aacaagctgg    960
actttgacgg gctgccctca ggcattggca agctcaccaa cctggaagag ttcatggctg   1020
ccaacaacaa cctggagctg gtccctgaaa gtctctgcag gtgcccaaag ctgaggaaac   1080
ttgtcctgaa caagaaccac ctggtgaccc tcccagaagc catccatttc ctgacggaga   1140
tcgaggtcct ggatgtgcgg gagaaccca acctggtcat gccgcccaag cccgcagacc    1200
gtgccgctga gtggtacaac atcgacttct cgctgcagaa ccagctgcgg ctagcgggtg   1260
cctctcctgc taccgtggct gcagctgcag ctgcaggag tgggcccaag gaccctatgg    1320
ctcgcaagat gcgactgcgg aggcgcaagg attcagccca ggatgaccag gccaagcagg   1380
tgctgaaggg catgtcagat gttgcccagg agaagaacaa aaagcaggag gagagcgcag   1440
atgcccgggc cccagcggg aaggtgcggc gttgggacca gggcctggag aagcccgcc    1500
ttgactactc cgagttcttc acggaggacg tgggccagct gcccggactg accatctggc   1560
agatagagaa cttcgtgcct gtgctggtgg aggaagcctt ccacggcaag ttctacgagg   1620
ctgactgcta cattgtgctc aagaccttc tggatgacag cggctccctc aactgggaga   1680
tctactactg gattggcggg gaggccacac tcgacaagaa agcttgctct gccatccacg   1740
ctgtcaactt gcgcaactac ctgggtgctg agtgccgcac tgtccgggag agatgggcg    1800
atgagagcga ggagttcctg caggtgtttg acaacgacat ctcctacatt gagggtggaa   1860
cagccagtgg cttctacact gtggaagaca cacactatgt caccaggatg tatcgtgtgt   1920
atgggaaaaa gaacatcaag ttggagcctg tgccctcaa ggggacctct ctggacccaa    1980
ggtttgtttt cctgctggac cgagggctag acatctacgt atggcggggg gcccaggcca   2040
cactgagcag caccaccaag gccaggctct tgcagagaa aattaacaag aatgagcgga   2100
aagggaaggc tgagatcaca ctgctggtgc agggccagga gctcccagag ttctgggagg   2160
cactgggtgg ggagccctct gagatcaaga agcacgtgcc tgaagacttc tggccgccgc   2220
agcccaagct gtacaaggtg ggcctgggct tgggctacct ggagctgcca cagatcaact   2280
acaagctctc cgtggaacat aagcagcgtc ccaaggtgga gctgatgcca agaatgcggc   2340
tgctgcagag tctgctggac acgcgctgcg tgtacattct ggactgttgg tccgacgtgt   2400
tcatctggct cggccgcaag tccccgcgcc tggtgcgcgc tgccgccctc aagctgggtc   2460
aggagctgtg cgggatgctg caccggccac gccatgccac ggtcagccgc agcctcgagg   2520
gcaccgaggc gcaggtgttc aaggccaagt tcaagaattg ggacgatgtg ttgacggtgg   2580
actacacacg caatgcggag gccgtgctgc agagcccggg tctctccggg aaggtgaaac   2640
gcgacgccga aagaaagac cagatgaagg ctgacctcac tgcgcttttc ctgccgcggc    2700
agccgcccat gtcgctggcc gaggcggagc agctgatgga ggagtggaac gaagacctag   2760
acggcatgga gggtttcgtg ctggagggca agaagtttgc gcggctgccg gaagaggagt   2820
ttggccactt ctacacgcag gactgctacg tcttcctctg caggtactgg gtgcctgtgg   2880
agtacgagga ggagga aaag aaggaagaca aggaggagga ggccgagggc aaagaaggcg   2940
aggaagcaac cgctgaggca gaggagaagc agccagagga ggacttccag tgcatcgtgt   3000
acttctggca gggccgtgaa gcctccaata tgggctggct caccttcacc ttcagcctgc   3060
aaaagaagtt cgagagcctc ttccctggga agctggaggt ggtacgcatg acgcagcagc   3120
aggagaaccc caagttcctg tcccatttca agaggaagtt catcatccac cggggcaaga   3180
ggaaggcggt ccagggcgcc caacagccca gcctctacca gatccgcacc aacggcagcg   3240
```

-continued

```
ccctctgcac ccggtgcatc cagatcaaca ccgactccag cctcctcaac tccgagttct    3300
gcttcatcct caaggttccc tttgagagtg aggacaacca gggcatcgtg tatgcctggg    3360
tgggccgggc atcagaccct gacgaagcca agttggcaga agacatcctg aacaccatgt    3420
ttgacacctc ctacagcaag caggttatca acgaaggtga ggagcctgag aacttcttct    3480
gggtgggcat tggggcacag aagccctatg atgacgatgc cgagtacatg aaacacacac    3540
gtctcttccg gtgctccaac gagaagggct actttgcagt gactgagaaa tgctccgact    3600
tttgccaaga tgacctggca gatgatgaca tcatgttgct agacaatggc caagaggtct    3660
acatgtgggt ggggacccag actagccagg tggagatcaa gctgagcctg aaggcctgcc    3720
aggtatatat ccagcacatg cggtccaagg aacatgagcg gccgcgccgg ctgcgcctgg    3780
tccgcaaggg caatgagcag cacgccttta cccgctgctt ccacgcctgg agcgccttct    3840
gcaaggccct ggcctaagac aggctggcac agccccaggc ttggtgagga agaggaaggg    3900
gcctcatcca ctgtctgcta gcaaagaatg tactcaggtg acaccacctg ctccagccac    3960
gtccagtgcc acagtcccca gtagcctcaa gcagcaccaa tgggatgac cctgacaggt    4020 gccctcaggg gtctgggaaa tccaactctc tccacagtgt gagtgcacgt gtgaagcccc    4080
ctcactcttc cgctagggat aaagcagatg tggatgccct ttaagagata ttaaatgctt    4140 ttatttttcaa tattaaaaat cagtattttt aatattaaaa aaaaaaaaaa aaaaaaaaa    4200 aaaaaaaa                                                             4208
```

<210> SEQ ID NO 4
<211> LENGTH: 1258
<212> TYPE: PRT
<213> ORGANISM: Homo sapiens

<400> SEQUENCE: 4

```
Met Asp Leu Arg Gly Leu Arg Pro Val Pro Gly Gly Tyr Phe Pro Glu
 1               5                  10                  15

Asn Val Lys Ala Met Thr Ser Leu Arg Trp Leu Lys Leu Asn Arg Thr
            20                  25                  30

Gly Leu Cys Tyr Leu Pro Glu Glu Leu Ala Ala Leu Gln Lys Leu Glu
        35                  40                  45

His Leu Ser Val Ser His Asn Asn Leu Thr Thr Leu His Gly Glu Leu
    50                  55                  60

Ser Ser Leu Pro Ser Leu Arg Ala Ile Val Ala Arg Ala Asn Ser Leu
65                  70                  75                  80

Lys Asn Ser Gly Val Pro Asp Asp Ile Phe Lys Leu Asp Asp Leu Ser
                85                  90                  95

Val Leu Asp Leu Ser His Asn Gln Leu Thr Glu Cys Pro Arg Glu Leu
            100                 105                 110

Glu Asn Ala Lys Asn Met Leu Val Leu Asn Leu Ser His Asn Ser Ile
        115                 120                 125

Asp Thr Ile Pro Asn Gln Leu Phe Ile Asn Leu Thr Asp Leu Leu Tyr
    130                 135                 140

Leu Asp Leu Ser Glu Asn Arg Leu Glu Ser Leu Pro Pro Gln Met Arg
145                 150                 155                 160

Arg Leu Val His Leu Gln Thr Leu Val Leu Asn Gly Asn Pro Leu Leu
                165                 170                 175

His Ala Gln Leu Arg Gln Leu Pro Ala Met Thr Ala Leu Gln Thr Leu
            180                 185                 190

His Leu Arg Ser Thr Gln Arg Thr Gln Ser Asn Leu Pro Thr Ser Leu
```

-continued

```
            195                 200                 205
Glu Gly Leu Ser Asn Leu Ala Asp Val Asp Leu Ser Cys Asn Asp Leu
210                 215                 220
Thr Arg Val Pro Glu Cys Leu Tyr Thr Leu Pro Ser Leu Arg Arg Leu
225                 230                 235                 240
Asn Leu Ser Ser Asn Gln Ile Thr Glu Leu Ser Leu Cys Ile Asp Gln
                245                 250                 255
Trp Val His Val Glu Thr Leu Asn Leu Ser Arg Asn Gln Leu Thr Ser
                260                 265                 270
Leu Pro Ser Ala Ile Cys Lys Leu Ser Lys Leu Lys Leu Tyr Leu
            275                 280                 285
Asn Ser Asn Lys Leu Asp Phe Asp Gly Leu Pro Ser Gly Ile Gly Lys
290                 295                 300
Leu Thr Asn Leu Glu Glu Phe Met Ala Ala Asn Asn Leu Glu Leu
305                 310                 315                 320
Val Pro Glu Ser Leu Cys Arg Cys Pro Lys Leu Arg Lys Leu Val Leu
                325                 330                 335
Asn Lys Asn His Leu Val Thr Leu Pro Glu Ala Ile His Phe Leu Thr
                340                 345                 350
Glu Ile Glu Val Leu Asp Val Arg Glu Asn Pro Asn Leu Val Met Pro
            355                 360                 365
Pro Lys Pro Ala Asp Arg Ala Ala Glu Trp Tyr Asn Ile Asp Phe Ser
370                 375                 380
Leu Gln Asn Gln Leu Arg Leu Ala Gly Ala Ser Pro Ala Thr Val Ala
385                 390                 395                 400
Ala Ala Ala Ala Gly Ser Gly Pro Lys Asp Pro Met Ala Arg Lys
                405                 410                 415
Met Arg Leu Arg Arg Arg Lys Asp Ser Ala Gln Asp Gln Ala Lys
                420                 425                 430
Gln Val Leu Lys Gly Met Ser Asp Val Ala Gln Glu Lys Asn Lys Lys
            435                 440                 445
Gln Glu Glu Ser Ala Asp Ala Arg Ala Pro Ser Gly Lys Val Arg Arg
450                 455                 460
Trp Asp Gln Gly Leu Glu Lys Pro Arg Leu Asp Tyr Ser Glu Phe Phe
465                 470                 475                 480
Thr Glu Asp Val Gly Gln Leu Pro Gly Leu Thr Ile Trp Gln Ile Glu
                485                 490                 495
Asn Phe Val Pro Val Leu Val Glu Glu Ala Phe His Gly Lys Phe Tyr
                500                 505                 510
Glu Ala Asp Cys Tyr Ile Val Leu Lys Thr Phe Leu Asp Asp Ser Gly
            515                 520                 525
Ser Leu Asn Trp Glu Ile Tyr Tyr Trp Ile Gly Gly Glu Ala Thr Leu
            530                 535                 540
Asp Lys Lys Ala Cys Ser Ala Ile His Ala Val Asn Leu Arg Asn Tyr
545                 550                 555                 560
Leu Gly Ala Glu Cys Arg Thr Val Arg Glu Glu Met Gly Asp Glu Ser
                565                 570                 575
Glu Glu Phe Leu Gln Val Phe Asp Asn Asp Ile Ser Tyr Ile Glu Gly
                580                 585                 590
Gly Thr Ala Ser Gly Phe Tyr Thr Val Glu Asp Thr His Tyr Val Thr
            595                 600                 605
Arg Met Tyr Arg Val Tyr Gly Lys Lys Asn Ile Lys Leu Glu Pro Val
            610                 615                 620
```

-continued

```
Pro Leu Lys Gly Thr Ser Leu Asp Pro Arg Phe Val Phe Leu Leu Asp
625                 630                 635                 640

Arg Gly Leu Asp Ile Tyr Val Trp Arg Gly Ala Gln Ala Thr Leu Ser
            645                 650                 655

Ser Thr Thr Lys Ala Arg Leu Phe Ala Glu Lys Ile Asn Lys Asn Glu
                660                 665                 670

Arg Lys Gly Lys Ala Glu Ile Thr Leu Leu Val Gln Gly Gln Glu Leu
        675                 680                 685

Pro Glu Phe Trp Glu Ala Leu Gly Gly Glu Pro Ser Glu Ile Lys Lys
    690                 695                 700

His Val Pro Glu Asp Phe Trp Pro Pro Gln Lys Leu Tyr Lys Val
705                 710                 715                 720

Gly Leu Gly Leu Gly Tyr Leu Glu Leu Pro Gln Ile Asn Tyr Lys Leu
            725                 730                 735

Ser Val Glu His Lys Gln Arg Pro Lys Val Glu Leu Met Pro Arg Met
                740                 745                 750

Arg Leu Leu Gln Ser Leu Leu Asp Thr Arg Cys Val Tyr Ile Leu Asp
        755                 760                 765

Cys Trp Ser Asp Val Phe Ile Trp Leu Gly Arg Lys Ser Pro Arg Leu
    770                 775                 780

Val Arg Ala Ala Ala Leu Lys Leu Gly Gln Glu Leu Cys Gly Met Leu
785                 790                 795                 800

His Arg Pro Arg His Ala Thr Val Ser Arg Ser Leu Glu Gly Thr Glu
                805                 810                 815

Ala Gln Val Phe Lys Ala Lys Phe Lys Asn Trp Asp Asp Val Leu Thr
        820                 825                 830

Val Asp Tyr Thr Arg Asn Ala Glu Ala Val Leu Gln Ser Pro Gly Leu
    835                 840                 845

Ser Gly Lys Val Lys Arg Asp Ala Glu Lys Asp Gln Met Lys Ala
850                 855                 860

Asp Leu Thr Ala Leu Phe Leu Pro Arg Gln Pro Pro Met Ser Leu Ala
865                 870                 875                 880

Glu Ala Glu Gln Leu Met Glu Glu Trp Asn Asp Leu Asp Gly Met
                885                 890                 895

Glu Gly Phe Val Leu Glu Gly Lys Lys Phe Ala Arg Leu Pro Glu Glu
        900                 905                 910

Glu Phe Gly His Phe Tyr Thr Gln Asp Cys Tyr Val Phe Leu Cys Arg
    915                 920                 925

Tyr Trp Val Pro Val Glu Tyr Glu Glu Glu Lys Lys Glu Asp Lys
930                 935                 940

Glu Glu Lys Ala Glu Gly Lys Glu Gly Glu Ala Thr Ala Glu Ala
945                 950                 955                 960

Glu Glu Lys Gln Pro Glu Glu Asp Phe Gln Cys Ile Val Tyr Phe Trp
                965                 970                 975

Gln Gly Arg Glu Ala Ser Asn Met Gly Trp Leu Thr Phe Thr Phe Ser
        980                 985                 990

Leu Gln Lys Lys Phe Glu Ser Leu Phe Pro Gly Lys Leu Glu Val Val
    995                 1000                1005

Arg Met Thr Gln Gln Gln Glu Asn Pro Lys Phe Leu Ser His Phe
        1010                1015                1020

Lys Arg Lys Phe Ile Ile His Arg Gly Leu Arg Lys Ala Val Gln
    1025                1030                1035
```

Gly Ala Gln Gln Pro Ser Leu Tyr Gln Ile Arg Thr Asn Gly Ser
1040            1045                1050

Ala Leu Cys Thr Arg Cys Ile Gln Ile Asn Thr Asp Ser Ser Leu
1055            1060                1065

Leu Asn Ser Glu Phe Cys Phe Ile Leu Lys Val Pro Phe Glu Ser
1070            1075                1080

Glu Asp Asn Gln Gly Ile Val Tyr Ala Trp Val Gly Arg Ala Ser
1085            1090                1095

Asp Pro Asp Glu Ala Lys Leu Ala Glu Asp Ile Leu Asn Thr Met
1100            1105                1110

Phe Asp Thr Ser Tyr Ser Lys Gln Val Ile Asn Glu Gly Glu Glu
1115            1120                1125

Pro Glu Asn Phe Phe Trp Val Gly Ile Gly Ala Gln Lys Pro Tyr
1130            1135                1140

Asp Asp Asp Ala Glu Tyr Met Lys His Thr Arg Leu Phe Arg Cys
1145            1150                1155

Ser Asn Glu Lys Gly Tyr Phe Ala Val Thr Glu Lys Cys Ser Asp
1160            1165                1170

Phe Cys Gln Asp Asp Leu Ala Asp Asp Asp Ile Met Leu Leu Asp
1175            1180                1185

Asn Gly Gln Glu Val Tyr Met Trp Val Gly Thr Gln Thr Ser Gln
1190            1195                1200

Val Glu Ile Lys Leu Ser Leu Lys Ala Cys Gln Val Tyr Ile Gln
1205            1210                1215

His Met Arg Ser Lys Glu His Glu Arg Pro Arg Arg Leu Arg Leu
1220            1225                1230

Val Arg Lys Gly Asn Glu Gln His Ala Phe Thr Arg Cys Phe His
1235            1240                1245

Ala Trp Ser Ala Phe Cys Lys Ala Leu Ala
1250            1255

<210> SEQ ID NO 5
<211> LENGTH: 4222
<212> TYPE: DNA
<213> ORGANISM: Homo sapiens

<400> SEQUENCE: 5
aactccagca caggggggc ccgcactcct tggtgcctcc gcagtcttcg aacagacggg     60
gaaactgagg ccctaagagg cctaaagcct acacttcccc gcggaatgcg gcgggcgcgg    120
gcgggttaaa ggggcgggc cggcgctggc ccagcccgcg gctcccccca gcgccctcgc    180
cccggcgctc cctagcccgg cgcggcccgg cagcgagagc ggcgccatgg aggccaccgg    240
ggtgctgccg ttcgtgcgtg gcgtggacct cagcggcaac gacttcaagg gcggctactt    300
ccctgagaat gtcaaggcca tgaccagcct gcggtggctg aagctgaacc gcactggcct    360
ctgctacctg cccgaggagc tggccgcccc gcagaagctg aacacttgt ctgtgagcca    420 caacaacctg accacgcttc atgggagct gtccagcctg ccatcgctgc gcgccatcgt    480
ggcccgagcc aacagtctga gaattccgg agtccccgat gacatcttca agctagatga    540
tctctcagtc ctggacttga gccacaacca gctgacagag tgcccgcggg agctggagaa    600
cgccaagaac atgctggtgc tgaacctcag ccacaacagg cagctcccag cgatgacggc    660
cctgcagacc ctgcacctgc ggagcaccca gcgcacccag agcaacctgc caccagcctt    720
ggagggtctg agcaacctcg cagacgtgga tctgtcctgc aatgacctga cacgggtgcc    780

```
cgagtgtctg tacaccctcc ccagcctgcg ccgcctcaac ctcagcagca accagatcac    840
ggagctgtcc ctgtgcatag accagtgggt gcacgtggaa actctgaacc tgtcccgaaa    900
tcagctcacc tcactgccct cagccatttg caagctgagc aagctgaaga agctgtacct    960
gaattccaac aagctggact ttgacgggct gccctcaggc attggcaagc tcaccaacct   1020
ggaagagttc atggctgcca caacaacct ggagctggtc cctgaaagtc tctgcaggtg    1080
cccaaagctg aggaaacttg tcctgaacaa gaaccacctg gtgaccctcc agaagccat    1140 ccatttcctg acggagatcg aggtcctgga tgtgcgggag aaccccaacc tggtcatgcc   1200
gcccaagccc gcagaccgtg ccgctgagtg gtacaacatc gacttctcgc tgcagaacca   1260
gctgcggcta gcgggtgcct ctcctgctac cgtggctgca gctgcagctg ggagtgggcc   1320
caaggaccct atggctcgca agatgcgact gcggaggcgc aaggattcag cccaggatga   1380
ccaggccaag caggtgctga agggcatgtc agatgttgcc caggagaaga acaaaaagca   1440
ggaggagagc gcagatgccc gggccccag cgggaaggtg cggcgttggg accagggcct    1500
ggagaagccc cgccttgact actccgagtt cttcacggag gacgtgggcc agctgcccgg   1560
actgaccatc tggcagatag agaacttcgt gcctgtgctg gtggaggaag ccttccacgg   1620
caagttctac gaggctgact gctacattgt gctcaagacc tttctggatg acagcggctc   1680
cctcaactgg gagatctact actggattgg cggggaggcc acactcgaca gaaaagcttg   1740
ctctgccatc cacgctgtca acttgcgcaa ctacctgggt gctgagtgcc gcactgtccg   1800
ggaggagatg ggcgatgaga gcgaggagtt cctgcaggtg tttgacaacg acatctccta   1860
cattgagggt ggaacagcca gtggcttcta cactgtggaa gacacacact atgtcaccag   1920
gatgtatcgt gtgtatggga aaaagaacat caagttggag cctgtgcccc tcaaggggac   1980
ctctctggac ccaaggtttg ttttcctgct ggaccgaggg ctagacatct acgtatggcg   2040
gggggcccag gccacactga gcagcaccac caaggccagg ctctttgcag agaaaattaa   2100
caagaatgag cggaaaggga aggctgagat cacactgctg gtgcagggcc aggagctccc   2160
agagttctgg gaggcactgg gtggggagcc ctctgagatc aagaagcacg tgcctgaaga   2220 cttctgggccg ccgcagccca gctgtacaa ggtgggcctg ggcttgggct acctggagct    2280
gccacagatc aactacaagc tctccgtgga acataagcag cgtcccaagg tggagctgat   2340
gccaagaatg cggctgctgc agagtctgct ggacacgcgc tgcgtgtaca ttctggactg   2400
ttggtccgac gtgttcatct ggctcggccg caagtccccg cgcctggtgc gcgctgccgc   2460
cctcaagctg ggtcaggagc tgtgcgggat gctgcaccgg ccacgccatg ccacggtcag   2520
ccgcagcctc gagggcaccg aggcgcaggt gttcaaggcc aagttcaaga attgggacga   2580
tgtgttgacg gtggactaca cacgcaatgc ggaggccgtg ctgcagagcc cgggtctctc   2640
cgggaaggtg aaacgcgacg ccgagaagaa agaccagatg aaggctgacc tcactgcgct   2700
tttcctgccg cggcagccgc ccatgtcgct ggccgaggcg gagcagctga tggaggagtg   2760
gaacgaagac ctagacggca tggagggttt cgtgctggag ggcaagaagt tgcgcggct    2820 gccggaagag gagtttggcc acttctacac gcaggactgc tacgtcttcc tctgcaggta   2880
ctgggtgcct gtggagtacg aggaggagga aagaaggaa gacaaggagg agaaggccga    2940
gggcaaagaa ggcgaggaag caaccgctga ggcagaggag aagcagccag aggaggactt   3000
ccagtgcatc gtgtacttct ggcagggccg tgaagcctcc aatatgggct ggctcacctt   3060
caccttcagc ctgcaaaaga agttcgagag cctcttccct gggaagctgg aggtggtacg   3120
catgacgcag cagcaggaga accccaagtt cctgtcccat ttcaagagga agttcatcat   3180
```

-continued

```
ccaccggggc aagaggaagg cggtccaggg cgcccaacag cccagcctct accagatccg   3240
caccaacggc agcgccctct gcacccggtg catccagatc aacaccgact ccagcctcct   3300
caactccgag ttctgcttca tcctcaaggt tcccttgag agtgaggaca accagggcat    3360
cgtgtatgcc tgggtgggcc gggcatcaga ccctgacgaa gccaagttgg cagaagacat   3420
cctgaacacc atgtttgaca cctcctacag caagcaggtt atcaacgaag gtgaggagcc   3480
tgagaacttc ttctgggtgg gcattggggc acagaagccc tatgatgacg atgccgagta   3540
catgaaacac acacgtctct tccggtgctc caacgagaag ggctactttg cagtgactga   3600
gaaatgctcc gacttttgcc aagatgacct ggcagatgat gacatcatgt tgctagacaa   3660
tggccaagag gtctacatgt gggtggggac ccagactagc caggtggaga tcaagctgag   3720
cctgaaggc tgccaggtat atatccagca catgcggtcc aaggaacatg agcggccgcg    3780
ccggctgcgc ctggtccgca agggcaatga gcagcacgcc tttacccgct gcttccacgc   3840
ctggagcgcc ttctgcaagg ccctggccta agacaggctg gcacagcccc aggcttggtg   3900
aggaagagga aggggcctca tccactgtct gctagcaaag aatgtactca ggtgacacca   3960
cctgctccag ccacgtccag tgccacagtc cccagtagcc tcaagcagca ccaatgggga   4020
tgaccctgac aggtgccctc aggggtctgg gaaatccaac tctctccaca gtgtgagtgc   4080
acgtgtgaag cccctcact cttccgctag ggataaagca gatgtggatg cccttaaga    4140
gatattaaat gcttttattt tcaatattaa aaatcagtat ttttaatatt aaaaaaaaaa   4200
aaaaaaaaaa aaaaaaaaaa aa                                            4222
```

<210> SEQ ID NO 6
<211> LENGTH: 1214
<212> TYPE: PRT
<213> ORGANISM: Homo sapiens

<400> SEQUENCE: 6

```
Met Glu Ala Thr Gly Val Leu Pro Phe Val Arg Gly Val Asp Leu Ser
1               5                   10                  15

Gly Asn Asp Phe Lys Gly Gly Tyr Phe Pro Glu Asn Val Lys Ala Met
            20                  25                  30

Thr Ser Leu Arg Trp Leu Lys Leu Asn Arg Thr Gly Leu Cys Tyr Leu
        35                  40                  45

Pro Glu Glu Leu Ala Ala Leu Gln Lys Leu Glu His Leu Ser Val Ser
    50                  55                  60

His Asn Asn Leu Thr Thr Leu His Gly Glu Leu Ser Ser Leu Pro Ser
65                  70                  75                  80

Leu Arg Ala Ile Val Ala Arg Ala Asn Ser Leu Lys Asn Ser Gly Val
                85                  90                  95

Pro Asp Asp Ile Phe Lys Leu Asp Asp Leu Ser Val Leu Asp Leu Ser
            100                 105                 110

His Asn Gln Leu Thr Glu Cys Pro Arg Glu Leu Glu Asn Ala Lys Asn
        115                 120                 125

Met Leu Val Leu Asn Leu Ser His Asn Arg Gln Leu Pro Ala Met Thr
    130                 135                 140

Ala Leu Gln Thr Leu His Leu Arg Ser Thr Gln Arg Thr Gln Ser Asn
145                 150                 155                 160

Leu Pro Thr Ser Leu Glu Gly Leu Ser Asn Leu Ala Asp Val Asp Leu
                165                 170                 175

Ser Cys Asn Asp Leu Thr Arg Val Pro Glu Cys Leu Tyr Thr Leu Pro
```

```
                180                 185                 190
Ser Leu Arg Arg Leu Asn Leu Ser Ser Asn Gln Ile Thr Glu Leu Ser
            195                 200                 205

Leu Cys Ile Asp Gln Trp Val His Val Glu Thr Leu Asn Leu Ser Arg
        210                 215                 220

Asn Gln Leu Thr Ser Leu Pro Ser Ala Ile Cys Lys Leu Ser Lys Leu
225                 230                 235                 240

Lys Lys Leu Tyr Leu Asn Ser Asn Lys Leu Asp Phe Asp Gly Leu Pro
                245                 250                 255

Ser Gly Ile Gly Lys Leu Thr Asn Leu Glu Glu Phe Met Ala Ala Asn
            260                 265                 270

Asn Asn Leu Glu Leu Val Pro Glu Ser Leu Cys Arg Cys Pro Lys Leu
        275                 280                 285

Arg Lys Leu Val Leu Asn Lys Asn His Leu Val Thr Leu Pro Glu Ala
        290                 295                 300

Ile His Phe Leu Thr Glu Ile Glu Val Leu Asp Val Arg Glu Asn Pro
305                 310                 315                 320

Asn Leu Val Met Pro Pro Lys Pro Ala Asp Arg Ala Ala Glu Trp Tyr
                325                 330                 335

Asn Ile Asp Phe Ser Leu Gln Asn Gln Leu Arg Leu Ala Gly Ala Ser
            340                 345                 350

Pro Ala Thr Val Ala Ala Ala Ala Gly Ser Gly Pro Lys Asp Pro
        355                 360                 365

Met Ala Arg Lys Met Arg Leu Arg Arg Lys Asp Ser Ala Gln Asp
        370                 375                 380

Asp Gln Ala Lys Gln Val Leu Lys Gly Met Ser Asp Val Ala Gln Glu
385                 390                 395                 400

Lys Asn Lys Lys Gln Glu Glu Ser Ala Asp Ala Arg Ala Pro Ser Gly
                405                 410                 415

Lys Val Arg Arg Trp Asp Gln Gly Leu Glu Lys Pro Arg Leu Asp Tyr
            420                 425                 430

Ser Glu Phe Phe Thr Glu Asp Val Gly Gln Leu Pro Gly Leu Thr Ile
        435                 440                 445

Trp Gln Ile Glu Asn Phe Val Pro Val Leu Val Glu Glu Ala Phe His
        450                 455                 460

Gly Lys Phe Tyr Glu Ala Asp Cys Tyr Ile Val Leu Lys Thr Phe Leu
465                 470                 475                 480

Asp Asp Ser Gly Ser Leu Asn Trp Glu Ile Tyr Tyr Trp Ile Gly Gly
                485                 490                 495

Glu Ala Thr Leu Asp Lys Lys Ala Cys Ser Ala Ile His Ala Val Asn
            500                 505                 510

Leu Arg Asn Tyr Leu Gly Ala Glu Cys Arg Thr Val Arg Glu Glu Met
        515                 520                 525

Gly Asp Glu Ser Glu Glu Phe Leu Gln Val Phe Asp Asn Asp Ile Ser
        530                 535                 540

Tyr Ile Glu Gly Gly Thr Ala Ser Gly Phe Tyr Thr Val Glu Asp Thr
545                 550                 555                 560

His Tyr Val Thr Arg Met Tyr Arg Val Tyr Gly Lys Lys Asn Ile Lys
                565                 570                 575

Leu Glu Pro Val Pro Leu Lys Gly Thr Ser Leu Asp Pro Arg Phe Val
            580                 585                 590

Phe Leu Leu Asp Arg Gly Leu Asp Ile Tyr Val Trp Arg Gly Ala Gln
        595                 600                 605
```

```
Ala Thr Leu Ser Ser Thr Thr Lys Ala Arg Leu Phe Ala Glu Lys Ile
    610                 615                 620
Asn Lys Asn Glu Arg Lys Gly Lys Ala Glu Ile Thr Leu Leu Val Gln
625                 630                 635                 640
Gly Gln Glu Leu Pro Glu Phe Trp Glu Ala Leu Gly Gly Glu Pro Ser
                645                 650                 655
Glu Ile Lys Lys His Val Pro Glu Asp Phe Trp Pro Gln Pro Lys
            660                 665                 670
Leu Tyr Lys Val Gly Leu Gly Leu Gly Tyr Leu Glu Leu Pro Gln Ile
        675                 680                 685
Asn Tyr Lys Leu Ser Val Glu His Lys Gln Arg Pro Lys Val Glu Leu
690                 695                 700
Met Pro Arg Met Arg Leu Leu Gln Ser Leu Leu Asp Thr Arg Cys Val
705                 710                 715                 720
Tyr Ile Leu Asp Cys Trp Ser Asp Val Phe Ile Trp Leu Gly Arg Lys
                725                 730                 735
Ser Pro Arg Leu Val Arg Ala Ala Leu Lys Leu Gly Gln Glu Leu
            740                 745                 750
Cys Gly Met Leu His Arg Pro Arg His Ala Thr Val Ser Arg Ser Leu
        755                 760                 765
Glu Gly Thr Glu Ala Gln Val Phe Lys Ala Lys Phe Lys Asn Trp Asp
770                 775                 780
Asp Val Leu Thr Val Asp Tyr Thr Arg Asn Ala Glu Ala Val Leu Gln
785                 790                 795                 800
Ser Pro Gly Leu Ser Gly Lys Val Lys Arg Asp Ala Glu Lys Lys Asp
                805                 810                 815
Gln Met Lys Ala Asp Leu Thr Ala Leu Phe Leu Pro Arg Gln Pro Pro
            820                 825                 830
Met Ser Leu Ala Glu Ala Glu Gln Leu Met Glu Glu Trp Asn Glu Asp
        835                 840                 845
Leu Asp Gly Met Glu Gly Phe Val Leu Glu Gly Lys Lys Phe Ala Arg
850                 855                 860
Leu Pro Glu Glu Glu Phe Gly His Phe Tyr Thr Gln Asp Cys Tyr Val
865                 870                 875                 880
Phe Leu Cys Arg Tyr Trp Val Pro Val Glu Tyr Glu Glu Glu Lys
                885                 890                 895
Lys Glu Asp Lys Glu Glu Lys Ala Glu Gly Lys Glu Gly Glu Glu Ala
            900                 905                 910
Thr Ala Glu Ala Glu Lys Gln Pro Glu Glu Asp Phe Gln Cys Ile
        915                 920                 925
Val Tyr Phe Trp Gln Gly Arg Glu Ala Ser Asn Met Gly Trp Leu Thr
930                 935                 940
Phe Thr Phe Ser Leu Gln Lys Lys Phe Glu Ser Leu Phe Pro Gly Lys
945                 950                 955                 960
Leu Glu Val Val Arg Met Thr Gln Gln Gln Glu Asn Pro Lys Phe Leu
                965                 970                 975
Ser His Phe Lys Arg Lys Phe Ile Ile His Arg Gly Lys Arg Lys Ala
            980                 985                 990
Val Gln Gly Ala Gln Gln Pro Ser Leu Tyr Gln Ile Arg Thr Asn Gly
        995                 1000                1005
Ser Ala Leu Cys Thr Arg Cys Ile Gln Ile Asn Thr Asp Ser Ser
    1010                1015                1020
```

| | | | | | | | | | | | |
|---|---|---|---|---|---|---|---|---|---|---|---|
|Leu|Leu<br>1025|Asn|Ser|Glu|Phe<br>1030|Cys|Phe|Ile|Leu<br>1035|Lys|Val|Pro|Phe|Glu|

Leu Leu Asn Ser Glu Phe Cys Phe Ile Leu Lys Val Pro Phe Glu
    1025                        1030                        1035

Ser Glu Asp Asn Gln Gly Ile Val Tyr Ala Trp Val Gly Arg Ala
    1040                        1045                        1050

Ser Asp Pro Asp Glu Ala Lys Leu Ala Glu Asp Ile Leu Asn Thr
    1055                        1060                        1065

Met Phe Asp Thr Ser Tyr Ser Lys Gln Val Ile Asn Glu Gly Glu
    1070                        1075                        1080

Glu Pro Glu Asn Phe Phe Trp Val Gly Ile Gly Ala Gln Lys Pro
    1085                        1090                        1095

Tyr Asp Asp Ala Glu Tyr Met Lys His Thr Arg Leu Phe Arg
    1100                        1105                        1110

Cys Ser Asn Glu Lys Gly Tyr Phe Ala Val Thr Glu Lys Cys Ser
    1115                        1120                        1125

Asp Phe Cys Gln Asp Asp Leu Ala Asp Asp Ile Met Leu Leu
    1130                        1135                        1140

Asp Asn Gly Gln Glu Val Tyr Met Trp Val Gly Thr Gln Thr Ser
    1145                        1150                        1155

Gln Val Glu Ile Lys Leu Ser Leu Lys Ala Cys Gln Val Tyr Ile
    1160                        1165                        1170

Gln His Met Arg Ser Lys Glu His Glu Arg Pro Arg Arg Leu Arg
    1175                        1180                        1185

Leu Val Arg Lys Gly Asn Glu Gln His Ala Phe Thr Arg Cys Phe
    1190                        1195                        1200

His Ala Trp Ser Ala Phe Cys Lys Ala Leu Ala
    1205                        1210

<210> SEQ ID NO 7
<211> LENGTH: 4109
<212> TYPE: DNA
<213> ORGANISM: Homo sapiens

<400> SEQUENCE: 7

```
cgggccgggg cggcgcgagc ggctggagca acgggccccg cggcagctgc gggcgacgcg    60
gtcgatggac atgggcaccc agggatcggg gcgcaagcgg ctccccaacc gggagcggct   120
cacggcggag gacgacgcgc tcaaccagat cgcgcgggag gcggaagccc ggctcgctgc   180
aaaacgggcg gcccgcgcgg aggctcgcga gatccgcatg aaggagctgg agcggcagca   240
gaaggagatc tatcaggtcc aaaagaaata ttatgggctg gatacaaaat ggggtgacat   300
cgagcagtgg atggaagaca gtgagcgcta ctctcgtaga tccagaagaa acacatcggc   360
ttctgatgaa gacgagcgca tgtcagtggg tagtcgtgga agcctgaggt cgcagcctga   420
cttggagtat gggggtccct tacgcctgga aaatggttat gatggagaat gtatgatgc   480
acagtccctg aatagaagat ctggcaggcc ctcctgtctg tacagcgctg cccggccttc   540
ggggagttac cgggcgtctg tgttggatga aggcagcttc ggtgggaccc gacggggcag   600
cacctccggc tcccgtgctc cctcggagta cagcggccac ctcaactcca gctcccgcgc   660
ctcctccagg gccagctcgg cccgggccag ccctgtggta aagagagac cagaaaaaga   720
ttttactgag aaggggtctc gtaacatgcc gggcctgtct gcagccacgc tggcctctct   780
gggtgggact tcctctcgga gaggcagcgg agacacctcc atctccatcg acaccgaggc   840
atccatcagg gaaatcaagg aactcaatga gttaaaggac cagattcagg atgtagaagg   900
caaatacatg cagggattga agagatgaa ggactctcta gcagaagttg aagagaaata   960
```

```
taagaaggct atggtttcca atgctcagct agacaatgaa agacaaaact tcatgtacca      1020
ggttgatacc ctaaaagata tgttgctgga gcttgaagaa cagctggctg aatctaggcg      1080
gcagtacgaa gagaaaaaca aagaatttga agggaaaaa cacgcccaca gtatactgca      1140
atttcagttt gctgaagtca aggaggccct gaagcaaaga gaggaaatgc tcgaggaaat      1200
ccgacagcta cagcagaaac aggcgagttc tatcagggag atttctgatc ttcaggaaac      1260
aatagagtgg aaagacaaaa agataggggc attagagagg cagaaagagt tctttgattc      1320
cgtaaggagt gaacgggatg atcttagaga agaagtagtc atgctgaaag aggaattaaa      1380
gaaacatgga ataatcctaa attcagaaat agctaccaat ggagagactt ccgacaccct      1440
caataatgtt ggataccaag gtcctaccaa gatgacaaaa gaagagttaa atgccctcaa      1500
gtcgacaggg gatgggaccc tagatattag gttgaaaaag ctggttgatg aacgggaatg      1560
cttattggaa cagattaaga aactcaaagg gcagctggag gagagacaga agattggcaa      1620
actagacaat cttcgatctg aagatgatgt cttggaaaac gggacagaca tgcatgtaat      1680
ggacctacaa agggatgcca acagacagat cagcgacctc aaatttaaac ttgcaaaatc      1740
tgagcaagag ataactgcat agaacaaaa tgtaataagg ttagagagtc aagtatcacg      1800
ttacaaatca gcggctgaaa atgcagaaaa atagagaat gaacttaagg cagaaaaacg      1860
gaaactccaa agagagctcc gctctgcatt ggataaaaca aagagctcg aggtgagcaa      1920 cggccactta gtgaagcgtc tggaaaaaat gaaagcaaat cggagtgcac tcttgtccca      1980
gcagtaaatt ccagctctga tcaggcaact ggttggtgac tggagagcat tgtttcatag      2040
gcttttctct gtcctatctg ggagcgctgc ttcttcccct gccttccgag agacgaagac      2100
cgtggcgagc ttggcgctta ggggctcccg tgccatggct caccccaggg agccccagca      2160
gccaccaggt gcctctgtct gcagacccct ggcccgggct ggcgccgacg ctcagaacct      2220
gcaggtactt cataagcaca caggggcctc gagggagctc tgtgtctgac cgcacagcag      2280
cctctgaatg ccgctggaag tgatgatcaa agtaaagatt cagttgggac ttgagttttt      2340 ttttttttc atgtgtcttg ctgaagatta aggggaaatg ttacagtgtt gggacttcct      2400
ttcatggcag aatctacaat ttgagcgact tcagtagtat ctcttagtct acgcttttca      2460
tacacaaaac actgtggaac cacaagccat taccaagcaa aactctttca ctggaaacaa      2520 ggggcagtc tagaagtaaa agtgaccta agaagactct ttacaggcaa caatgaagc      2580 ttttctaagg gatttttgca tcagttcagt cataagaata cttttttcca gggtaattag      2640
gcaatagctt cactgaaaat gacagctttt cattgcatta tttaatcctt atatttggaa      2700
ttgaagtcgt taacttcttt taaagaatgt actattgaa aaattaaaaa tgaaatgttg      2760
agagacttca gcaatgtggt tctaattttt ttccactgag aaagaagatc tttaatttca      2820
tattaatggt tctgtatatt ttgggtcatc ttttattt ttaagaatat caagtcaatt      2880
catttttctt tccctattta aaaaaaagg tgttttcaca gaatgagtgc acttaaaaag      2940
tgaagtgaag gaggaggtaa cagtagagac gatggcaata tcatcaagga caaaagtaaa      3000
aacgtttagc tacctgctga tttttagtga ctgttcatat atgttgtatt tcaagtatgg      3060
ctggtgaagc cagtcagctt ttcgggacgt tagcaagtgg aaactgagtc agtatcatcc      3120 aaaccatat ctagtcttaa cacatggaga atgctggagt gaggggttgtg agttcagggt      3180 atataatcaa gaaaacactc ccagcataat gctaggggtc accagtgtcc atcccccaga      3240
actgtatgga tctaggatat acacagctgc gttgcattaa gaaagagatg aaatctctat      3300
taaaatacac aagatttttg tatctccttg tgcagaggat atttgccact gcccattggg      3360
```

-continued

```
aagcagacaa gttataggg gctgggggcc aacactggca agtaggaaac cacgggtcgg   3420
acaggtgagc aaaatgtgct ggcaggtggg caccactggg agaccacac tgcacacccg    3480 ggcaccgtat gaacaggaaa gaggaaggaa gctggacgaa gcccctcagg gaccctgtgc   3540
tgaccatgct gggcccaccg gcaaaaggga gatattcagt tccttgtctc atccttaagg   3600
tttcttccac aacatctgaa tacaagcatg tttaactggg aaaatgtcta tgtcatgcgt   3660
gaataacacc agcagcaaac actcacacat cacgcagaca cggccggcag catgctgacg   3720
cttttaggta ttttcactc atgcaatttt cacatatttt cactcatttc atttgcacgg    3780
aaattctatg aggtagatgc tgttatcaaa tccacattac agatgaggga cccagggtcc   3840
aggaaggtga actggcagaa gtctcccagc tggtagaaca gggctgcaag gcatcgattc   3900
ccaggtgtct cacagccctg agaagatggc gttttcccta tcagtggctc tgaggaagtc   3960
aagccttcag tctctacctc tcccaccaat tcttttggaa acagcaaacc aatgttacac   4020
acacttccta atccagagga agctagaaca cgatttttaa atttatttag taaaataaaa   4080
ctttttttgc agatgtaacg aaaaaaaaa                                    4109
```

<210> SEQ ID NO 8
<211> LENGTH: 640
<212> TYPE: PRT
<213> ORGANISM: Homo sapiens

<400> SEQUENCE: 8

```
Met Asp Met Gly Thr Gln Gly Ser Gly Arg Lys Arg Leu Pro Asn Arg
1               5                   10                  15

Glu Arg Leu Thr Ala Glu Asp Ala Leu Asn Gln Ile Ala Arg Glu
            20                  25                  30

Ala Glu Ala Arg Leu Ala Ala Lys Arg Ala Ala Arg Ala Glu Ala Arg
        35                  40                  45

Glu Ile Arg Met Lys Glu Leu Glu Arg Gln Gln Lys Glu Ile Tyr Gln
    50                  55                  60

Val Gln Lys Lys Tyr Tyr Gly Leu Asp Thr Lys Trp Gly Asp Ile Glu
65                  70                  75                  80

Gln Trp Met Glu Asp Ser Glu Arg Tyr Ser Arg Ser Arg Arg Asn
                85                  90                  95

Thr Ser Ala Ser Asp Glu Asp Glu Arg Met Ser Val Gly Ser Arg Gly
            100                 105                 110

Ser Leu Arg Ser Gln Pro Asp Leu Glu Tyr Gly Gly Pro Tyr Ala Trp
        115                 120                 125

Thr Asn Gly Tyr Asp Gly Glu Leu Tyr Gly Ser Gln Ser Leu Asn Arg
    130                 135                 140

Arg Ser Gly Arg Pro Ser Cys Leu Tyr Ser Ala Ala Arg Pro Ser Gly
145                 150                 155                 160

Ser Tyr Arg Ala Ser Val Leu Asp Glu Gly Ser Phe Gly Gly Thr Arg
                165                 170                 175

Arg Gly Ser Thr Ser Gly Ser Arg Ala Pro Ser Glu Tyr Ser Gly His
            180                 185                 190

Leu Asn Ser Ser Ser Arg Ala Ser Arg Ala Ser Ser Ala Arg Ala
        195                 200                 205

Ser Pro Val Val Glu Glu Arg Pro Glu Lys Asp Phe Thr Glu Lys Gly
    210                 215                 220

Ser Arg Asn Met Pro Gly Leu Ser Ala Ala Thr Leu Ala Ser Leu Gly
225                 230                 235                 240
```

```
Gly Thr Ser Ser Arg Arg Gly Ser Gly Asp Thr Ser Ile Ser Ile Asp
                245                 250                 255

Thr Glu Ala Ser Ile Arg Glu Ile Lys Glu Leu Asn Glu Leu Lys Asp
            260                 265                 270

Gln Ile Gln Asp Val Glu Gly Lys Tyr Met Gln Gly Leu Lys Glu Met
        275                 280                 285

Lys Asp Ser Leu Ala Glu Val Glu Glu Lys Tyr Lys Lys Ala Met Val
    290                 295                 300

Ser Asn Ala Gln Leu Asp Asn Glu Lys Thr Asn Phe Met Tyr Gln Val
305                 310                 315                 320

Asp Thr Leu Lys Asp Met Leu Glu Leu Glu Glu Gln Leu Ala Glu
                325                 330                 335

Ser Arg Arg Gln Tyr Glu Glu Lys Asn Lys Glu Phe Glu Arg Glu Lys
            340                 345                 350

His Ala His Ser Ile Leu Gln Phe Gln Phe Ala Glu Val Lys Glu Ala
        355                 360                 365

Leu Lys Gln Arg Glu Glu Met Leu Glu Glu Ile Arg Gln Leu Gln Gln
    370                 375                 380

Lys Gln Ala Ser Ser Ile Arg Glu Ile Ser Asp Leu Gln Glu Thr Ile
385                 390                 395                 400

Glu Trp Lys Asp Lys Lys Ile Gly Ala Leu Glu Arg Gln Lys Glu Phe
                405                 410                 415

Phe Asp Ser Val Arg Ser Glu Arg Asp Asp Leu Arg Glu Glu Val Val
            420                 425                 430

Met Leu Lys Glu Leu Lys Lys His Gly Ile Ile Leu Asn Ser Glu
        435                 440                 445

Ile Ala Thr Asn Gly Glu Thr Ser Asp Thr Leu Asn Asn Val Gly Tyr
    450                 455                 460

Gln Gly Pro Thr Lys Met Thr Lys Glu Glu Leu Asn Ala Leu Lys Ser
465                 470                 475                 480

Thr Gly Asp Gly Thr Leu Asp Ile Arg Leu Lys Lys Leu Val Asp Glu
                485                 490                 495

Arg Glu Cys Leu Leu Glu Gln Ile Lys Lys Leu Lys Gly Gln Leu Glu
            500                 505                 510

Glu Arg Gln Lys Ile Gly Lys Leu Asp Asn Leu Arg Ser Glu Asp Asp
        515                 520                 525

Val Leu Glu Asn Gly Thr Asp Met His Val Met Asp Leu Gln Arg Asp
    530                 535                 540

Ala Asn Arg Gln Ile Ser Asp Leu Lys Phe Lys Leu Ala Lys Ser Glu
545                 550                 555                 560

Gln Glu Ile Thr Ala Leu Glu Gln Asn Val Ile Arg Leu Glu Ser Gln
                565                 570                 575

Val Ser Arg Tyr Lys Ser Ala Ala Glu Asn Ala Glu Lys Ile Glu Asp
            580                 585                 590

Glu Leu Lys Ala Glu Lys Arg Lys Leu Gln Arg Glu Leu Arg Ser Ala
        595                 600                 605

Leu Asp Lys Thr Glu Glu Leu Glu Val Ser Asn Gly His Leu Val Lys
    610                 615                 620

Arg Leu Glu Lys Met Lys Ala Asn Arg Ser Ala Leu Leu Ser Gln Gln
625                 630                 635                 640

<210> SEQ ID NO 9
<211> LENGTH: 3599
```

<212> TYPE: DNA
<213> ORGANISM: Homo sapiens

<400> SEQUENCE: 9

| | | | | | |
|---|---|---|---|---|---|
| ccgtgggacg | ggcggaggcg | cccgagtccc | gcttccccgg | cgcccttcca | ccccgagccc | 60 |
| gactcagccc | gcggccacct | gcgccccgcc | cctgtcggcc | gcgcccgagc | ccagcgccgc | 120 |
| gagccgctcc | ccggcgggct | ggctcctggc | cccggaagcg | cgagcgttca | cttagcggcg | 180 |
| agtggctccg | tctccgcgga | cagagcgcgc | gcccccctggc | ccggcccgcg | aggggctccc | 240 |
| ggcgcggtcc | ccgagcattt | cccgccgggt | ggagcgggcc | gagcccggca | ggatgaccag | 300 |
| ccccgcggcc | gctcaaagcc | gggagatcga | ctgtttgagc | ccggaagcgc | agaagctggc | 360 |
| ggaagcccgg | ctcgctgcaa | acgggcggc | ccgcgcggag | gctcgcgaga | tccgcatgaa | 420 |
| ggagctggag | cggcagcaga | aggaggtaga | agagagacca | gaaaaagatt | ttactgagaa | 480 |
| ggggtctcgt | aacatgccgg | gcctgtctgc | agccacgctg | gcctctctgg | gtgggacttc | 540 |
| ctctcggaga | ggcagcggag | acacctccat | ctccatcgac | accgaggcat | ccatcaggga | 600 |
| aatcaaggac | tctctagcag | aagttgaaga | gaaatataag | aaggctatgg | tttccaatgc | 660 |
| tcagctagac | aatgaaaaga | caaacttcat | gtaccaggtt | gataccctaa | aagatatgtt | 720 |
| gctggagctt | gaagaacagc | tggctgaatc | taggcggcag | tacgaagaga | aaacaaaga | 780 |
| atttgaaagg | gaaaaacacg | cccacagtat | actgcaattt | cagtttgctg | aagtcaagga | 840 |
| ggccctgaag | caaagagagg | aaatgctcga | gaaacatgga | ataatcctaa | attcagaaat | 900 |
| agctaccaat | ggagagactt | ccgacaccct | caataatgtt | ggataccaag | gtcctaccaa | 960 |
| gatgacaaaa | gaagagttaa | atgccctcaa | gtcgacaggg | gatgggaccc | tagatattag | 1020 |
| gttgaaaaag | ctggttgatg | aacgggaatg | cttattggaa | cagattaaga | aactcaaagg | 1080 |
| gcagctggag | gagagacaga | agattggcaa | actagacaat | cttcgatctg | aagatgatgt | 1140 |
| cttggaaaac | gggacagaca | tgcatgtaat | ggacctacaa | agggatgcca | acagacagat | 1200 |
| cagcgacctc | aaatttaaac | ttgcaaaatc | tgagcaagag | ataactgcat | tagaacaaaa | 1260 |
| tgtaataagg | ttagagagtc | aagtatcacg | ttacaaatca | gcggctgaaa | atgcagaaaa | 1320 |
| aatagaagat | gaacttaagg | cagaaaaacg | gaaactccaa | agagagctcc | gctctgcatt | 1380 |
| ggataaaaca | gaagagctcg | aggtgagcaa | cggccactta | gtgaagcgtc | tggaaaaaat | 1440 |
| gaaagcaaat | cggagtgcac | tcttgtccca | gcagtaaatt | ccagtctga | tcaggcaact | 1500 |
| ggttggtgac | tggagagcat | tgtttcatag | gcttttctct | gtcctatctg | ggagcgctgc | 1560 |
| ttcttcccct | gccttccgag | agacgaagac | cgtggcgagc | ttggcgctta | ggggctcccg | 1620 |
| tgccatggct | caccccaggg | agccccagca | gccaccaggt | gcctctgtct | gcagacccct | 1680 |
| ggcccgggct | ggcgccgacg | ctcagaacct | gcaggtactt | cataagcaca | caggggcctc | 1740 |
| gagggagctc | tgtgtctgac | cgcacagcag | cctctgaatg | ccgctggaag | tgatgatcaa | 1800 |
| agtaaagatt | cagttgggac | ttgagttttt | tttttttttc | atgtgtcttg | ctgaagatta | 1860 |
| aggggaaatg | ttacagtgtt | gggacttcct | ttcatggcag | aatctacaat | ttgagcgact | 1920 |
| tcagtagtat | ctcttagtct | acgcttttca | tacacaaaac | actgtggaac | cacaagccat | 1980 |
| taccaagcaa | aactctttca | ctggaaacaa | ggggcagtc | tagaagtaaa | agtgaccttta | 2040 |
| agaagactct | ttacaggcaa | caaatgaagc | ttttctaagg | gatttttgca | tcagttcagt | 2100 |
| cataagaata | cttttttcca | gggtaattag | gcaatagctt | cactgaaaat | gacagctttt | 2160 |
| cattgcatta | tttaatcctt | atatttggaa | ttgaagtcgt | taacttcttt | taaagaatgt | 2220 |

| | |
|---|---|
| actattagaa aaattaaaaa tgaaatgttg agagacttca gcaatgtggt tctaattttt | 2280 |
| ttccactgag aaagaagatc tttaatttca tattaatggt tctgtatatt ttgggtcatc | 2340 |
| tttttatttt ttaagaatat caagtcaatt cattttctt tccctattta aaaaaaaagg | 2400 |
| tgttttcaca gaatgagtgc acttaaaaag tgaagtgaag gaggaggtaa cagtagagac | 2460 |
| gatggcaata tcatcaagga caaaagtaaa aacgtttagc tacctgctga ttttagtga | 2520 |
| ctgttcatat atgttgtatt tcaagtatgg ctggtgaagc cagtcagctt tcgggacgt | 2580 |
| tagcaagtgg aaactgagtc agtatcatcc aaaaccatat ctagtcttaa cacatggaga | 2640 |
| atgctggagt gagggttgtg agttcagggt atataatcaa gaaacactc ccagcataat | 2700 |
| gctaggggtc accagtgtcc atccccaga actgtatgga tctaggatat acacagctgc | 2760 |
| gttgcattaa gaaagagatg aaatctctat taaaatacac aagatttttg tatctccttg | 2820 |
| tgcagaggat atttgccact gcccattggg aagcagacaa gttataggg gctgggggcc | 2880 |
| aacactggca gtaggaaac cacgggtcgg acaggtgagc aaaatgtgct ggcaggtggg | 2940 |
| caccactggg agacccacac tgcacacccg ggcaccgtat gaacaggaaa gaggaaggaa | 3000 |
| gctggacgaa gcccctcagg gaccctgtgc tgaccatgct gggcccaccg gcaaaggga | 3060 |
| gatattcagt tccttgtctc atccttaagg tttcttccac aacatctgaa tacaagcatg | 3120 |
| tttaactggg aaaatgtcta tgtcatgcgt gaataacacc agcagcaaac actcacacat | 3180 |
| cacgcagaca cggccggcag catgctgacg cttttaggta tttttcactc atgcaatttt | 3240 |
| cacatatttt cactcatttc atttgcacgg aaattctatg aggtagatgc tgttatcaaa | 3300 |
| tccacattac agatgaggga cccagggtcc aggaaggtga actggcagaa gtctcccagc | 3360 |
| tggtagaaca gggctgcaag gcatcgattc ccaggtgtct cacagccctg agaagatggc | 3420 |
| gttttcccta tcagtggctc tgaggaagtc aagccttcag tctctacctc tcccaccaat | 3480 |
| tcttttggaa acagcaaacc aatgttacac acacttccta atccagagga agctagaaca | 3540 |
| cgatttttaa attttatttag taaaataaaa cttttttttgc agatgtaacg aaaaaaaaa | 3599 |

<210> SEQ ID NO 10
<211> LENGTH: 394
<212> TYPE: PRT
<213> ORGANISM: Homo sapiens

<400> SEQUENCE: 10

Met Thr Ser Pro Ala Ala Ala Gln Ser Arg Glu Ile Asp Cys Leu Ser
1               5                   10                  15

Pro Glu Ala Gln Lys Leu Ala Glu Ala Arg Leu Ala Ala Lys Arg Ala
            20                  25                  30

Ala Arg Ala Glu Ala Arg Glu Ile Arg Met Lys Glu Leu Glu Arg Gln
        35                  40                  45

Gln Lys Glu Val Glu Glu Arg Pro Glu Lys Asp Phe Thr Glu Lys Gly
    50                  55                  60

Ser Arg Asn Met Pro Gly Leu Ser Ala Ala Thr Leu Ala Ser Leu Gly
65                  70                  75                  80

Gly Thr Ser Ser Arg Arg Gly Ser Gly Asp Thr Ser Ile Ser Ile Asp
                85                  90                  95

Thr Glu Ala Ser Ile Arg Glu Ile Lys Asp Ser Leu Ala Glu Val Glu
            100                 105                 110

Glu Lys Tyr Lys Lys Ala Met Val Ser Asn Ala Gln Leu Asp Asn Glu
        115                 120                 125

Lys Thr Asn Phe Met Tyr Gln Val Asp Thr Leu Lys Asp Met Leu Leu

```
                    130                 135                 140
Glu Leu Glu Glu Gln Leu Ala Glu Ser Arg Arg Gln Tyr Glu Glu Lys
145                 150                 155                 160

Asn Lys Glu Phe Glu Arg Glu Lys His Ala His Ser Ile Leu Gln Phe
                165                 170                 175

Gln Phe Ala Glu Val Lys Glu Ala Leu Lys Gln Arg Glu Glu Met Leu
            180                 185                 190

Glu Lys His Gly Ile Ile Leu Asn Ser Glu Ile Ala Thr Asn Gly Glu
        195                 200                 205

Thr Ser Asp Thr Leu Asn Asn Val Gly Tyr Gln Gly Pro Thr Lys Met
210                 215                 220

Thr Lys Glu Glu Leu Asn Ala Leu Lys Ser Thr Gly Asp Gly Thr Leu
225                 230                 235                 240

Asp Ile Arg Leu Lys Lys Leu Val Asp Glu Arg Glu Cys Leu Leu Glu
                245                 250                 255

Gln Ile Lys Lys Leu Lys Gly Gln Leu Glu Glu Arg Gln Lys Ile Gly
            260                 265                 270

Lys Leu Asp Asn Leu Arg Ser Glu Asp Val Leu Glu Asn Gly Thr
        275                 280                 285

Asp Met His Val Met Asp Leu Gln Arg Asp Ala Asn Arg Gln Ile Ser
290                 295                 300

Asp Leu Lys Phe Lys Leu Ala Lys Ser Glu Gln Glu Ile Thr Ala Leu
305                 310                 315                 320

Glu Gln Asn Val Ile Arg Leu Glu Ser Gln Val Ser Arg Tyr Lys Ser
                325                 330                 335

Ala Ala Glu Asn Ala Glu Lys Ile Glu Asp Glu Leu Lys Ala Glu Lys
            340                 345                 350

Arg Lys Leu Gln Arg Glu Leu Arg Ser Ala Leu Asp Lys Thr Glu Glu
        355                 360                 365

Leu Glu Val Ser Asn Gly His Leu Val Lys Arg Leu Glu Lys Met Lys
    370                 375                 380

Ala Asn Arg Ser Ala Leu Leu Ser Gln Gln
385                 390

<210> SEQ ID NO 11
<211> LENGTH: 4510
<212> TYPE: DNA
<213> ORGANISM: Homo sapiens

<400> SEQUENCE: 11
ccgtgggacg ggcggaggcg cccgagtccc gcttccccgg cgcccttcca ccccgagccc    60
gactcagccc gcggccacct gcgccccgcc cctgtcggcc gcgcccgagc cagcgccgc   120 gagccgctcc ccggcgggct ggctcctggc cccggaagcg cgagcgttca cttagcggcg   180
agtggctccg tctccgcgga cagagcgcgc gcccccctggc ccggcccgcg aggggctccc   240
ggcgcggtcc ccgagcattt cccgccgggt ggagcgggcc gagcccggca ggatgaccag   300
ccccgcggcc gctcaaagcc gggagatcga ctgtttgagc ccggaagcgc agaagctggc   360
ggaagcccgg ctcgctgcaa acgggcggcg ccgcgcggag gctcgcgaga tccgcatgaa   420
ggagctggag cggcagcaga aggaggaaga cagtgagcgc tactctcgta gatccagaag   480
aaacacatcg gcttctgatg aagacgagcg catgtcagtg ggtagtcgtg aagcctgag   540 ggtagaagag agaccagaaa aagatttttac tgagaagggg tctcgtaaca tgccgggcct   600
gtctgcagcc acgctggcct ctctgggtgg gacttcctct cggagaggca gcggagacac   660
```

```
ctccatctcc atcgacaccg aggcatccat cagggaaatc aaggaactca atgagttaaa      720
ggaccagatt caggatgtag aaggcaaata catgcaggga ttgaaagaga tgaaggactc      780
tctagcagaa gttgaagaga aatataagaa ggctatggtt tccaatgctc agctagacaa      840
tgaaaagaca aacttcatgt accaggttga taccctaaaa gatatgttgc tggagcttga      900
agaacagctg gctgaatcta ggcggcagta cgaagagaaa aacaaagaat tgaaagggaa     960
aaaacacgcc cacagtatac tgcaatttca gtttgctgaa gtcaaggagg ccctgaagca     1020
aagagaggaa atgctcgaga acatggaat aatcctaaat tcagaaatag ctaccaatgg      1080
agagacttcc gacaccctca ataatgttgg ataccaaggt cctaccaaga tgacaaaaga     1140
agagttaaat gccctcaagt cgacagggga tgggacccta ggaagagcca gtgaagtgga     1200
ggtgaaaaat gaaatcgtgg cgaatgtggg gaaaagagaa atcttgcaca atactgagaa     1260
agaacaacac acagaggaca cagtgaagga ctgtgtggac atagaggtat cccctgctgg     1320
tgagaatacc gaggaccaga atcctctga gacactgcc ccattcctag gaaccttagc      1380
aggtgctacc tatgaggaac aggttcaaag ccaaattctt gagagcagtt ctctccctga     1440
aaacacagta caggttgagt caaatgaggt catgggtgca ccagatgaca ggaccagaac     1500
tccccttgag ccatccaact gttggagtga cttagatggt gggaaccaca cagagaatgt     1560
gggagaggca gcagtgactc aggttgaaga gcaggcaggc acagtggcct cgtgtccttt     1620
agggcatagt gatgacacag tttatcatga tgacaaatgt atggtagagg tcccccaaga     1680
gttagagaca agcacagggc atagtttaga gaaagaattc accaaccagg aagcagctga     1740
gcccaaggag gttccagcgc acagtacaga agtaggtagg gatcacaacg aagaagaggg     1800
tgaagaaaca ggattaaggg acgagaaacc aatcaagaca gaagttcctg gttctccagc     1860
aggaactgag ggcaactgtc aggaagcgac aggtccaagt acagtagaca ctcaaaatga     1920
acccttagat atgaaagagc ccgatgaaga aagagtgac caacagggag aggcattgga      1980
ctcatcgcag aagaagacaa agaacaagaa aaagaaaaac aagaagaaaa aatccccagt     2040
acccgtagaa acccttaaag atgttaaaaa agagttaacg tatcagaaca cagatttaag     2100
tgaaattaag gaagaagagc aggtaaagtc tactgacaga aagtcagcag tggaagccca     2160
aaacgaggtg actgaaaatc caaaacgaa aattgcagca gaaagcagtg aaaatgttga     2220
ttgtccggag aatcctaaaa ttaagttgga tggaaaactt gaccaagaag gtgatgatgt     2280
acaaacagca gctgaggagg tactagctga tggagacaca ttagattttg aggatgacac     2340
cgttcaatca tcaggcccga gggctggtgg tgaagaatta gatgaaggtg ttgcaaaaga     2400
taatgctaaa atagatggtg ccactcaaag cagtcctgca gaaccaaaga gcgaagacgc     2460
agatcgctgc accctgcccg aacatgaaag tccctcacag gacattagtg atgcctgtga     2520
agcagaaagt acagagaggt gtgagatgtc agaacatcca agtcagaccg tcaggaaagc     2580
tttagacagc aatagcctag agaacgatga cttgtcggca ccaggaagag agccagggca     2640
cttcaatcca gaaagcagag aagataccag aggagggaat gagaagggca aaagcaaaga     2700
agactgtacc atgtcctaag ctgaggcagg cggcaggcgc ggtgcacagg aagtctcagt     2760 gtgaagggt cttttctctc cactgccaat gtaagtagaa tgttctaaat tcatagagag     2820
gcactgtatg acaattacca ggtgctctac tgctttaagt tatagactgt tacttgtaga     2880
tttccatgta atcattgagg ttatcaccca gattagaaag acatatttgt tatcagtgta     2940
cgttctaatt gagagcattc cagtagtatc aaacaataat gtctactgtt tatagtccac     3000
```

-continued

```
ttaataaaaa tagaggcatt tactatttgc cttaggctga taggaatgtg ggttttcttg    3060
accaaatata tcagcatcta attgaaatga ccaaatagca ttcttagact tctgtattat    3120
gaatataatt gatatttaaa ttaatgtctt gttcacatat gtgtactttc atatttgatt    3180
ttaaaatgta cattataacc tgtatggtat tttatttaaa ggagataaac agccaaatag    3240
caaataggtc actgaatgat aagatttgca ccttagaaca ataatcattt taaggataac    3300
aagtaaatgt ctgaaagcat gaggggcttt atttgccttt acctcatatg agtctttgat    3360
cttgaaccga tacttttgga tctcattgtt gatatacctg aatttacttt gtaagagatt    3420
ttaacttcac ttcatgctga tgatgtatca aattcatttt atagaaagat ttaaagttt     3480 tttctggaag tgatatatgt caaattacat ttcctactgc agtatttgag cagggacagt    3540
cattttttaa atgttttttgg ccgggcgtgg tggctcatgc ctgtaatctc agtacattgg   3600
gaggccaagg caggtggatc acctgaggtc aagagttcga ggccagcctg ccaacatgg     3660 tgaaaccctg tctctactaa aaatacaaaa aattggccgg gcgtgatggt gggcgcctgt    3720
aatcccagcc actccagagg ctgaggcagg agaatcgctt gaacctgcga ggcagagatt    3780
gcagtgagcc aagatcaagc cattgtactc cagcctggac aacaagagcg aaactctgtc    3840
taaaaaaaaa aaaaaaaaca cacacacaca caacacaatg ttttcacgcc tgtaaaccta    3900
gcacattggg aagccaaggt gggaggattg cttgaggcca ggagttcaag gctgcagtga    3960
gctatgattg cacactgtac tctagcctgg gagacagagt gagacactgt ctctaaaaaa    4020
aaaaaaaaaa aaaaaaaaag tttttgaacc ttaaaatact ttgtttgaat ttctaatcat    4080
cattcaaaag agcagtaaaa aatggttact tgttcttgta caagctacta attagactat    4140
agtaggatat tttaaagagc tgaatcactt ttggtatttt ggtataaata ttttcatttg    4200
ttatgtccca gtatattctt actggaaaat tcttgttttg atctgcctga agaaaatatc    4260
tgttttctat ataaaaaaat ttttttaaaat aattgtaaag ttagatttaa aattgtaaaa    4320
tataaaatca caaaggaatg taccttatga atgttgttga cattttatga aattatgtgg    4380
attcatatta ctgttacaag atagaattga atgcaaaaag accaaaacct caataaaatt    4440
tgaggaaaac gtgttattat gtaattgaaa taaaaacatt ttataattgt gcaaaaaaaa    4500
aaaaaaaaa                                                            4510
```

<210> SEQ ID NO 12
<211> LENGTH: 808
<212> TYPE: PRT
<213> ORGANISM: Homo sapiens

<400> SEQUENCE: 12

```
Met Thr Ser Pro Ala Ala Gln Ser Arg Glu Ile Asp Cys Leu Ser
1               5                   10                  15

Pro Glu Ala Gln Lys Leu Ala Glu Ala Arg Leu Ala Ala Lys Arg Ala
                20                  25                  30

Ala Arg Ala Glu Ala Arg Glu Ile Arg Met Lys Glu Leu Glu Arg Gln
        35                  40                  45

Gln Lys Glu Glu Asp Ser Glu Arg Tyr Ser Arg Ser Arg Arg Asn
    50                  55                  60

Thr Ser Ala Ser Asp Glu Asp Glu Arg Met Ser Val Gly Ser Arg Gly
65                  70                  75                  80

Ser Leu Arg Val Glu Glu Arg Pro Glu Lys Asp Phe Thr Glu Lys Gly
                85                  90                  95

Ser Arg Asn Met Pro Gly Leu Ser Ala Ala Thr Leu Ala Ser Leu Gly
```

```
            100                 105                 110
Gly Thr Ser Ser Arg Arg Gly Ser Gly Asp Thr Ser Ile Ser Ile Asp
            115                 120                 125

Thr Glu Ala Ser Ile Arg Glu Ile Lys Glu Leu Asn Glu Leu Lys Asp
            130                 135             140

Gln Ile Gln Asp Val Glu Gly Lys Tyr Met Gln Gly Leu Lys Glu Met
145                 150                 155                 160

Lys Asp Ser Leu Ala Glu Val Glu Lys Tyr Lys Lys Ala Met Val
                165                 170                 175

Ser Asn Ala Gln Leu Asp Asn Glu Lys Thr Asn Phe Met Tyr Gln Val
                180                 185                 190

Asp Thr Leu Lys Asp Met Leu Leu Glu Leu Glu Gln Leu Ala Glu
            195                 200             205

Ser Arg Arg Gln Tyr Glu Glu Lys Asn Lys Glu Phe Glu Arg Glu Lys
            210                 215                 220

His Ala His Ser Ile Leu Gln Phe Gln Phe Ala Glu Val Lys Glu Ala
225                 230                 235                 240

Leu Lys Gln Arg Glu Glu Met Leu Glu Lys His Gly Ile Ile Leu Asn
                245                 250                 255

Ser Glu Ile Ala Thr Asn Gly Glu Thr Ser Asp Thr Leu Asn Asn Val
                260                 265                 270

Gly Tyr Gln Gly Pro Thr Lys Met Thr Lys Glu Glu Leu Asn Ala Leu
            275                 280                 285

Lys Ser Thr Gly Asp Gly Thr Leu Gly Arg Ala Ser Glu Val Glu Val
            290                 295             300

Lys Asn Glu Ile Val Ala Asn Val Gly Lys Arg Glu Ile Leu His Asn
305                 310                 315                 320

Thr Glu Lys Glu Gln His Thr Glu Asp Thr Val Lys Asp Cys Val Asp
                325                 330                 335

Ile Glu Val Phe Pro Ala Gly Glu Asn Thr Glu Asp Gln Lys Ser Ser
                340                 345             350

Glu Asp Thr Ala Pro Phe Leu Gly Thr Leu Ala Gly Ala Thr Tyr Glu
            355                 360                 365

Glu Gln Val Gln Ser Gln Ile Leu Glu Ser Ser Leu Pro Glu Asn
            370                 375             380

Thr Val Gln Val Glu Ser Asn Glu Val Met Gly Ala Pro Asp Asp Arg
385                 390                 395                 400

Thr Arg Thr Pro Leu Glu Pro Ser Asn Cys Trp Ser Asp Leu Asp Gly
                405                 410                 415

Gly Asn His Thr Glu Asn Val Gly Glu Ala Ala Val Thr Gln Val Glu
            420                 425                 430

Glu Gln Ala Gly Thr Val Ala Ser Cys Pro Leu Gly His Ser Asp Asp
            435                 440                 445

Thr Val Tyr His Asp Asp Lys Cys Met Val Glu Val Pro Gln Glu Leu
            450                 455             460

Glu Thr Ser Thr Gly His Ser Leu Glu Lys Glu Phe Thr Asn Gln Glu
465                 470                 475                 480

Ala Ala Glu Pro Lys Glu Val Pro Ala His Ser Thr Glu Val Gly Arg
                485                 490                 495

Asp His Asn Glu Glu Glu Gly Glu Thr Gly Leu Arg Asp Glu Lys
                500                 505                 510

Pro Ile Lys Thr Glu Val Pro Gly Ser Pro Ala Gly Thr Glu Gly Asn
            515                 520                 525
```

```
Cys Gln Glu Ala Thr Gly Pro Ser Thr Val Asp Thr Gln Asn Glu Pro
            530                 535                 540

Leu Asp Met Lys Glu Pro Asp Glu Glu Lys Ser Asp Gln Gln Gly Glu
545                 550                 555                 560

Ala Leu Asp Ser Ser Gln Lys Lys Thr Lys Asn Lys Lys Lys Lys Asn
                565                 570                 575

Lys Lys Lys Lys Ser Pro Val Pro Val Glu Thr Leu Lys Asp Val Lys
            580                 585                 590

Lys Glu Leu Thr Tyr Gln Asn Thr Asp Leu Ser Glu Ile Lys Glu Glu
        595                 600                 605

Glu Gln Val Lys Ser Thr Asp Arg Lys Ser Ala Val Glu Ala Gln Asn
    610                 615                 620

Glu Val Thr Glu Asn Pro Lys Gln Lys Ile Ala Ala Glu Ser Ser Glu
625                 630                 635                 640

Asn Val Asp Cys Pro Glu Asn Pro Lys Ile Lys Leu Asp Gly Lys Leu
                645                 650                 655

Asp Gln Glu Gly Asp Asp Val Gln Thr Ala Ala Glu Val Leu Ala
            660                 665                 670

Asp Gly Asp Thr Leu Asp Phe Glu Asp Thr Val Gln Ser Ser Gly
        675                 680                 685

Pro Arg Ala Gly Gly Glu Glu Leu Asp Glu Gly Val Ala Lys Asp Asn
    690                 695                 700

Ala Lys Ile Asp Gly Ala Thr Gln Ser Ser Pro Ala Glu Pro Lys Ser
705                 710                 715                 720

Glu Asp Ala Asp Arg Cys Thr Leu Pro Glu His Glu Ser Pro Ser Gln
                725                 730                 735

Asp Ile Ser Asp Ala Cys Glu Ala Glu Ser Thr Glu Arg Cys Glu Met
            740                 745                 750

Ser Glu His Pro Ser Gln Thr Val Arg Lys Ala Leu Asp Ser Asn Ser
        755                 760                 765

Leu Glu Asn Asp Asp Leu Ser Ala Pro Gly Arg Glu Pro Gly His Phe
    770                 775                 780

Asn Pro Glu Ser Arg Glu Asp Thr Arg Gly Gly Asn Glu Lys Gly Lys
785                 790                 795                 800

Ser Lys Glu Asp Cys Thr Met Ser
                805

<210> SEQ ID NO 13
<211> LENGTH: 4438
<212> TYPE: DNA
<213> ORGANISM: Homo sapiens

<400> SEQUENCE: 13
ccgtgggacg gcggaggcg cccgagtccc gcttccccgg cgccttcca ccccgagccc      60 gactcagccc gcggccacct gcgccccgcc cctgtcggcc gcgcccgagc cagcgccgc    120 gagccgctcc ccggcgggct ggctcctggc cccggaagcg cgagcgttca cttagcggcg   180
agtggctccg tctccgcgga cagagcgcgc gcccctggc ccggcccgcg agggctccc    240 ggcgcggtcc ccgagcattt ccgccgggt ggagcgggcc gagcccggca ggatgaccag    300
ccccgcggcc gctcaaagcc gggagatcga ctgtttgagc ccggaagcgc agaagctggc   360
ggaagcccgg ctcgctgcaa acgggcggc ccgcgcggag gctcgcgaga tccgcatgaa    420
ggagctggag cggcagcaga aggaggaaga cagtgagcgc tactctcgta gatccagaag    480
```

-continued

```
aaacacatcg gcttctgatg aagacgagcg catgtcagtg ggtagtcgtg gaagcctgag    540
ggtagaagag agaccagaaa aagatttac  tgagaagggg tctcgtaaca tgccgggcct    600
gtctgcagcc acgctggcct ctctgggtgg gacttcctct cggagaggca gcggagacac    660
ctccatctcc atcgacaccg aggcatccat cagggaaatc aaggactctc tagcagaagt    720
tgaagagaaa tataagaagg ctatggtttc caatgctcag ctagacaatg aaaagacaaa    780
cttcatgtac caggttgata ccctaaaaga tatgttgctg gagcttgaag aacagctggc    840
tgaatctagg cggcagtacg aagagaaaaa caaagaattt gaagggaaa  acacgccca    900 cagtatactg caatttcagt ttgctgaagt caaggaggcc ctgaagcaaa gagaggaaat    960
gctcgagaaa catggaataa tcctaaattc agaaatagct accaatggag agacttccga   1020
caccctcaat aatgttggat accaaggtcc taccaagatg acaaaagaag agttaaatgc   1080
cctcaagtcg acagggatg  ggaccctagg aagagccagt gaagtggagg tgaaaaatga   1140
aatcgtggcg aatgtgggga aaagagaaat cttgcacaat actgagaaag aacaacacac   1200
agaggacaca gtgaaggact gtgtggacat agaggtattc cctgctggtg agaataccga   1260
ggaccagaaa tcctctgaag acactgcccc attcctagga accttagcag gtgctaccta   1320
tgaggaacag gttcaaagcc aaattcttga gagcagttct ctccctgaaa acacagtaca   1380
ggttgagtca aatgaggtca tgggtgcacc agatgacagg accagaactc cccttgagcc   1440
atccaactgt tggagtgact tagatggtgg gaaccacaca gagaatgtgg gagaggcagc   1500
agtgactcag gttgaagagc aggcaggcac agtggcctcg tgtcctttag ggcatagtga   1560
tgacacagtt tatcatgatg acaaatgtat ggtagaggtc ccccaagagt tagagacaag   1620
cacagggcat agtttagaga agaattcac  caaccaggaa gcagctgagc ccaaggaggt   1680
tccagcgcac agtacagaag taggtaggga tcacaacgaa aagagggtg  aagaaacagg   1740 attaagggac gagaaaccaa tcaagacaga agttcctggt tctccagcag gaactgaggg   1800
caactgtcag gaagcgacag gtccaagtac agtagacact caaaatgaac ccttagatat   1860
gaaagagccc gatgaagaaa agagtgacca acagggagag gcattggact catcgcagaa   1920
gaagacaaag aacaagaaaa agaaaaacaa gaagaaaaaa tccccagtac ccgtagaaac   1980
ccttaaagat gttaaaaaag agttaacgta tcagaacaca gatttaagtg aaattaagga   2040
agaagagcag gtaaagtcta ctgacagaaa gtcagcagtg gaagcccaaa acgaggtgac   2100
tgaaaatcca aaacagaaaa ttgcagcaga aagcagtgaa aatgttgatt gtccggagaa   2160
tcctaaaatt aagttggatg gaaaacttga ccaagaaggt gatgatgtac aaacagcagc   2220
tgaggaggta ctagctgatg gagacacatt agattttgag gatgacaccg ttcaatcatc   2280
aggcccgagg gctggtggtg aagaattaga tgaaggtgtt gcaaaagata tgctaaaat    2340 agatggtgcc actcaaagca gtcctgcaga accaaagagc aagacgcag  atcgctgcac   2400 cctgcccgaa catgaaagtc cctcacagga cattagtgat gcctgtgaag cagaaagtac   2460
agagaggtgt gagatgtcag aacatccaag tcagaccgtc aggaaagctt tagacagcaa   2520
tagcctagag aacgatgact tgtcggcacc aggaagagag ccagggcact tcaatccaga   2580
aagcagagaa gataccagag gagggaatga gaagggcaaa agcaaagaag actgtaccat   2640
gtcctaagct gaggcaggcg gcaggcgcgg tgcacaggaa gtctcagtgt gaagggtct    2700 tttctctcca ctgccaatgt aagtagaatg ttctaaattc atagagaggc actgtatgac   2760
aattaccagg tgctctactg ctttaagtta tagactgtta cttgtagatt tccatgtaat   2820
cattgaggtt atcacccaga ttagaaagac atatttgtta tcagtgtacg ttctaattga   2880
```

```
gagcattcca gtagtatcaa acaataatgt ctactgttta tagtccactt aataaaaata   2940
gaggcattta ctatttgcct taggctgata ggaatgtggg ttttcttgac caaatatatc   3000
agcatctaat tgaaatgacc aaatagcatt cttagacttc tgtattatga atataattga   3060
tatttaaatt aatgtcttgt tcacatatgt gtactttcat atttgatttt aaaatgtaca   3120
ttataacctg tatggtattt tatttaaagg agataaacag ccaaatagca ataggtcac    3180
tgaatgataa gatttgcacc ttagaacaat aatcattta aggataacaa gtaaatgtct    3240
gaaagcatga ggggctttat ttgcctttac ctcatatgag tctttgatct tgaaccgata   3300
cttttggatc tcattgttga tatacctgaa tttactttgt aagagatttt aacttcactt   3360
catgctgatg atgtatcaaa ttcatttat agaaagattt aaagtttttt tctggaagtg    3420
atatatgtca aattcatttt cctactgcag tatttgagca gggacagtca ttttttaaat   3480
gttttggcc gggcgtggtg gctcatgcct gtaatctcag tacattggga ggccaaggca    3540
ggtggatcac ctgaggtcaa gagttcgagg ccagcctggc caacatggtg aaaccctgtc   3600
tctactaaaa atacaaaaaa ttggccgggc gtgatggtgg gcgcctgtaa tcccagccac   3660
tccagaggct gaggcaggag aatcgcttga acctgcgagg cagagattgc agtgagccaa   3720
gatcaagcca ttgtactcca gcctggacaa caagagcgaa actctgtcta aaaaaaaaa    3780
aaaaaacaca cacacacaca acacaatgtt ttcacgcctg taaacctagc acattgggaa   3840
gccaaggtgg gaggattgct tgaggccagg agttcaaggc tgcagtgagc tatgattgca   3900
cactgtactc tagcctggga gacagagtga gacactgtct ctaaaaaaaa aaaaaaaaa   3960
aaaaaaagtt tttgaacctt aaaatacttt gtttgaattt ctaatcatca ttcaaaagag   4020
cagtaaaaaa tggttacttg ttcttgtaca agctactaat tagactatag taggatattt   4080
taaagagctg aatcacttt ggtattttgg tataaatatt ttcatttgtt atgtcccagt    4140
atattcttac tggaaaattc ttgttttgat ctgcctgaag aaaatatctg ttttctatat   4200
aaaaaatt tttaaaataa ttgtaaagtt agatttaaaa ttgtaaaata taaaatcaca    4260
aaggaatgta ccttatgaat gttgttgaca ttttatgaaa ttatgtggat tcatattact   4320
gttacaagat agaattgaat gcaaaaagac caaaacctca ataaatttg aggaaaacgt    4380
gttattatgt aattgaaata aaaacatttt ataattgtgc aaaaaaaaaa aaaaaaa      4438
```

<210> SEQ ID NO 14
<211> LENGTH: 784
<212> TYPE: PRT
<213> ORGANISM: Homo sapiens

<400> SEQUENCE: 14

```
Met Thr Ser Pro Ala Ala Ala Gln Ser Arg Glu Ile Asp Cys Leu Ser
1               5                   10                  15

Pro Glu Ala Gln Lys Leu Ala Glu Ala Arg Leu Ala Ala Lys Arg Ala
                20                  25                  30

Ala Arg Ala Glu Ala Arg Glu Ile Arg Met Lys Glu Leu Glu Arg Gln
            35                  40                  45

Gln Lys Glu Glu Asp Ser Glu Arg Tyr Ser Arg Ser Arg Arg Asn
        50                  55                  60

Thr Ser Ala Ser Asp Glu Asp Glu Arg Met Ser Val Gly Ser Arg Gly
65                  70                  75                  80

Ser Leu Arg Val Glu Glu Arg Pro Glu Lys Asp Phe Thr Glu Lys Gly
                85                  90                  95
```

```
Ser Arg Asn Met Pro Gly Leu Ser Ala Ala Thr Leu Ala Ser Leu Gly
                100                 105                 110

Gly Thr Ser Ser Arg Arg Gly Ser Gly Asp Thr Ser Ile Ser Ile Asp
            115                 120                 125

Thr Glu Ala Ser Ile Arg Glu Ile Lys Asp Ser Leu Ala Glu Val Glu
        130                 135                 140

Glu Lys Tyr Lys Lys Ala Met Val Ser Asn Ala Gln Leu Asp Asn Glu
145                 150                 155                 160

Lys Thr Asn Phe Met Tyr Gln Val Asp Thr Leu Lys Asp Met Leu Leu
                165                 170                 175

Glu Leu Glu Glu Gln Leu Ala Glu Ser Arg Arg Gln Tyr Glu Glu Lys
            180                 185                 190

Asn Lys Glu Phe Glu Arg Glu Lys His Ala His Ser Ile Leu Gln Phe
        195                 200                 205

Gln Phe Ala Glu Val Lys Glu Ala Leu Lys Gln Arg Glu Glu Met Leu
210                 215                 220

Glu Lys His Gly Ile Ile Leu Asn Ser Glu Ile Ala Thr Asn Gly Glu
225                 230                 235                 240

Thr Ser Asp Thr Leu Asn Asn Val Gly Tyr Gln Gly Pro Thr Lys Met
                245                 250                 255

Thr Lys Glu Glu Leu Asn Ala Leu Lys Ser Thr Gly Asp Gly Thr Leu
            260                 265                 270

Gly Arg Ala Ser Glu Val Glu Val Lys Asn Glu Ile Val Ala Asn Val
        275                 280                 285

Gly Lys Arg Glu Ile Leu His Asn Thr Glu Lys Glu Gln His Thr Glu
        290                 295                 300

Asp Thr Val Lys Asp Cys Val Asp Ile Glu Val Phe Pro Ala Gly Glu
305                 310                 315                 320

Asn Thr Glu Asp Gln Lys Ser Ser Glu Asp Thr Ala Pro Phe Leu Gly
                325                 330                 335

Thr Leu Ala Gly Ala Thr Tyr Glu Glu Val Gln Ser Gln Ile Leu
            340                 345                 350

Glu Ser Ser Ser Leu Pro Glu Asn Thr Val Gln Val Glu Ser Asn Glu
        355                 360                 365

Val Met Gly Ala Pro Asp Asp Arg Thr Arg Thr Pro Leu Glu Pro Ser
370                 375                 380

Asn Cys Trp Ser Asp Leu Asp Gly Gly Asn His Thr Glu Asn Val Gly
385                 390                 395                 400

Glu Ala Ala Val Thr Gln Val Glu Gln Ala Gly Thr Val Ala Ser
                405                 410                 415

Cys Pro Leu Gly His Ser Asp Asp Thr Val Tyr His Asp Asp Lys Cys
            420                 425                 430

Met Val Glu Val Pro Gln Glu Leu Glu Thr Ser Thr Gly His Ser Leu
        435                 440                 445

Glu Lys Glu Phe Thr Asn Gln Glu Ala Ala Glu Pro Lys Glu Val Pro
        450                 455                 460

Ala His Ser Thr Glu Val Gly Arg Asp His Asn Glu Glu Gly Glu
465                 470                 475                 480

Glu Thr Gly Leu Arg Asp Glu Lys Pro Ile Lys Thr Glu Val Pro Gly
                485                 490                 495

Ser Pro Ala Gly Thr Glu Gly Asn Cys Gln Glu Ala Thr Gly Pro Ser
            500                 505                 510

Thr Val Asp Thr Gln Asn Glu Pro Leu Asp Met Lys Glu Pro Asp Glu
```

```
             515                 520                 525
Glu Lys Ser Asp Gln Gln Gly Glu Ala Leu Asp Ser Ser Gln Lys Lys
        530                 535                 540

Thr Lys Asn Lys Lys Lys Asn Lys Lys Lys Ser Pro Val Pro
545                 550                 555                 560

Val Glu Thr Leu Lys Asp Val Lys Lys Glu Leu Thr Tyr Gln Asn Thr
                565                 570                 575

Asp Leu Ser Glu Ile Lys Glu Glu Gln Val Lys Ser Thr Asp Arg
            580                 585                 590

Lys Ser Ala Val Glu Ala Gln Asn Glu Val Thr Glu Asn Pro Lys Gln
                595                 600                 605

Lys Ile Ala Ala Glu Ser Ser Glu Asn Val Asp Cys Pro Glu Asn Pro
            610                 615                 620

Lys Ile Lys Leu Asp Gly Lys Leu Asp Gln Gly Asp Asp Val Gln
625                 630                 635                 640

Thr Ala Ala Glu Glu Val Leu Ala Asp Gly Asp Thr Leu Asp Phe Glu
                645                 650                 655

Asp Asp Thr Val Gln Ser Ser Gly Pro Arg Ala Gly Gly Glu Glu Leu
            660                 665                 670

Asp Glu Gly Val Ala Lys Asp Asn Ala Lys Ile Asp Gly Ala Thr Gln
                675                 680                 685

Ser Ser Pro Ala Glu Pro Lys Ser Glu Asp Ala Asp Arg Cys Thr Leu
            690                 695                 700

Pro Glu His Glu Ser Pro Ser Gln Asp Ile Ser Asp Ala Cys Glu Ala
705                 710                 715                 720

Glu Ser Thr Glu Arg Cys Glu Met Ser Glu His Pro Ser Gln Thr Val
                725                 730                 735

Arg Lys Ala Leu Asp Ser Asn Ser Leu Glu Asn Asp Asp Leu Ser Ala
            740                 745                 750

Pro Gly Arg Glu Pro Gly His Phe Asn Pro Glu Ser Arg Glu Asp Thr
                755                 760                 765

Arg Gly Gly Asn Glu Lys Gly Lys Ser Lys Glu Asp Cys Thr Met Ser
            770                 775                 780

<210> SEQ ID NO 15
<211> LENGTH: 4342
<212> TYPE: DNA
<213> ORGANISM: Homo sapiens

<400> SEQUENCE: 15
ccgtgggacg ggcggaggcg cccgagtccc gcttccccgg cgcccttcca ccccgagccc    60
gactcagccc gcggccacct gcgccccgcc cctgtcggcc gcgcccgagc cagcgccgc    120 gagccgctcc ccggcgggct ggctcctggc cccggaagcg cgagcgttca cttagcggcg    180
agtggctccg tctccgcgga cagagcgcgc gcccctggc ccggcccgcg aggggctccc    240
ggcgcggtcc ccgagcattt cccgccgggt ggagcgggcc gagcccggca ggatgaccag    300
ccccgcggcc gctcaaagcc gggagatcga ctgtttgagc ccggaagcgc agaagctggc    360
ggaagcccgg ctcgctgcaa acgggcggc ccgcgcggag gctcgcgaga tccgcatgaa    420
ggagctggag cggcagcaga aggaggtaga agagagacca gaaaaagatt ttactgagaa    480
ggggtctcgt aacatgccgg gcctgtctgc agccacgctg gcctctctgg gtgggacttc    540
ctctcggaga ggcagcggag acacctccat ctccatcgac accgaggcat ccatcaggga    600
aatcaaggac tctctagcag aagttgaaga gaaatataag aaggctatgg tttccaatgc    660
```

```
tcagctagac aatgaaaaga caaacttcat gtaccaggtt gataccctaa aagatatgtt    720
gctggagctt gaagaacagc tggctgaatc taggcggcag tacgaagaga aaacaaaga    780
atttgaaagg gaaaaacacg cccacagtat actgcaattt cagtttgctg aagtcaagga    840
ggccctgaag caaagagagg aaatgctcga gaaacatgga ataatcctaa attcagaaat    900
agctaccaat ggagagactt ccgacaccct caataatgtt ggataccaag gtcctaccaa    960
gatgacaaaa gaagagttaa atgccctcaa gtcgacaggg gatgggaccc taggaagagc   1020
cagtgaagtg gaggtgaaaa atgaaatcgt ggcgaatgtg gggaaaagag aaatcttgca   1080
caatactgag aaagaacaac acacagagga cacagtgaag gactgtgtgg acatagaggt   1140
attccctgct ggtgagaata ccgaggacca gaaatcctct gaagacactg ccccattcct   1200
aggaacctta gcaggtgcta cctatgagga acaggttcaa agccaaattc ttgagagcag   1260
ttctctccct gaaaacacag tacaggttga gtcaaatgag gtcatgggtg caccagatga   1320
caggaccaga actccccttg agccatccaa ctgttggagt gacttagatg gtgggaacca   1380
cacagagaat gtgggagagg cagcagtgac tcaggttgaa gagcaggcag gcacagtggc   1440
ctcgtgtcct ttagggcata gtgatgcaca agtttatcat gatgacaaat gtatggtaga   1500
ggtcccccaa gagttagaga caagcacagg gcatagttta gagaaagaat tcaccaacca   1560
ggaagcagct gagcccaagg aggttccagc gcacagtaca gaagtaggta gggatcacaa   1620
cgaagaagag ggtgaagaaa caggattaag ggacgagaaa ccaatcaaga cagaagttcc   1680
tggttctcca gcaggaactg agggcaactg tcaggaagcg acaggtccaa gtacagtaga   1740
cactcaaaat gaacccttag atatgaaaga gcccgatgaa gaaaagagtg accaacaggg   1800
agaggcattg gactcatcgc agaagaagac aaagaacaag aaaaagaaaa acaagaagaa   1860
aaaatcccca gtacccgtag aaaccccttaa agatgttaaa aaagagttaa cgtatcagaa   1920
cacagattta agtgaaatta aggaagaaga gcaggtaaag tctactgaca gaaagtcagc   1980
agtggaagcc caaaacgagg tgactgaaaa tccaaaacag aaaattgcag cagaaagcag   2040
tgaaaatgtt gattgtccgg agaatcctaa aattaagttg gatggaaaac ttgaccaaga   2100
aggtgatgat gtacaaacag cagctgagga ggtactagct gatggagaca cattagattt   2160
tgaggatgac accgttcaat catcaggccc gagggctggt ggtgaagaat tagatgaagg   2220
tgttgcaaaa gataatgcta aaatagatgg tgccactcaa agcagtcctg cagaaccaaa   2280
gagcgaagac gcagatcgct gcaccctgcc cgaacatgaa agtccctcac aggacattag   2340
tgatgcctgt gaagcagaaa gtacagagag gtgtgagatg tcagaacatc caagtcagac   2400
cgtcaggaaa gctttagaca gcaatagcct agagaacgat gacttgtcgg caccaggaag   2460
agagccaggg cacttcaatc cagaaagcag agaagatacc agaggaggga atgagaaggg   2520
caaaagcaaa gaagactgta ccatgtccta agctgaggca ggcggcaggc gcggtgcaca   2580
ggaagtctca gtgtgaaggg gtcttttctc tccactgcca atgtaagtag aatgttctaa   2640
attcatagag aggcactgta tgacaattac caggtgctct actgctttaa gttatagact   2700
gttacttgta gatttccatg taatcattga ggttatcacc cagattagaa agacatattt   2760
gttatcagtg tacgttctaa ttgagagcat tccagtagta tcaaacaata atgtctactg   2820
tttatagtcc acttaataaa aatagaggca tttactattt gccttaggct gataggaatg   2880
tgggttttct tgaccaaata tatcagcatc taattgaaat gaccaaatag cattcttaga   2940
cttctgtatt atgaatataa ttgatatttt aattaatgtc ttgttcacat atgtgtactt   3000
```

```
tcatatttga ttttaaaatg tacattataa cctgtatggt attttattta aaggagataa    3060
acagccaaat agcaaatagg tcactgaatg ataagatttg caccttagaa caataatcat    3120
tttaaggata acaagtaaat gtctgaaagc atgaggggct ttatttgcct ttacctcata    3180
tgagtctttg atcttgaacc gatacttttg gatctcattg ttgatatacc tgaatttact    3240
ttgtaagaga ttttaacttc acttcatgct gatgatgtat caaattcatt ttatagaaag    3300
atttaaagtt tttttctgga agtgatatat gtcaaattac atttcctact gcagtatttg    3360
agcagggaca gtcattttt aaatgttttt ggccgggcgt ggtggctcat gcctgtaatc    3420
tcagtacatt gggaggccaa ggcaggtgga tcacctgagg tcaagagttc gaggccagcc    3480
tggccaacat ggtgaaaccc tgtctctact aaaaatacaa aaaattggcc gggcgtgatg    3540
gtgggcgcct gtaatcccag ccactccaga ggctgaggca ggagaatcgc ttgaacctgc    3600
gaggcagaga ttgcagtgag ccaagatcaa gccattgtac tccagcctgg acaacaagag    3660
cgaaactctg tctaaaaaaa aaaaaaaaa cacacacaca caacacaa tgttttcacg    3720 cctgtaaacc tagcacattg ggaagccaag gtgggaggat tgcttgaggc caggagttca    3780
aggctgcagt gagctatgat tgcacactgt actctagcct gggagacaga gtgagacact    3840
gtctctaaaa aaaaaaaaaa aaaaaaaaa agttttgaa ccttaaaata ctttgtttga    3900
atttctaatc atcattcaaa agagcagtaa aaaatggtta cttgttcttg tacaagctac    3960
taattagact atagtaggat attttaaaga gctgaatcac ttttggtatt ttggtataaa    4020
tattttcatt tgttatgtcc cagtatattc ttactggaaa attcttgttt tgatctgcct    4080
gaagaaaata tctgttttct atataaaaaa attttttaaa ataattgtaa agttagattt    4140
aaaattgtaa aatataaaat cacaaaggaa tgtaccttat gaatgttgtt gacatttat    4200 gaaattatgt ggattcatat tactgttaca agatagaatt gaatgcaaaa agaccaaaac    4260
ctcaataaaa tttgaggaaa acgtgttatt atgtaattga aataaaaaca ttttataatt    4320
gtgcaaaaaa aaaaaaaaaa aa                                            4342
```

<210> SEQ ID NO 16
<211> LENGTH: 752
<212> TYPE: PRT
<213> ORGANISM: Homo sapiens

<400> SEQUENCE: 16

```
Met Thr Ser Pro Ala Ala Gln Ser Arg Glu Ile Asp Cys Leu Ser
1               5                   10                  15

Pro Glu Ala Gln Lys Leu Ala Glu Ala Arg Leu Ala Ala Lys Arg Ala
            20                  25                  30

Ala Arg Ala Glu Ala Arg Glu Ile Arg Met Lys Glu Leu Glu Arg Gln
        35                  40                  45

Gln Lys Glu Val Glu Glu Arg Pro Glu Lys Asp Phe Thr Glu Lys Gly
    50                  55                  60

Ser Arg Asn Met Pro Gly Leu Ser Ala Ala Thr Leu Ala Ser Leu Gly
65                  70                  75                  80

Gly Thr Ser Ser Arg Arg Gly Ser Gly Asp Thr Ser Ile Ser Ile Asp
                85                  90                  95

Thr Glu Ala Ser Ile Arg Glu Ile Lys Asp Ser Leu Ala Glu Val Glu
            100                 105                 110

Glu Lys Tyr Lys Lys Ala Met Val Ser Asn Ala Gln Leu Asp Asn Glu
        115                 120                 125

Lys Thr Asn Phe Met Tyr Gln Val Asp Thr Leu Lys Asp Met Leu Leu
```

-continued

```
            130                 135                 140
Glu Leu Glu Glu Gln Leu Ala Glu Ser Arg Arg Gln Tyr Glu Glu Lys
145                 150                 155                 160

Asn Lys Glu Phe Glu Arg Glu Lys His Ala His Ser Ile Leu Gln Phe
                165                 170                 175

Gln Phe Ala Glu Val Lys Glu Ala Leu Lys Gln Arg Glu Glu Met Leu
            180                 185                 190

Glu Lys His Gly Ile Ile Leu Asn Ser Glu Ile Ala Thr Asn Gly Glu
        195                 200                 205

Thr Ser Asp Thr Leu Asn Asn Val Gly Tyr Gln Gly Pro Thr Lys Met
210                 215                 220

Thr Lys Glu Glu Leu Asn Ala Leu Lys Ser Thr Gly Asp Gly Thr Leu
225                 230                 235                 240

Gly Arg Ala Ser Glu Val Glu Val Lys Asn Glu Ile Val Ala Asn Val
                245                 250                 255

Gly Lys Arg Glu Ile Leu His Asn Thr Glu Lys Glu Gln His Thr Glu
                260                 265                 270

Asp Thr Val Lys Asp Cys Val Asp Ile Glu Val Phe Pro Ala Gly Glu
                275                 280                 285

Asn Thr Glu Asp Gln Lys Ser Ser Glu Asp Thr Ala Pro Phe Leu Gly
            290                 295                 300

Thr Leu Ala Gly Ala Thr Tyr Glu Glu Val Gln Ser Gln Ile Leu
305                 310                 315                 320

Glu Ser Ser Ser Leu Pro Glu Asn Thr Val Gln Val Glu Ser Asn Glu
                325                 330                 335

Val Met Gly Ala Pro Asp Asp Arg Thr Arg Thr Pro Leu Glu Pro Ser
            340                 345                 350

Asn Cys Trp Ser Asp Leu Asp Gly Gly Asn His Thr Glu Asn Val Gly
            355                 360                 365

Glu Ala Ala Val Thr Gln Val Glu Glu Gln Ala Gly Thr Val Ala Ser
        370                 375                 380

Cys Pro Leu Gly His Ser Asp Asp Thr Val Tyr His Asp Asp Lys Cys
385                 390                 395                 400

Met Val Glu Val Pro Gln Glu Leu Glu Thr Ser Thr Gly His Ser Leu
                405                 410                 415

Glu Lys Glu Phe Thr Asn Gln Glu Ala Ala Glu Pro Lys Glu Val Pro
                420                 425                 430

Ala His Ser Thr Glu Val Gly Arg Asp His Asn Glu Glu Gly Glu
        435                 440                 445

Glu Thr Gly Leu Arg Asp Glu Lys Pro Ile Lys Thr Glu Val Pro Gly
    450                 455                 460

Ser Pro Ala Gly Thr Glu Gly Asn Cys Gln Glu Ala Thr Gly Pro Ser
465                 470                 475                 480

Thr Val Asp Thr Gln Asn Glu Pro Leu Asp Met Lys Glu Pro Asp Glu
                485                 490                 495

Glu Lys Ser Asp Gln Gln Gly Glu Ala Leu Asp Ser Ser Gln Lys Lys
            500                 505                 510

Thr Lys Asn Lys Lys Lys Asn Lys Lys Lys Ser Pro Val Pro
        515                 520                 525

Val Glu Thr Leu Lys Asp Val Lys Lys Glu Leu Thr Tyr Gln Asn Thr
    530                 535                 540

Asp Leu Ser Glu Ile Lys Glu Glu Glu Gln Val Lys Ser Thr Asp Arg
545                 550                 555                 560
```

-continued

```
Lys Ser Ala Val Glu Ala Gln Asn Glu Val Thr Glu Asn Pro Lys Gln
            565                 570                 575
Lys Ile Ala Ala Glu Ser Ser Glu Asn Val Asp Cys Pro Glu Asn Pro
            580                 585                 590
Lys Ile Lys Leu Asp Gly Lys Leu Asp Gln Glu Gly Asp Asp Val Gln
            595                 600                 605
Thr Ala Ala Glu Glu Val Leu Ala Asp Gly Asp Thr Leu Asp Phe Glu
            610                 615                 620
Asp Asp Thr Val Gln Ser Ser Gly Pro Arg Ala Gly Gly Glu Glu Leu
625                 630                 635                 640
Asp Glu Gly Val Ala Lys Asp Asn Ala Lys Ile Asp Gly Ala Thr Gln
            645                 650                 655
Ser Ser Pro Ala Glu Pro Lys Ser Glu Asp Ala Asp Arg Cys Thr Leu
            660                 665                 670
Pro Glu His Glu Ser Pro Ser Gln Asp Ile Ser Asp Ala Cys Glu Ala
            675                 680                 685
Glu Ser Thr Glu Arg Cys Glu Met Ser Glu His Pro Ser Gln Thr Val
            690                 695                 700
Arg Lys Ala Leu Asp Ser Asn Ser Leu Glu Asn Asp Asp Leu Ser Ala
705                 710                 715                 720
Pro Gly Arg Glu Pro Gly His Phe Asn Pro Glu Ser Arg Glu Asp Thr
            725                 730                 735
Arg Gly Gly Asn Glu Lys Gly Lys Ser Lys Glu Asp Cys Thr Met Ser
            740                 745                 750
```